US005922320A

United States Patent [19]
Vogel et al.

[11] Patent Number: 5,922,320
[45] Date of Patent: Jul. 13, 1999

[54] RECOMBINANT PROCVF

[75] Inventors: Carl-Wilhelm Vogel; Reinhard Bredehorst, both of Hamburg, Germany; David Fritzinger, Alexandria, Va.; Michael Kock, Hamburg, Germany

[73] Assignee: Georgetown University, Washington, D.C.

[21] Appl. No.: 08/662,227

[22] Filed: Jun. 14, 1996

[51] Int. Cl.[6] .......................... A61K 38/48; A61K 38/36; A61K 38/17; C12N 9/64
[52] U.S. Cl. ...................... 424/94.64; 435/226; 530/380; 530/395; 514/8; 514/12
[58] Field of Search .............................. 424/94.64; 514/8, 514/12; 530/380, 395; 435/226

[56] References Cited

U.S. PATENT DOCUMENTS 4,289,690  9/1981  Pestka et al. .......................... 530/351
4,727,028  2/1988  Santerre et al. ...................... 435/240.2

FOREIGN PATENT DOCUMENTS

94/23024  10/1994  WIPO .

OTHER PUBLICATIONS

E. Teicher et al, *Immunochemistry*, vol. 10, pp. 265–271 (1973).
R. Arnon et al, *Proc. Nat. Acad. Sci. USA*, vol. 68, pp. 1450–1455 (1971).
C–W. Vogel et al, *Journal of Immunological Methods*, vol. 73, pp. 203–220 (1984).
D.C. Fritzinger et al, Aug. 4–8, 1991, Abstract, 15th International Congress of Biochemistry.
Poster Material (9 Sheets) Presented at Cambridge, England, Sep. 1991 and at Anaheim California, on Tuesday Apr. 7, 1992.
Pepys et al, *Journal of Immunological Methods*, vol. 30, pp. 105–117 (1979).
Eggersten et al, *Molecular Immunology*, vol. 18, pp. 125–133 (1981).
Fritzinger et al, "Molecular Cloning of Cobra Venum Factor and Cobra C3: Structural Homology with Human C3", Presented at 6th Pan–American Biochemistry Congress, SA Paulo Brazil, Feb. 1990, *FASEB*, vol. 4, P A1903 (1990).
Fritzinger et al, *FASEB Journal*, vol. 6, P A1453, (Apr. 7, 1992).
Fritzinger et al, *Complement and Inflammation*, vol. 8, p. 152 (Abstract No. 76) (1991).
Fritzinger et al, *Complement and Inflammation*, vol. 8, p. 152 (Abstract No. 77) (1991).
Johnson et al, *Federation Proceedings*, vol. 36, p. 1245, Entry No. 5169 (1977).
Vogel et al, *The Journal of Immunology*, vol. 133, pp. 3235–3241 (1984).
O'Keefe et al, *The Journal of Biological Chemistry*, vol. 263, pp. 12690–12697 (1988).
Kunkel et al, *Immunology III*, Bellanti Ed., W.B. Saunders Co., (1985) Chapter 6.
Grier et al, *The Journal of Immunology*, vol. 139, pp. 1245–1252 (1987).
Vogel, *Immunology and Allergy Clinics of North America*, vol. 11, pp. 277–299 (1991).
Vogel et al, *Proc. Natl. Acad. Sci.*, vol. 78, pp. 7707–7711 (1981).
Vogel et al, *Hematology and Blood Transfusion*, vol. 29, pp. 514–517, (1985).
Sakiyalak et al, *Mol. Immunol.*, vol. 30, Supp 1, (1993) (Abstract).
Petrella et al, *Journal of Immunological Methods*, vol. 104, pp. 159–172 (1987).
Juhl et al, *Molecular Immunology*, vol. 27, pp. 957–964 (1990).
Vogel, Chapter 5, "Handbook of Natural Toxins", TU Ed., New York, NY 1991.
Vogel et al., *Developmental and Comparative Immunology*, vol. 9, pp. 311–325 (1985).
Gowda et al, *Molecular Immunology*, vol. 29, pp. 335–342 (1992).
Beukelman et al, *Journal of Immunological Methods*, vol. 97, pp. 119–122 (1987).
Mierendorf et al, *Methods in Enzymology*, vol. 152, pp. 458–469.
*Handbook of Experimental Immunology*, Boston, MA, Weir Ed., pp. 39.34–39.49 (986).
Petrella et al, *Complement and Inflammation*, vol. 6, pp. 386–387, (1989).
Fritzinger et al, Abstract, Dialog File 155, Accession Number 93056528, (1992).
Von Zabern et al, *Scan J. Immunol.*, vol. 15, pp. 357–362, (1982).
D.C. Fritzinger et al. "Molecular Cloning and Derived Primary Structure of Cobra Venom Factor", *Proc. Natl. Acad. sci.* 91(26): 12775–12779, Dec. 1994.

*Primary Examiner*—Rebecca E. Prouty
*Attorney, Agent, or Firm*—Oblon, Spivak, McClelland, Maier & Neustadt, P.C.

[57] ABSTRACT

Recombinant proCVF exhibits substantially the same activity as CVF and is useful for lowering complement activity.

7 Claims, 32 Drawing Sheets

```
                    Signal Sequence                                   -1|+1    N-terminus of α-chain
        M  E  R  M  A  L  Y  L  V  A  A  L  L  I  G  F  P  G  S  S  H  G  A  L  Y  T  L  T        7
-22     CCCATGGAGAGGATGGCTCTCTATCTGGTGGCTGCTCTATTGATTGGTTTTCCAGGTGTCTCTCATGGGCTCTCTACACCCTCATCACC    90
  1

P  A  V  L  R  T  D  T  E  E  Q  I  L  V  E  A  H  G  D  S  T  P  K  Q  L  D  I  F  V  H    37
  8     CCTGCTGTTTGCCAACAGACACAGAGGAACAAATTTTGGTGGAGGCCCATGGAGACAGTACTCCAAAACAGCTTGACATCTTTGTTCAT    180
 91

D  F  P  R  K  Q  K  T  L  F  Q  T  R  V  D  M  N  P  A  G  G  M  L  V  T  P  T  I  E  I    67
 38     GATTTTCCACGGAAGCAGAAAACCCTTGTTCCAAACCAGTAGATATGAATCCAGCAGGAGGCATGCTTGTCACTCCAACTATAGAGATT    270
181

P  A  K  E  V  S  T  D  S  R  Q  N  Q  Y  V  V  V  Q  V  T  G  P  Q  V  R  L  E  K  V  V    97
 68     CCAGCCAAAGAAGTGAGTACGGACTCCAGGCAACAATCAATATGTGGTTGTGCAAGTAACTGGTCCTCAAGTGAGATTGGAAAAGGTGTT    360
271

L  L  S  Y  Q  S  S  F  L  F  I  Q  T  D  K  G  I  Y  T  P  G  S  P  V  L  Y  R  V  F  S    127
 98     CTCCTTTCTTACCAGAGTAGCTTTCTGTTTATCCAGACAGATAAAGGCATCTATACACCAGGGTCTCCAGTACTCTATCGTGTTTTTCT    450
361
                                     CHO                                      CHO
        M  D  H  N  T  S  K  M  N  K  T  V  I  V  E  F  Q  T  P  E  G  I  L  V  S  S  N  S  V  D    157
128     ATGGATCACAACACAAGCAAGATGAACAAGACTGTGATTGTTGAGTTTCAGACTCCAGAAGGCATTCTCGTCAGTTCTAATTCAGTTGAC    540
451
                                                                                                CHO
        L  N  F  F  W  P  Y  N  L  P  D  L  V  S  L  G  T  W  R  I  V  A  K  Y  E  H  S  P  E  N    187
158     CTAAAACTTCTTCTGGCCTTACAATTTACCAGACCTTGTCAGTTGGGGACTTGGAGGATTGTGCCAAATATGAACATTCCCAGAGAAT    630
541

Y  T  A  Y  F  D  V  R  K  Y  V  L  P  S  F  E  V  R  L  Q  P  S  E  K  F  F  Y  I  D  G    217
188     TATACTGCATATTTTGATGTCAGGAAATATGTGTTGCCAAGCTTTGAAGTCCGTCTCCAACCATCAGAGAAGTTTTTTACATTGACGGC    720
631

N  E  N  F  H  V  S  I  T  A  R  Y  L  Y  G  E  E  V  E  G  V  A  F  V  L  F  G  V  K  I    297
218     AATGAAAATTTCCAGTGTCTATCACTGCAAGGTACTTGTATGGAGAGGAAGTGGAAGTGGCCTTTGTCCTCTTTGGAGTGAAAATA     810
721
```

FIG.2A

```
248   D D A K K S I P D S L T R I P I I D G D G K A T L K R D T F                                  277
811   GATGATGCTAAAAAGAGTATTCCAGACTCACTCAGAGAATTCGATTATTGATGGAGATGGAAAGCAACACTAAAAGAGATACATTC        900

278   R S R F P N L N E L V G H T L Y A S V T V M T E S G S D N V                                  307
901   CGTTCTCGATTTCCAAATCTCAATGAGCTTGTTGGGCATACTCTGTATGCATCTGTAACAGTCATGACAGAATCAGGCAGTGATATGGTA    990

308   V T E Q S G I H I V A S P Y Q I H F T K T P K Y F K P G N P                                  337
991   GTGACTGAGCAAAGCGGCATTCATATTGTGGCATTCCCTATCAGATCCACTTCACAAAAACCCCAAATATTTCAAGCCAGGAATGCCA     1080

338   Y E L T V Y Y V T N P D G S P A A H V P V V S E A F H S N G T                                367
1081  TATGAACTGACGGTGTATTATGTTACCAACCCTGATGGCTCACCAGCTGCCCATGTGCCCAGTGGTATCAGAGGCCTTTCATTCTATGGAACC 1170

368   T L S D G T A K L I L N I P L N A Q S L P I T V R T N H G D                                  397
1171  ACTTTGAGTGATGGGACTGCTAAGCTCATCCTGAACATACCATTGAACATGCTCAAAGCTCTACCAATCACTGTTAGAACTAACCATGGAGAC 1260

398   L P R E R Q A T K S M T A I A Y Q T Q G G S G N Y L H V A I                                  427
1261  CTCCCAAGAGAACGCCAGGCAACAAAGTCCATGACAGCCATAGCCTACCAAACCCAGGGAGGATCTGGAAACTATCTTCATGTAGCCATT    1350

428   T S T E I K P G D N L P V N F N V K G N A N S L K Q I K Y F                                  457
1351  ACATCTACAGAGATTAAGCCCGGAGATAACTTACCTGTCAATTTCAATGTGAAGGGCAATGCCAATTCACTGAAGCAGATCAAATATTTC    1440

458   T Y L I L N K G K I F K V G R Q P R R D G Q N L V T N N L H                                  467
1441  ACATACCTCATATATTGAATAAAGGGAAGATTTTCAAGGTTGGCAGGCAACCCAGGAGAGATGGGCAGAATCTGGTGACCAATGAATCGCAT   1530

488   I T P D L I P S F R F V A Y Y Q V G N N E I V A D S V W V D                                  517
1531  ATCACTCCAGATCTCATCCCTTCCTTCCGGTTTGTGGCTTACTACCAAGTGGAAACAACGAAATTGTGGCTGATTCTGTCTGGGTGGAT    1620
```

FIG.2B

```
518  V  K  D  T  C  M  G  T  L  V  V  K  G  D  N  L  I  Q  M  P  G  A  A  M  K  I  K  L  E  G         547
1621 GTGAAGGATACCTGCATGGGAACGTTGGTTGTGAAGGGAGACAATCTAATACAAATGCCAGGAGCTGCAATGAAAATCAAATTGGAAGGG      1710

548  D  P  G  A  R  V  G  L  V  A  V  D  K  A  V  Y  Y  V  L  N  D  K  Y  K  I  S  Q  A  K  I  W     577
1711 GATCCAGGTGCTCGGGTTGGTCTTGTGGCTGTGGACAAAGCAGTATATGTTCTCAATGATAAATATAAGATTAGCCAAGCTAAGATATGG      1800

578  D  T  I  E  K  S  D  F  G  C  T  A  G  S  G  Q  N  N  L  G  V  F  B  D  A  G  L  A  L  T        607
1801 GACACAATAGAAAAGAGTGACTTTGGCTGTACAGCTGGCAGTGGCCAGAATAATCTGGGTGTGTTTGAAGATGCTGGACTGGCTCTGACA      1890
                                       C-terminus of α-chain|         |N-terminus of "C3α"

608  T  S  T  N  L  N  T  K  Q  R  S  A  A  K  C  P  Q  P  A  N  R  R  R  R  S  S  V  L  L           637
1891 ACCAGCACTAATCTCAACACCAAAGCAGATCAGCTGCCAAAGTGTCCTCAGCCTGCAAATCGGAGGCGTCGCAGTTCTGTTTTGCTGCTT      1980
                CHO

638  D  S  N  A  S  K  A  A  E  F  Q  D  Q  D  L  R  K  C  C  E  D  V  M  H  E  N  P  M  G  Y        667
1981 GACAGCAACGCCAAGCGCAAAGCGGCAGAATTTCAGGATCAGGATCTGAGAAAGTGTTGTGAAGATGTCATGCATGAGAACCCCATGGGGTAC  2070

668  T  C  E  K  R  A  K  Y  I  Q  E  G  D  A  C  K  A  A  F  L  E  C  C  R  Y  I  K  G  V  R        697
2071 ACTTGTGAAAAGCGTGCCAAAATACATCCAGGAGGAGATGCTTGTAAGGCTGCCTTCCTTGAATGCTGTCGCTACATCAAGGGGGTCCGA      2160
                                                                                |N-terminus of γ-chain 698  D  E  N  Q  R  E  S  E  L  F  L  A  R  D  D  N  E  D  G  F  I  A  D  S  D  I  I  S  R  S        727
2161 GATGAAAACCAACGGGAGAGCGAGTTGTTTCTGGCAAGAGATGATAATGAAGATGGTTTCATAGCAGATAGTGATATCATCTCAAGGTCT      2250

728  D  F  P  K  S  W  L  W  L  T  K  D  L  T  E  E  P  N  S  Q  G  I  S  S  K  T  M  S  F  Y        757
2251 GATTTCCCAAGAGTTGGTTGTGGCTAACAAGGACTTGACCGAGGAGCCTAACAGTCAAGGGATTTCAAGCAAGACAATGTCTTTTAT        2340

758  L  R  D  S  I  T  T  W  V  V  L  A  V  S  F  T  P  T  K  G  I  C  V  A  E  P  Y  E  I  R        787
2341 CTGAGGGATTCCATCACAACCTGGGTGGTGCTGGCTGTAAGCTTTACACCCACCAAAGGGATCTGTGTGGCTGAACCTTATGAAATAAGA      2430
```

FIG.2C

```
788   V  M  K  V  F  F  I  D  L  Q  M  P  Y  S  V  V  K  N  E  Q  V  E  I  R  A  I  L  H  N  Y      817
2431  GTCATGAAAGTCTTCTTCATTGATCTTCAAATGCCATATTCAGTAGTGAAGAATGAGCAGGTGGAGATTCGAGCTATTCTGCACAACTAC     2520

818   V  N  E  D  I  Y  V  R  V  E  L  L  Y  N  P  A  F  C  S  A  S  T  K  G  Q  R  Y  R  Q  Q      847
2521  GTTAACGAGGATATTTATGTGCGAGTGGAACTGTTATACAACCCAGCTTTCTGCAGTGCTTCCACAAAGGACAAAGATACCGACAGCAG     2610

848   F  P  I  K  A  L  S  S  R  A  V  P  F  V  I  V  P  L  E  Q  G  L  H  D  V  E  I  K  A  S      877
2611  TTCCCAATTAAAGCCCTGTCCTCCAGAGCAGTACCGGTTTGTGATAGTCCCATTAGAGCAAGGATTGCATGATGTTGAGATTAAAGCAAGT     2700

878   V  Q  E  A  L  W  S  D  G  V  R  K  K  L  K  V  V  P  E  G  V  Q  K  S  I  V  T  I  V  K      907
2701  GTCCAGGAAGCGTTGTGGTCAGACGGTGTGAGAAAGAAGCTGAAAGTTGTACCTGAAGGGTACCAGAAATCCATTGTGACTATTGTTAAA     2790

908   L  D  P  R  A  K  G  V  G  G  T  Q  L  E  V  I  K  A  R  K  L  D  D  R  V  P  D  T  E  I      937
2791  CTGGACCCAAGGGCCAAAGGAGTTGGTGGAACACAGCTAGAAGTGATCAAAGCCCGCAAATTAGATGACAGAGTGCCTGACACAGAAATT     2880
                                                                                C-terminus of γ-chain(?)

938   E  T  K  I  I  I  Q  G  D  P  V  A  Q  I  I  E  N  S  I  D  G  S  K  L  N  H  L  I  I  T      967
2881  GAAACCAAGATTATCATCCAAGGTGACCCTGTGGCTCAGATTATTGAAAACTCAATTGATGGAAGTAAACTCAACCATCTCATTATCACT     2970
                                                          Thioester Site 968   P  S  G  C  G  E  Q  N  M  I  R  M  A  A  P  V  I  A  T  Y  Y  L  D  T  T  E  Q  W  E  T      997
2971  CCTTCTGGCTGTGGGGAGCAAAATATGATCCGGATGGCCGCACCAGTTATTGCCACCTACTACCTGGACACCACAGAGCAGTGGGAGACT     3060

998   L  G  I  N  R  R  T  E  A  V  N  Q  I  V  T  G  Y  A  Q  Q  M  V  Y  K  K  A  D  H  S  Y     1027
3061  CTCGGCATAAATCGCCGGACTGAAGCTGTCAATCAGATCGTGACTGGTTATGCCCAGCAGATGGTGTACAAGAAGCAGATCATTCCTAT     3150

1028  A  A  F  T  N  R  A  S  S  W  L  T  A  Y  V  V  K  V  F  A  M  A  A  K  M  V  A  G  I        1057
3151  GCAGCATTTACAAACCCGTGCATCTAGTTGGCTAACAGCATATGTCGTAAAAGTCTTTGCCATGGCTGCCAAAATGTAGCAGGCATT      3240
```

FIG.2D

```
1058  S  H  E  I  I  C  G  G  V  R  W  L  I  L  N  R  Q  Q  P  D  G  A  F  K  E  N  A  P  V  L   1087
3241  ACTCATGAAATCATTTGTGGAGGTGTGAGGTGGCCTGGCCTGATTCTGAACAGGCAACACCAGAGACGATGGAGCGTTCAAAGAAAATGCCCCTGTACTT  3330

1088  S  G  T  M  Q  G  G  I  Q  G  A  E  E  E  V  Y  L  T  A  F  I  L  V  A  L  L  E  S  K  T   1117
3331  TCTGGAACAATGCAGGGAGGAATTCAAGGTGCTGAAGAAGAAGTATATTTAACAGCTTTCATTCTTGGTTGCCTTGTTGGAATCCAAAACA  3420

1118  I  C  N  D  Y  V  N  S  L  D  S  S  I  K  K  A  T  N  Y  L  L  K  K  Y  E  K  L  Q  R  P   1147
3421  ATCTGCAATGACTATGTCAATAGTCTAGACAGCAGCATCAAGAAGGCCACAAATTATTTACTCAAAAAGTATGAGAAACTGCAAAGGCCT  3510

1148  Y  T  T  A  L  T  A  Y  A  L  A  A  A  D  Q  L  N  D  D  R  V  L  M  A  A  S  T  G  R  D   1177
3511  TACACTACAGCCCTCACAGCTTATGCTTTGGCTGCTGCAGACCAACTCAATGATGACAGGGTACTCATGGCAGCATCAACAGGAAGGGAT  3600

1178  H  W  E  E  Y  N  A  H  T  H  N  I  E  G  T  S  Y  A  L  L  A  L  L  K  M  K  K  F  D  Q   1207
3601  CATTGGGAAGAATACAATGCTCACACCCACAACATTGAAGGCACTTCCTATGCCTTGTTGGCCCTGCTGAAAATGAAGAAATTTGATCAA  3690

1208  T  G  P  I  V  R  W  L  T  D  Q  N  F  Y  G  E  T  Y  G  Q  T  Q  A  T  V  N  A  F  Q  A   1237
3691  ACTGGTCCCATAGTCAGATGGCTGACAGATCAGAATTTTTATGGGGAAACATATGGACAAACCCAAGCAACAGTTATGGCATTTCAAGCT  3780

N-terminus of β-chain
1238  L  A  E  Y │E  I  Q  M  P  T  H  K  D  L  N  L  D  I  T  I  E  L  P  D  R  E  V  P  I  R   1267
3781  CTTGCTGAATATGAGATTCAGATGCCTACCCATAAGGACTTAAACTTAGATATTACTATTGAACTGCCAGATCGAGAAGTACCTATAAGG  3870

1268  Y  R  I  N  Y  E  N  A  L  L  A  R  T  V  E  T  K  L  N  Q  D  I  T  V  T  A  S  G  D  G   1297
3871  TACAGAATTAATTATGAAAATGCTCTCCTGGCTCGGACAGTAGAGACCAAGCTCAACCAAGACATCACTGTGACCGCATCAGGTGATGGA  3966
                                                                                        CHO

1298  K  A  T  M  T  I  L  T  F  Y  N  A  Q  L  Q  E  K  A  N  V  C  N  K  F  H  L  N  V  S  V   1327
3961  AAAGCAACAATGACCATTTTGACATTCTATAACGCACAGTTGCAGGAGAAGGCAAATGTTTGCAATAAATTTCATCTTAATGTTTCTGTT  4050
```

FIG.2E

```
       E   I   H   L   N   A   N   G   A   K   G   A   L   M   L   K   I   C   T   R   Y   L   G   E   V   D   S   T   M                    1357
1328 GAAAACATCCACTTGAATGCAAATGGAGCCAAGGGAGCCCTCATGCTCAAGATCTGCACAAGGTATCTGGGAGAAGTTGATTCTACAATG                                                4140
4051

T   I   I   D   I   S   M   L   T   G   F   L   P   D   A   E   D   L   T   R   L   S   K   G   V   D   R   Y   I   S                1387
1358 ACAATAATTGATATTTCTATGCTGACTGGTTTTCTCCCTGATGCTGAAGACCTTACAAGGCTTTCTAAAGGAGTGGACAGATACATCTCC                                                4230
4141

R   Y   E   V   D   N   N   M   A   Q   K   V   A   V   I   I   Y   L   N   K   V   S   H   S   E   D   E   C   L   H                1417
1388 AGATATGAAGTTGACAATAATATGGCTCAGAAAGTAGCTGTTATCATTTACTTAAACAAGGTCTCCCACTCTGAAGATGAATGCCTGCAC                                                4320
4231

F   K   I   L   K   H   F   E   V   G   F   I   Q   P   G   S   V   K   V   Y   S   Y   Y   N   L   D   E   K   C   T                1447
1418 TTTAAGATTCTCAAGCATTTTGAAGTTGGCTTCATTCAGCCAGGATCAGTCAAGGTATACAGCTACTACAATCTAGATGAAAAATGTACC                                                4410
4321

K   F   Y   H   P   D   K   G   T   G   L   L   M   K   I   C   I   G   N   V   C   R   C   A   G   E   T   C   S   S                1477
1448 AAGTTCTACCATCCAGATAAAGGAACAGGCCTTCTCATGAAGATATGTATTGGTAACGTTGCCGATGTGCAGGAGAACCTGTTCCTCG                                                  4500
4411

L   N   H   Q   E   R   I   D   V   P   L   Q   I   E   K   A   C   E   T   N   V   D   Y   V   Y   K   L   L                        1507
1478 CTCAACCATCAGGAAAGGATGATGTTCCATTACAAATTGAAAAAGCCTGCGAGACGAATGTGGATTATGTCTACAAAACCAAGCTGCTT                                                 4590
4501

R   I   E   E   Q   D   G   N   D   I   Y   V   M   D   V   L   E   V   I   K   Q   G   T   D   E   N   P   R   A   K                1537
1508 CGAATAGAAGAACAAGATGGTAATGATATCTATGTCATGGATGTTTTAGAAGTTATTAAACAAGGTACTGACGAAAATCCACGAGCAAAG                                                4680
4591

T   H   Q   Y   I   S   Q   R   K   C   Q   E   A   L   N   L   K   V   N   D   D   Y   L   I   W   G   S   R   S   D                1567
1538 ACCCACCAGTACATAAGTCAAAGGAAATGCCAGGAGGCTCTGAATCTGAAGGTGAATGATGATTATCTGATCTGGGGTTCCAGGAGTGAC                                                4770
4681

L   L   P   T   K   D   K   I   S   Y   I   I   T   K   N   T   W   I   E   R   W   P   H   E   D   E   C   Q   E   E                1597
1568 CTGTTGCCCACGAAAGATAAAATTTCCTACATCATTACAAAGAACACATGGATTGAGAGATGGCCACATGAAGACGAATGTCAGGAAGAA                                                4860
4771
```

FIG.2F

```
                              C-terminus of β-chain
          E  F  Q  K  L  C  D  D  F  A  Q  F  S  Y  T  L  T  E  F  G  C  P  T                              1620
1598
4861      GAATTCCAAAAGTTGTGTGATGACTTGCTCAGTTAGCTACACATTGACTGAGTTGGCTGCCTACTTAAAAGTTCAGAAGAATCAAT              4950

4951      GATAGGAAGGAAATTCTCAGAAGACAGATTTTGAGCCAATGCATATATGTTACTTGCCTCTTGATCTTTAGTTTTATGTCAATTTGC             5040

5041      TCTGTTATTTCCCTTAAATTGTTTATACATAAAATAAATAATCGATTTCTTACTTTGATATGTTCTTGATTTTTAATAAACAATGGTGA           5130

5131      TTCATGATTATTTTTTCTCTTCTCTGATCCATCCAATATTTGAAGTGCTCTGAACAGAGCACTTATGGAGTAATGTTTTAGTGATGGATG          5220

5221      AATAAGTTGGTGAGTCAATATTATCAGGCCCTATATACTCTTATGGAAGATCGATTGTACCCAAAGAACATAGATTGAAATGTGTTAC            5310

5311      TTTGAAAACAGAGGTTTCAGTTGTATATGTTTACACTTGGATACAATCTTAACTCTTAATAAACACTGATCTCAGAACATTTAACAGCTG          5400

5401      CTATTTAATAATGACAAAATATTCTTGACTGCACCCACAGAAAACATTGCATTACATTAGAATGGGTTTTATCAGATGACTAAGTCTGC           5490

5491      TAGACTTGCCATCTGTCAAAATGTGCCTCTTCCCCAGCTCCAACTTTAAGGATAGTAACTAATAGATGTTCTCTCATTGGCTCCTGACAG          5580

5581      AGGTGTGGTAGCCACTGAGTTTCCCTGGATGACACTAGAAGCTGGCCACGACACTGCAGCCTGGTGGAGGGCCCTCTTTTGCTATCCATG          5670

5671      AGCTTCTATTCATCCTCTTATCGTTGGGATGGGACGTCTCGATTTTCCAGGTATACAGGTGATCTCATTTACTAACATCACC                  5760

5761      ACTAACTTCAAGGATTGGTTGAGGGGTTATGCCAATGTGATTGAAGGTTTCACCCATGTGAATCTATTCTCCAATCCCAATGCTGTATCT         5850

5851      ATGCTGCTCATTTCTGCTTGTAAAATGGTATAAAAAGAATAAACACTGCCCAGGCAGTCAGACATCTTTGGACACTG(A)20                  5948
```

FIG. 2G

```
       714                723   % IDENTICAL   % SIMILAR
CVF1   EDGFIADSDI
COBRA C3  EDELFGDDNI           40            90
HUMAN C3  DEDILAEENI           30            90
```

FIG.3

```
          1382                        1411   % IDENTICAL   % SIMILAR
CVF1      VDRYISRYEVDNNMAQKVAVIIYLNKVSHS
COBRA C3  VDRYISKFEIDNNMAQKGTVVIYLDKVSHS        40            90
HUMAN C3  VDRYISKYELDKAFSDRNTLIIYLDKVSHS        30            90
```

FIG.4

|        | % IDENTIFY | % SIMILARITY |
|--------|------------|--------------|
|        | 85         | 88           |
|        | 73         | 81           |

```
           964                                  989
CVF1        LIITPSGCGEQNMIRMAAPVIATYYL
COBRA C3    LIITPSGCGEQNMITMTPSVIATYYL
HUMAN C3    LIVTPSGCGEQNMIGMTPTVIAVHYL
```

FIG.5

|        | % IDENTIFY | % SIMILARITY |
|--------|------------|--------------|
|        | 50         | 79           |
|        | 36         | 79           |

```
           708                      721
CVF1        LARDDNEDGFIADS
COBRA C3    LARSDFEDELFGDD
HUMAN C3    LARSNLDEDIIAEE
                       ↑
              N-TERMINUS OF CVF1 γ-CHAIN
              (C3 CONVERTASE CLEAVEAGE SITE)
```

```
        711                       731
CVF1      DDNEDGFIADSDIISRSDFPK
COBRA C3  SDFEDELFGDDNIISRSDFPE
HUMAN C3  SNLDEDIIAEENIVSRSEFPE
```

| | % IDENTICAL | % SIMILAR |
|---|---|---|
| | 57 | 81 |
| | 38 | 81 |

FIG.7B

```
          1168                                                1230
                                          1180       1191
CVF       VLMAASTGRDHMEEYNAHTHNIEGTSYALLALLKMKKFDQTGPIVRWLTDQNFYGETYGQTQA
COBRA C3  VLMAASTGRNRMEEYNARTHNIEGTSYALLALLKMKKFVEAGPVVRWLTDQKYYGGTYGQTQA
HUMAN C3  KFLTTAKDKNRWEDPGKQLYNVEATSYALLALLQLKDFVPPVVRWLNEQRYYGGGYGSTQA
                                              ↑
                                      CR2 BINDING SITE
```

| | % IDENTICAL | % SIMILAR |
|---|---|---|
| | 83 | 94 |
| | 46 | 70 |

```
            1               15
CVF1      .ALYTLITPAVLRTDT
Cobra C3  .ALYTLITPAVLRTDT
Human C3  SPMYSIITPNILRLES
Mouse C3  IPMYSIITPNVLRLES
```

FIG.9A

```
          1242                    1264
CVF1      EIQMPTHKDLNLDITIELPDREV
Cobra C3  EIQMPTHQDLNLDISIKLPDREV
Human C3  QKDAPDHQELNLDVSLQLPSRSS
Mouse C3  QKTAVDHKDLNMDVSFHLPSRSS
```

FIG.9B

```
          711                   732
CVF1      DDNEDGFIADSDIISRSDFPKS
Cobra C3  SDFEDELFGDDNIISRSDFPES
Human C3  SNLDEDIIAEENIVSRSEFPES
Mouse C3  SELEEDIIPEEDIISRSHFPQS
```

FIG.9C

```
      I  P  S  G  G  D  M  V  M  T  E  Q  S  G  I  H  I  V  T  S  P  Y  Q  I  Y  F  T  K  T
  1  GAATTCCATCAGGAGGAGGTGATATGGTAATGACTGAGCAAAGTGGCATTCATATTGTGACATCTCCCTATCAGATCTACTTCACAAAAACC      89

P  K  Y  F  K  P  G  M  P  Y  E  L  T  V  Y  V  T  K  P  D  G  S  P  A  A  H  V  P  V  V
 90  CCCAAATATTTCAAGCCAGGAATGCCATATGAACTGACGGTGTATGTTACCAAACCTGATGGCTCACCAGTGCCAGTGGTA              179

S  E  A  I  H  S  E  G  T  T  L  S  D  G  T  A  K  L  F  L  N  T  P  Q  N  A  Q  S  L  P
180  TCAGAGGCCATTCATTCTGAGGGAACCACTTTGAGTGATGGGACTGCTAAGCTCTTCCTGAACACACCACAAAATGCTCAAAGCCTACCG      269

I  T  V  R  T  N  H  G  D  L  P  R  E  R  Q  A  I  K  S  M  T  A  T  A  Y  Q  T  Q  G  G
270  ATCACTGTTAGAACTAACCATGGAGACCTCCCAAGAGAACGCCAGGCAATAAAGTCCATGACAGCCACAGCCTACCAAACCCAGGGAGGA      359

S  G  N  Y  L  H  V  A  I  T  S  E  I  K  P  G  D  N  L  P  V  N  F  N  V  R  G  N  A
360  TCTGGAAACTATCTTCATGTAGCCATTACATCTACAGAGATTAAGCCCGGAGATAACTTACCTGTCAATTTCAATGTGAGGGCAATGCA      449

N  S  L  N  Q  I  K  Y  F  T  Y  L  I  L  N  K  G  K  I  F  K  V  G  R  Q  H  R  G  D  G
450  AATTCACTGAACCAGATCAAATATTTCACATACCTCATACTGAATAAAGGGAAGATTTTCAAGGTTGGCAGGCAACACAGGGGAGATGGG      539

N  L  V  T  M  N  L  H  I  T  P  D  L  I  P  S  F  R  F  V  A  Y  Y  Q  V  G  N  N  E  I
540  GAGAATCTGGTGACCATGAATCTACATATCACTCCAGATCTCATTCCTTCCTTCCGGTTTGTGGCTTACTACCAAGTGGGAAACAATGAA      629

E  V  A  D  S  V  W  V  D  V  K  D  T  C  M  G  T  L  V  V  K  G  A  T  S  R  D  N  R  I
630  ATTGTGGCTGATTCTGTCTGGGTGGATGTGAAGGATACCTGCATGGGAACGTTGGTTGTGAAAGGAGCGACTTCCAGAGACAATCGAATA      719

FIG.10A
```

```
       Q  M  P  G  A  A  M  K  I  K  L  E  G  D  P  G  A  W  I  G  L  V  A  V  D  K  A  E  Y  V
720   CAAATGCCAGGAGCTGCAATGAAAATCAAATTGGAAGGGGATCCAGGTGCTTGGATTGGTCTTGTGGCTGTGGACAAAGCAGAATATGTT    809

L  N  D  K  Y  K  I  S  Q  A  K  I  W  D  T  I  E  K  S  D  F  G  C  T  A  G  S  G  Q  N
810   CTCAATGATAAATATAAGATTAGCCAAGCTAAGATATGGGACACAATAGAAAAGAGTGACTTTGGCTGTACAGCTGGCAGTGGCCAGAAT    899

N  L  G  V  F  E  D  A  G  L  A  L  T  T  S  T  N  L  N  T  K  Q  R  S  A  A  K  C  P  Q
900   AATCTGGGTGTGTTTGAAGATGCTGGACTGGCTCTGACAACCAGCACTAATCTCAACACCAAACAGAGATCAGCTGCAAAGTGTCCTCAG    989

P  A  N  R  R  R  S  S  V  L  L  D  S  N  A  S  K  A  A  Q  F  Q  D  Q  D  L  R  K
990   CCTGCAAATCGGAGGCGTCGCAGTTCTGTTTTGCTTGACAGCAACGCAAGCAAAGGCACAGTTTCAGGATCAAGACCTGCGTAAA       1079
```

```
                P  E  G  E  W  K  S  I  V  T  I  I  E  L  D  P  H  T  K  G  I  G  G  T  Q  V  E  L  V  K
1800    CCTGAAGGGGAATGGAAAAGTATTGTTACTATTATTGAACTGGACCCACATACAAAAGGAATTGGTGGAACACAGGTAGAATTGGTCAAA    1889

A  N  K  L  N  D  R  V     P  D  T  E  I  E  T  K  I  T  I  Q  G  D  P  V  A  Q  T  I  E  N
1890    GCCAATAAATTAAATGACAGGGTTCCTGATACGGAAATAGAAACCAAGATTACTATTCAAGGTGATCCTGTGGCTCAGACTATTGAAAAC    1979

S  I  D  G  S  K  L  N  H  L  I  I  T  P  F  G  C  G  E  Q  N  M  I  R  M  T  A  P  V  I
1980    TCAATTGATGGAAGTAAACTCAACCATCTCATTATCACTCCTTTTGGCTGTGGGGAGCAAAATATGATCCGCATGACTGCACCAGTTATT    2069

A  T  Y  L  D  T  T  Q  Q  W  E  T  L  G  I  N  R  R  T  E  A  V  N  Q  I  M  T  G  Y
2070    GCCACCTACTACCTGGACACCACACAGCAGTGGGAGACTCTCGGCATAAATCGCAGGACTGAAGCTGTCAATCAGATCATGACTGGTTAT    2159
```

FIG. 10D

```
           A  Q  L  V  Y  K  K  A  D  H  S  Y  A  A  F  T  N  S  A  S  S  S  W  L  T  A  Y  V  V
2160   GCCCAGCAGTTGGTGTACAAGAAAGCAGACCATTCCTATGCAGCATTTACAAACAGTGCATCTAGTTCTTGGCTAACAGCATATGTTGTA   2249

K  I  F  A  L  A  A  K  I  V  K  D  I  N  H  E  I  V  C  G  G  M  R  W  L  I  L  N  R  Q
2250   AAAATCTTTGCCTTGGCTGCCAAAATTGTAAAAGACATTAACCATGAAATCGTTTGTGGAGGTATGAGGTGGCTGATTCTGAACAGGCAA   2339

R  T  D  G  V  F  R  E  N  A  P  V  L  F  G  T  M  Q  G  G  I  Q  G  A  E  P  E  G  S  L
2340   CGAACAGATGGAGTGTTCAGAGAAAACGCCCCTGTACTTTTTGGAACAATGCAGGGAGGCATTCAAGGTGCTGAACCAGAAGGATCTTTA   2429

T  A  F  I  L  V  A  L  L  E  S  R  S  I  C  N  A  Y  I  N  I  L  D  S  S  I  S  K  A  T
2430   ACAGCTTTCATTCTGGTTGCGTTGTTGGAATCCAGATCAATCTGCAATGCATATATCAATATTCTAGACAGCAGCATCAGTAAGGCCACA   2519

D  Y  L  L  K  K  Y  E  K  L  Q  R  P  Y  T  T  A  L  T  A  Y  A  L  A  A  A  E  R  L  N
2520   GATTATTTACTCAAAAAGTATGAGAAACTGCAAAGGCCTTACACTACAGCCCTTACAGCCTATGCTTTGGCTGCAGAACGACTCAAT     2609

D  D  R  V  L  M  A  A  S  T  G  R  N  R  W  E  E  P  N  A  H  T  H  N  I  E  G  T  S  Y
2610   GATGACAGGGTACTCATGGCAGCATCAACAGGAAGGAATCGTTGGGAAGAACCTAACGCCCACACCATAACATTGAAGGCACTTCCTAT    2699

A  L  A  L  L  K  M  K  K  F  V  E  A  G  P  V  V  Q  W  L  I  D  Q  Q  Y  Y  G  G  T
2700   GCCTTGTTGGCCCTGCTGAAAATGAAGAAATTTGTTGAGGCCGGTCCTGTAGTCCAATGGCTGATAGATCAGCAATATTATGGGGGAACA    2789

Y  G  Q  T  Q  A  T  V  M  M  F  Q  A  L  A  E  Y  E  I  Q  M  P  T  H  K  D  L  N  L  D
2790   TATGGACAAACCCAAGCAACAGTTATGATGTTTCAAGCTCTTGCTGAATATGAGATTCAGATGCCTACCCATAAGGACTTAAACTTAGAT  2879
```

FIG. 10E

```
        I  T  I  E  L  P  D  R  E  V  P  I  R  Y  R  I  N  Y  E  N  A  L  L  A  Q  T  V  E  T  K
2880  ATTACTATTGAACTGCCAGATCGAGAAGTACCTATAAGGTACAGAGAATTAATTATGAAAATGCTCTCCTGGCTCAGACAGTAGAGACCAAA  2969

L  N  E  D  F  T  V  S  A  S  G  D  G  K  A  T  M  T  I  L  T  V  Y  N  A  Q  L  R  E  D
2970  CTCAACGAAGACTTCACTGTGTCAGCATCAGGTGATGGAAAAGCAACAATGACCATTTTGACGGTCTATAATGCACAATTGAGGGAGGAT    3059

A  N  V  C  N  K  F     H  L  D  V  S  V  E  N  V  Q  L  N  L  K  E  A  K  G  A  K  G  A  L
3060  GCAAATGTTTGCAACAAATTCCATCTTGATGTTTCTGTTGAAAACGTCCAGTTGAACTTAAAAGAGGCAAAGGGAGCCAAGGGAGCCCTC    3149

K  L  K  I  C  T  R  Y  L  G  E  V  D  S  T  M  T  I  I  D  V  S  M  L  T  G  F  V  P  D
3150  AAGCTCAAAATCTGCACTAGGTATCTGGGAGAAGTTGATTCTACAATGACAATAATTGATGTTTCTATGCTGACTGGTTTTGTCCCTGAT   3239
```

FIG.10F

```
       T  E  D  L  T  R  L  S  K  G  V  D  R  Y  I  S  M  F  E  I  N  N  N  M  A  Q  K  G  T  V
3240   ACTGAAGACCTTACGAGGCTTTCTAAAGGAGTCGACAGATATATCTCCATGTTTGAAATTAACAATAATATGGCTCAGAAAGGAACTGTT      3329

I  I  Y  L  D  K  V  S  H  S  E  D  E  C  L  H  F  K  I  L  K  H  F  E  V  G  F  I  Q  P
3330   ATCATTTACTTAGACAAGGTCTCCCACTCTGAAGATGAATGCCTGCACTTTAAGATTCTCAAGCATTTTGAAGTTGGCTTCATTCAGCCA     3419

G  S  V  K  V  Y  S  Y  Y  N  L  D  E  K  C  T  K  I  Y  H  P  D  E  A  T  G  L  L  N  K
3420   GGATCAGTCAAGGTGTACAGCTACTACAACATCTAGATGAAAAATGTACCAAGATCTACCATCCAGATGAAGCAACAGGCCTTCTCAATAAG    3509

I  C  V  G  N  V  C  R  C  A  E  E  T  C  S  L  L  N  Q  Q  K  N  V  T  R  Q  L  R  I  Q
3510   ATATGTGTTGGTAACGTTTGCCGATGTGCAGAAGAAACCTGTTCCTTGCTCAACCAGCAGAAGAATGTTACTCGGCAATTGCGAATTCAG     3599

K  A  F  D  P  N  V  D  Y  V  Y  K  T  L  L  R  I  E  E  K  D  G  N  D  I  Y  V  M  D
3600   AAAGCCTTCGATCCAAATGTGGATTATGTCTATAAAACCAAGCTGCTTCGAATAGAAGAAAAAGATGGTAATGATATATCTATGTCATGGAC    3689

V  L  E  V  L  K  Q  G  T  D  Q  N  Q  Q  V  K  R  Q  Y  V  S  Q  R  K  C  Q  E  A  L
3690   GTTTTAGAAGTTCTTAAACAAGGCACTGACCAAAATCAACAAGTAAAGGTCCGCCAGTATGTAAGTCAAAGGAAATGCCAGGAGGCTTTG     3779

N  L  M  V  N  N  D  Y  L  I  W  G  P  S  S  D  L  W  P  M  K  D  K  I  S  Y  L  I  T  K
3780   AATCTGATGGTGAATAATGATTATCTGATCTGGGGTCCAAGCAGTGACCTGTGGCCCATGAAAGATAAAATTTCCTATCTCATTACAAAG     3869

N  T  W  I  E  R  W  P  H  E  D  K  C  Q  E  E  F  Q  K  L  C  D  Q  F  A  L  F  S  Y
3870   AACACCTGGATTGAGAGATGGCCACATGAAGACAAATGTCAGGAAGAATTCCAAAAGTTGTGTGATCAGTTTGCTCTGTTTAGCTAC       3959

A  M  S  L  L  P  Y  L  K  V  Q  N  N  Q
3960   GCAATGAGTTTGCTGCCCTACTTAAAAGTTCAGAATAATCAATGATAGGAAGGAAATTCTCAGAGACAGATTTTGAGCCAATACATAT       4049

4050   ATGTTACTTGTCTCTTAATTTTTTAGTTTTCTGTCATTGCTGTGCTGTTTCCCTTAAATTGTTATACATAGAATAAATGGAATTC         4138
```

FIG. 10G

|  | ConA | GNA | SNA | MAA | PNA | DSA |
|---|---|---|---|---|---|---|
| rCVF | ● | ○ |  |  | ● |  |
| CVF | ● |  |  |  |  |  |

FIG.16

```
                Signal Sequence          -1|+1  N-terminus of α-chain
 -22  MERMALYLVAALLIGFPGSSHGALYTLITPAVLRTDTEEQILVEAHGDSTPKQLDIFVH   37
                                                        CHO
  38  DFPRKQKTLFQTRVDMNPAGGMLVTPTIEIPAKEVSTDSRQNQYVVVQTGPQVRLEKVV   97
                                       CHO           CHO
  98  LLSYQSSFLFIQTDKGIYTPGSPVLYRVFSMDHNTSKMNKTVIVEFQTPEGILVSSNSVD  157
 158  LNFFWPYNLPDLVSLGTWRIVAKYEHSPENYTAYFDVRKYVLPSFEVRLQPSEKFFYIDG  217
 218  NENFHVSITARYLYGEEVEGVAFVLFGVKIDDAKKSIPDSLTRIPIIDGDKATLKRDTF   277
 278  RSRFPNLNELVGHTLYASVTVMTESGSDMVVTEQSGIHIVASPYQIHFTKTPKYFKPGMP  337
 338  YELTVYVTNPDGSPAAHVPVVSEAFHSMGTTLSDGTAKLILNIPLNAQSLPITVRTNHGD  397
 398  LPRERQATKSMTAIAYQTQGCSGNYLHVAITSTEIKPGDNLPVNFNVKGNANSLKQIKYF  457
 458  TYLILNKGKIFKVGRQPRRDGQNLVTMNLHITPDLIPSFRFVAYYQVGNNEIVADSVWVD  517
                                                     N-terminus of "C3a"
 518  VKDTCMGTLVVKGDNLIQMPGAAMKIKLEGDPGARVGLVAVDKAVYVLNDKYKISQAKIW  577
                                              C-terminus of α-chain
 578  DTIEKSDFGCTAGSGQNNLGVFEDAGLALTTSTNLNTKRQSAAKCPQPANRRRSSVLLL   637
      CHO
      C-terminus of "C3a"     N-terminus of γ-chain
 638  DSNASKAAEFQDQDLRKCCEDVMHENPMGYTCEKRAKYIQEGDACKAAFLECCRYIKGVR  697
 698  DENQRESELFLARDDNEDGFIADSDIISRSDFPKSWLWLTKDLTEEPNSQGISSKTMSPY  757
 758  LRDSITTWVVLAVSFTPTKGICVAEPYEIRVMKVFFIDLQMPYSVVKNEQVEIRAILHNY  817
```

FIG.21A

| | | |
|---|---|---|
| 818 | V N E D I Y V R V E L L Y N P A F C S A S T K G Q R Y R Q Q F P I K A L S S R A V P F V I V P L E Q G L H D V E I K A S | 877 |
| 878 | V Q E A L W S D G V R K K L K V V P E G V Q K S I V T I V K L D P R A K G V G G T Q L E V I K A R K L D D R V P D T E I | 937 |
| | C-terminus of γ-chain(?)    Thioester Site | |
| 938 | E T K I I I Q G D P V A Q I I E N S I D G S K L N H L I I T P S G C G E Q N M I R M A A P V I A T Y Y L D T T E Q W E T | 997 |
| 998 | L G I N R R T E A V N Q I V T G Y A Q Q M V Y K K A D H S Y A A F T N R A S S S W L T A Y V V K V F A M A A K M V A G I | 1057 |
| 1058 | S H E I I C C G G V R W L I L N R Q Q P D G A F K E N A P V L S G T M Q G C I Q G A E E E V Y L T A F I L V A L L E S K T | 1117 |
| 1118 | I C N D Y V N S L D S S I K K A T N Y L L K K Y E K L Q R P Y T T A L T A Y A L A A A D Q L N D D R V L M A A S T G R D | 1177 |
| 1178 | H W E E Y N A H T H N I E G T S Y A L L A L L K M K K F D Q T G P I V R W L T D Q N F Y G E T Y G Q T Q A T V M A F Q A | 1237 |
| | N-terminus of β-chain | |
| 1238 | L A E Y E I Q M P T H K D L N L D I T I E L P D R E V P I R Y R I N Y E N A L L A R T V E T K L N Q D I T V T A S G D G | 1297 |
| | CHO | |
| 1298 | K A T M T I L T F Y N A Q L Q E K A N V C N K F H L N V S V E N I H L N A M G A K G A L M L K I C T R Y L G E V D S T M | 1357 |
| 1358 | T I I D I S M L T G F L P D A E D L T R L S K G V D R Y I S R Y E V D N N M A Q K V A V I I Y L N K V S H S E D E C L H | 1417 |
| 1418 | F K I L K H F E V G F I Q P G S V K V Y S Y N L D E K C T K F Y H P D K G T G L L N K I C I G N V C R C A G E T C S S | 1477 |
| 1478 | L N H Q E R I D V P L Q I E K A C E T N V D Y V Y K T K L L R I E E Q D G N D I Y V M D V L E V I K Q G T D E N P R A K | 1537 |
| 1538 | T H Q Y I S Q R K C Q E A L N L K V N D D Y L I W G S R S D L L P T K D K I S Y I I T K N T W I E R W P H E D E C Q E E | 1597 |
| | C-terminus of β-chain | |
| 1598 | E F Q K L C D D F A Q F S Y T L T E F G C P T ■■■■■ | 1620 (1626) |

FIG.21B

SEQUENCE LISTING (1) GENERAL INFORMATION:

(iii) NUMBER OF SEQUENCES: 39

(2) INFORMATION FOR SEQ ID NO:1:

(i) SEQUENCE CHARACTERISTICS:
      (A) LENGTH: 5948 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
CCCATGGAGA GGATGGCTCT CTATCTGGTG GCTGCTCTAT TGATTGGTTT TCCAGGGTCT      60

TCTCATGGGG CTCTCTACAC CCTCATCACC CCTGCTGTTT TGCGAACAGA CACAGAAGAG     120

CAAATTTTGG TGGAGGCCCA TGGAGACAGT ACTCCAAAAC AGCTTGACAT CTTTGTTCAT     180

GATTTTCCAC GGAAGCAGAA AACCTTGTTC CAAACCAGAG TAGATATGAA TCCAGCAGGA     240

GGCATGCTTG TCACTCCAAC TATAGAGATT CCAGCAAAAG AAGTGAGTAC GGACTCCAGG     300

CAAAATCAAT ATGTGGTTGT GCAAGTAACT GGTCCTCAAG TGAGATTGGA AAAGGTGGTT     360

CTCCTTTCTT ACCAGAGTAG CTTTCTGTTT ATCCAGACAG ATAAAGGCAT CTATACACCA     420

GGGTCTCCAG TACTCTATCG TGTTTTTTCT ATGGATCACA ACACAAGCAA GATGAACAAA     480

ACTGTGATTG TTGAGTTTCA GACTCCAGAA GGCATTCTTG TCAGTTCTAA TTCAGTTGAC     540

CTAAACTTCT TCTGGCCTTA CAATTTACCA GACCTTGTCA GTTTGGGGAC TTGGAGGATT     600

GTGGCCAAAT ATGAACATTC CCCAGAGAAT TATACTGCAT ATTTTGATGT CAGGAAATAT     660

GTGTTGCCAA GCTTTGAAGT CCGTCTGCAA CCATCAGAGA AGTTTTTTTA CATTGACGGC     720

AATGAAAATT TCCACGTGTC TATCACTGCA AGGTACTTGT ATGGAGAGGA AGTGGAAGGT     780

GTGGCCTTTG TCCTCTTTGG AGTGAAAATA GATGATGCTA AAAAGAGTAT TCCAGACTCA     840

CTCACGAGAA TTCCGATTAT TGATGGAGAT GGGAAAGCAA CACTAAAAAG AGATACATTC     900
```

-continued

```
CGTTCTCGAT TTCCAAATCT CAATGAGCTT GTTGGGCATA CTCTGTATGC ATCTGTAACA      960
GTCATGACAG AATCAGGCAG TGATATGGTA GTGACTGAGC AAAGCGGCAT TCATATTGTG     1020
GCATCTCCCT ATCAGATCCA CTTCACAAAA ACCCCCAAAT ATTTCAAGCC AGGAATGCCA     1080
TATGAACTGA CGGTGTATGT TACCAACCCT GATGGCTCAC CAGCTGCCCA TGTGCCAGTG     1140
GTATCAGAGG CCTTTCATTC TATGGGAACC ACTTTGAGTG ATGGGACTGC TAAGCTCATC     1200
CTGAACATAC CATTGAATGC TCAAAGCCTA CCAATCACTG TTAGAACTAA CCATGGAGAC     1260
CTCCCAAGAG AACGCCAGGC AACAAAGTCC ATGACAGCCA TAGCCTACCA AACCCAGGGA     1320
GGATCTGGAA ACTATCTTCA TGTAGCCATT ACATCTACAG AGATTAAGCC CGGAGATAAC     1380
TTACCTGTCA ATTTCAATGT GAAGGGCAAT GCAAATTCAC TGAAGCAGAT CAAATATTTC     1440
ACATACCTCA TATTGAATAA AGGGAAGATT TTCAAGGTTG CAGGCAACC CAGGAGAGAT     1500
GGGCAGAATC TGGTGACCAT GAATCTGCAT ATCACTCCAG ATCTCATCCC TTCCTTCCGG     1560
TTTGTGGCTT ACTACCAAGT GGGAAACAAC GAAATTGTGG CTGATTCTGT CTGGGTGGAT     1620
GTGAAGGATA CCTGCATGGG AACGTTGGTT GTGAAGGAG ACAATCTAAT ACAAATGCCA     1680
GGAGCTGCAA TGAAAATCAA ATTGGAAGGG GATCCAGGTG CTCGGGTTGG TCTTGTGGCT     1740
GTGGACAAAG CAGTATATGT TCTCAATGAT AAATATAAGA TTAGCCAAGC TAAGATATGG     1800
GACACAATAG AAAAGAGTGA CTTTGGCTGT ACAGCTGGCA GTGGCCAGAA TAATCTGGGT     1860
GTGTTTGAAG ATGCTGGACT GGCTCTGACA ACCAGCACTA ATCTCAACAC CAAACAGAGA     1920
TCAGCTGCAA AGTGTCCTCA GCCTGCAAAT CGGAGGCGTC GCAGTTCTGT TTTGCTGCTT     1980
GACAGCAACG CAAGCAAAGC GGCAGAATTT CAGGATCAAG ACCTGCGTAA ATGCTGTGAA     2040
GATGTCATGC ATGAGAACCC CATGGGGTAC ACTTGTGAAA AGCGTGCAAA ATACATCCAG     2100
GAGGGAGATG CTTGTAAGGC TGCCTTCCTT GAATGCTGTC GCTACATCAA GGGGGTCCGA     2160
GATGAAAACC AACGGGAGAG CGAGTTGTTT CTGGCAAGAG ATGATAATGA AGATGGTTTC     2220
ATAGCAGATA GTGATATCAT CTCAAGGTCT GATTTCCCCA AGAGTTGGTT GTGGCTAACA     2280
AAGGACTTGA CCGAGGAGCC TAACAGTCAA GGGATTTCAA GCAAGACAAT GTCTTTTTAT     2340
CTGAGGGATT CCATCACAAC CTGGGTGGTG CTGGCTGTAA GCTTTACACC CACCAAAGGG     2400
ATCTGTGTGG CTGAACCTTA TGAAATAAGA GTCATGAAAG TCTTCTTCAT TGATCTTCAA     2460
ATGCCATATT CAGTAGTGAA GAATGAGCAG GTGGAGATTC GAGCTATTCT GCACAACTAC     2520
GTTAACGAGG ATATTTATGT GCGAGTGGAA CTGTTATACA ACCCAGCCTT CTGCAGTGCT     2580
TCCACAAAAG GACAAAGATA CCGACAGCAG TTCCCAATTA AAGCCCTGTC CTCCAGAGCA     2640
GTACCGTTTG TGATAGTCCC ATTAGAGCAA GGATTGCATG ATGTTGAGAT TAAAGCAAGT     2700
GTCCAGGAAG CGTTGTGGTC AGACGGTGTG AGGAAGAAAC TGAAAGTTGT ACCTGAAGGG     2760
GTACAGAAAT CCATTGTGAC TATTGTTAAA CTGGACCCAA GGGCAAAAGG AGTTGGTGGA     2820
ACACAGCTAG AAGTGATCAA AGCCCGCAAA TTAGATGACA GAGTGCCTGA CACAGAAATT     2880
GAAACCAAGA TTATCATCCA AGGTGACCCT GTGGCTCAGA TTATTGAAAA CTCAATTGAT     2940
GGAAGTAAAC TCAACCATCT CATTATCACT CCTTCTGGCT GTGGGGAGCA AAATATGATC     3000
CGCATGGCCG CACCAGTTAT TGCCACCTAC TACCTGGACA CCACAGAGCA GTGGGAGACT     3060
CTCGGCATAA ATCGCAGGAC TGAAGCTGTC AATCAGATCG TGACTGGTTA TGCCCAGCAG     3120
ATGGTGTACA AGAAAGCAGA TCATTCCTAT GCAGCATTTA CAAACCGTGC ATCTAGTTCT     3180
TGGCTAACAG CATATGTCGT AAAAGTCTTT GCCATGGCTG CCAAAATGGT AGCAGGCATT     3240
AGTCATGAAA TCATTTGTGG AGGTGTGAGG TGGCTGATTC TGAACAGGCA ACAACCAGAT     3300
```

-continued

```
GGAGCGTTCA AAGAAAATGC CCCTGTACTT TCTGGAACAA TGCAGGGAGG AATTCAAGGT    3360

GCTGAAGAAG AAGTATATTT AACAGCTTTC ATTCTGGTTG CGTTGTTGGA ATCCAAAACA    3420

ATCTGCAATG ACTATGTCAA TAGTCTAGAC AGCAGCATCA AGAAGGCCAC AAATTATTTA    3480

CTCAAAAAGT ATGAGAAACT GCAAAGGCCT TACACTACAG CCCTCACAGC CTATGCTTTG    3540

GCTGCTGCAG ACCAACTCAA TGATGACAGG GTACTCATGG CAGCATCAAC AGGAAGGGAT    3600

CATTGGGAAG AATACAATGC TCACACCCAC AACATTGAAG GCACTTCCTA TGCCTTGTTG    3660

GCCCTGCTGA AAATGAAGAA ATTTGATCAA ACTGGTCCCA TAGTCAGATG GCTGACAGAT    3720

CAGAATTTTT ATGGGGAAAC ATATGGACAA ACCCAAGCAA CAGTTATGGC ATTTCAAGCT    3780

CTTGCTGAAT ATGAGATTCA GATGCCTACC CATAAGGACT TAAACTTAGA TATTACTATT    3840

GAACTGCCAG ATCGAGAAGT ACCTATAAGG TACAGAATTA ATTATGAAAA TGCTCTCCTG    3900

GCTCGGACAG TAGAGACCAA ACTCAACCAA GACATCACTG TGACAGCATC AGGTGATGGA    3960

AAAGCAACAA TGACCATTTT GACATTCTAT AACGCACAGT TGCAGGAGAA GGCAAATGTT    4020

TGCAATAAAT TTCATCTTAA TGTTTCTGTT GAAAACATCC ACTTGAATGC AATGGGAGCC    4080

AAGGGAGCCC TCATGCTCAA GATCTGCACA AGGTATCTGG GAGAAGTTGA TTCTACAATG    4140

ACAATAATTG ATATTTCTAT GCTGACTGGT TTTCTCCCTG ATGCTGAAGA CCTTACAAGG    4200

CTTTCTAAAG GAGTGGACAG ATACATCTCC AGATATGAAG TTGACAATAA TATGGCTCAG    4260

AAAGTAGCTG TTATCATTTA CTTAAACAAG GTCTCCCACT CTGAAGATGA ATGCCTGCAC    4320

TTTAAGATTC TCAAGCATTT TGAAGTTGGC TTCATTCAGC CAGGATCAGT CAAGGTGTAC    4380

AGCTACTACA ATCTAGATGA AAAATGTACC AAGTTCTACC ATCCAGATAA AGGAACAGGC    4440

CTTCTCAATA AGATATGTAT TGGTAACGTT TGCCGATGTG CAGGAGAAAC CTGTTCCTCG    4500

CTCAACCATC AGGAAAGGAT TGATGTTCCA TTACAAATTG AAAAAGCCTG CGAGACGAAT    4560

GTGGATTATG TCTACAAAAC CAAGCTGCTT CGAATAGAAG AACAAGATGG TAATGATATC    4620

TATGTCATGG ATGTTTTAGA AGTTATTAAA CAAGGTACTG ACGAAAATCC ACGAGCAAAG    4680

ACCCACCAGT ACATAAGTCA AAGGAAATGC CAGGAGGCTC TGAATCTGAA GGTGAATGAT    4740

GATTATCTGA TCTGGGGTTC CAGGAGTGAC CTGTTGCCCA CGAAAGATAA AATTTCCTAC    4800

ATCATTACAA AGAACACATG GATTGAGAGA TGGCCACATG AAGACGAATG TCAGGAAGAA    4860

GAATTCCAAA AGTTGTGTGA TGACTTTGCT CAGTTTAGCT ACACATTGAC TGAGTTTGGC    4920

TGCCCTACTT AAAAGTTCAG AAGAATCAAT GATAGGAAGG AAATTCTCAG AAGACAGATT    4980

TTTGAGCCAA TGCATATATG TTACTTTGCC TCTTGATCTT TTAGTTTTAT GTCAATTTGC    5040

TCTGTTATTT TCCCTTAAAT TGTTTATACA TAAAATAAAT AATCGATTTC TTACTTTGAT    5100

ATGTTCTTGA TTTTTAATAA ACAATGGTGA TTCATGATTA TTTTTTTCTT CTTCTGATCC    5160

ATCCAATATT TGAAGTGCTC TGAACAGAGC ACTTATGGAG TAATGTTTTA GTGATGGATG    5220

AATAAGTTGG TGAGTCAATA TTATCAGGCC CTATATACTC TTATGGAAGA TCGATTTGTA    5280

CCCAAAGAAA CATAGATTGA AATGTGTTAC TTTGAAAACA GAGGTTTCAG TTGTATATGT    5340

TTACACTTGG ATACAATCTT AACTCTTAAT AAACACTGAT CTCAGAACAT TTAACAGCTG    5400

CTATTTAATA ATGACAAAAT ATTCTTTGAC TGCACCCACA GAAAACATTG CATTACATTA    5460

GAATGGGTTT TATCAGATGA CTAAGTCTGC TAGACTTGCC ATCTGTCAAA ATGTGCCTCT    5520

TCCCCAGCTC CAACTTTAAG GATAGTAACT AATAGATGTT CTCTCATTGG CTCCTGACAG    5580

AGGTGTGGTA GCCACTGAGT TTCCCTGGAT GACACTAGAA GCTGGCAGCA CACTGCAGCC    5640

TGGTGGAGGG GCCTCTTTTG CTATCCCATG AGCTTCTATT CATCCTCTTA TCTGTTGGGA    5700
```

```
TGGGGATGGG ACGTCTCTGA TTTTCCAGGT ATACAGGTGA TCTCATTTAC TAACATCACC    5760

ACTAACTTCA AGGATTGGTT GAGGGGTTAT GCCAATGTGA TTGAAGGTTT CACCCATGTG    5820

AATCTATTCT CCAATCCCAA TGCTGTATCT ATGCTGCTCA TTTCTGCTTG TAAAAATGGT    5880

ATAAAAAGAA TAAACACTGC CCAGGCAGTC AGACATCTTT GGACACTGAA AAAAAAAAAA    5940

AAAAAAAA                                                             5948
```

(2) INFORMATION FOR SEQ ID NO:2:

(i) SEQUENCE CHARACTERISTICS:
        (A) LENGTH: 1642 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Glu Arg Met Ala Leu Tyr Leu Val Ala Leu Leu Ile Gly Phe
 1               5                  10                  15

Pro Gly Ser Ser His Gly Ala Leu Tyr Thr Leu Ile Thr Pro Ala Val
            20                  25                  30

Leu Arg Thr Asp Thr Glu Glu Gln Ile Leu Val Glu Ala His Gly Asp
        35                  40                  45

Ser Thr Pro Lys Gln Leu Asp Ile Phe Val His Asp Phe Pro Arg Lys
 50                  55                  60

Gln Lys Thr Leu Phe Gln Thr Arg Val Asp Met Asn Pro Ala Gly Gly
 65                  70                  75                  80

Met Leu Val Thr Pro Thr Ile Glu Ile Pro Ala Lys Glu Val Ser Thr
                85                  90                  95

Asp Ser Arg Gln Asn Gln Tyr Val Val Gln Val Thr Gly Pro Gln
                100                 105                 110

Val Arg Leu Glu Lys Val Val Leu Ser Tyr Gln Ser Ser Phe Leu
        115                 120                 125

Phe Ile Gln Thr Asp Lys Gly Ile Tyr Thr Pro Gly Ser Pro Val Leu
 130                 135                 140

Tyr Arg Val Phe Ser Met Asp His Asn Thr Ser Lys Met Asn Lys Thr
145                 150                 155                 160

Val Ile Val Glu Phe Gln Thr Pro Glu Gly Ile Leu Val Ser Ser Asn
                165                 170                 175

Ser Val Asp Leu Asn Phe Phe Trp Pro Tyr Asn Leu Pro Asp Leu Val
                180                 185                 190

Ser Leu Gly Thr Trp Arg Ile Val Ala Lys Tyr Glu His Ser Pro Glu
        195                 200                 205

Asn Tyr Thr Ala Tyr Phe Asp Val Arg Lys Tyr Val Leu Pro Ser Phe
 210                 215                 220

Glu Val Arg Leu Gln Pro Ser Glu Lys Phe Phe Tyr Ile Asp Gly Asn
225                 230                 235                 240

Glu Asn Phe His Val Ser Ile Thr Ala Arg Tyr Leu Tyr Gly Glu Glu
                245                 250                 255

Val Glu Gly Val Ala Phe Val Leu Phe Gly Val Lys Ile Asp Asp Ala
                260                 265                 270

Lys Lys Ser Ile Pro Asp Ser Leu Thr Arg Ile Pro Ile Ile Asp Gly
        275                 280                 285

Asp Gly Lys Ala Thr Leu Lys Arg Asp Thr Phe Arg Ser Arg Phe Pro
 290                 295                 300
```

-continued

```
Asn Leu Asn Glu Leu Val Gly His Thr Leu Tyr Ala Ser Val Thr Val
305                 310                 315                 320

Met Thr Glu Ser Gly Ser Asp Met Val Val Thr Gln Ser Gly Ile
            325                 330                 335

His Ile Val Ala Ser Pro Tyr Gln Ile His Phe Thr Lys Thr Pro Lys
                340                 345                 350

Tyr Phe Lys Pro Gly Met Pro Tyr Glu Leu Thr Val Tyr Val Thr Asn
            355                 360                 365

Pro Asp Gly Ser Pro Ala Ala His Val Pro Val Val Ser Glu Ala Phe
        370                 375                 380

His Ser Met Gly Thr Thr Leu Ser Asp Gly Thr Ala Lys Leu Ile Leu
385                 390                 395                 400

Asn Ile Pro Leu Asn Ala Gln Ser Leu Pro Ile Thr Val Arg Thr Asn
                405                 410                 415

His Gly Asp Leu Pro Arg Glu Arg Gln Ala Thr Lys Ser Met Thr Ala
            420                 425                 430

Ile Ala Tyr Gln Thr Gln Gly Gly Ser Gly Asn Tyr Leu His Val Ala
            435                 440                 445

Ile Thr Ser Thr Glu Ile Lys Pro Gly Asp Asn Leu Pro Val Asn Phe
        450                 455                 460

Asn Val Lys Gly Asn Ala Asn Ser Leu Lys Gln Ile Lys Tyr Phe Thr
465                 470                 475                 480

Tyr Leu Ile Leu Asn Lys Gly Lys Ile Phe Lys Val Gly Arg Gln Pro
                485                 490                 495

Arg Arg Asp Gly Gln Asn Leu Val Thr Met Asn Leu His Ile Thr Pro
            500                 505                 510

Asp Leu Ile Pro Ser Phe Arg Phe Val Ala Tyr Tyr Gln Val Gly Asn
        515                 520                 525

Asn Glu Ile Val Ala Asp Ser Val Trp Val Asp Val Lys Asp Thr Cys
530                 535                 540

Met Gly Thr Leu Val Val Lys Gly Asp Asn Leu Ile Gln Met Pro Gly
545                 550                 555                 560

Ala Ala Met Lys Ile Lys Leu Glu Gly Asp Pro Gly Ala Arg Val Gly
                565                 570                 575

Leu Val Ala Val Asp Lys Ala Val Tyr Val Leu Asn Asp Lys Tyr Lys
            580                 585                 590

Ile Ser Gln Ala Lys Ile Trp Asp Thr Ile Glu Lys Ser Asp Phe Gly
        595                 600                 605

Cys Thr Ala Gly Ser Gly Gln Asn Asn Leu Gly Val Phe Glu Asp Ala
610                 615                 620

Gly Leu Ala Leu Thr Thr Ser Thr Asn Leu Asn Thr Lys Gln Arg Ser
625                 630                 635                 640

Ala Ala Lys Cys Pro Gln Pro Ala Asn Arg Arg Arg Arg Ser Ser Val
                645                 650                 655

Leu Leu Leu Asp Ser Asn Ala Ser Lys Ala Ala Glu Phe Gln Asp Gln
            660                 665                 670

Asp Leu Arg Lys Cys Cys Glu Asp Val Met His Glu Asn Pro Met Gly
        675                 680                 685

Tyr Thr Cys Glu Lys Arg Ala Lys Tyr Ile Gln Glu Gly Asp Ala Cys
            690                 695                 700

Lys Ala Ala Phe Leu Glu Cys Cys Arg Tyr Ile Lys Gly Val Arg Asp
705                 710                 715                 720

Glu Asn Gln Arg Glu Ser Glu Leu Phe Leu Ala Arg Asp Asp Asn Glu
                725                 730                 735
```

```
Asp Gly Phe Ile Ala Asp Ser Asp Ile Ile Ser Arg Ser Asp Phe Pro
            740                 745                 750
Lys Ser Trp Leu Trp Leu Thr Lys Asp Leu Thr Glu Glu Pro Asn Ser
            755                 760                 765
Gln Gly Ile Ser Ser Lys Thr Met Ser Phe Tyr Leu Arg Asp Ser Ile
            770                 775                 780
Thr Thr Trp Val Val Leu Ala Val Ser Phe Thr Pro Thr Lys Gly Ile
785                 790                 795                 800
Cys Val Ala Glu Pro Tyr Glu Ile Arg Val Met Lys Val Phe Phe Ile
                    805                 810                 815
Asp Leu Gln Met Pro Tyr Ser Val Val Lys Asn Glu Gln Val Glu Ile
            820                 825                 830
Arg Ala Ile Leu His Asn Tyr Val Asn Glu Asp Ile Tyr Val Arg Val
            835                 840                 845
Glu Leu Leu Tyr Asn Pro Ala Phe Cys Ser Ala Ser Thr Lys Gly Gln
            850                 855                 860
Arg Tyr Arg Gln Gln Phe Pro Ile Lys Ala Leu Ser Ser Arg Ala Val
865                 870                 875                 880
Pro Phe Val Ile Val Pro Leu Glu Gln Gly Leu His Asp Val Glu Ile
                    885                 890                 895
Lys Ala Ser Val Gln Glu Ala Leu Trp Ser Asp Gly Val Arg Lys Lys
            900                 905                 910
Leu Lys Val Val Pro Glu Gly Val Gln Lys Ser Ile Val Thr Ile Val
            915                 920                 925
Lys Leu Asp Pro Arg Ala Lys Gly Val Gly Gly Thr Gln Leu Glu Val
            930                 935                 940
Ile Lys Ala Arg Lys Leu Asp Asp Arg Val Pro Asp Thr Glu Ile Glu
945                 950                 955                 960
Thr Lys Ile Ile Ile Gln Gly Asp Pro Val Ala Gln Ile Ile Glu Asn
                    965                 970                 975
Ser Ile Asp Gly Ser Lys Leu Asn His Leu Ile Ile Thr Pro Ser Gly
            980                 985                 990
Cys Gly Glu Gln Asn Met Ile Arg Met Ala Ala Pro Val Ile Ala Thr
            995                 1000                1005
Tyr Tyr Leu Asp Thr Thr Glu Gln Trp Glu Thr Leu Gly Ile Asn Arg
            1010                1015                1020
Arg Thr Glu Ala Val Asn Gln Ile Val Thr Gly Tyr Ala Gln Gln Met
1025                1030                1035                1040
Val Tyr Lys Lys Ala Asp His Ser Tyr Ala Ala Phe Thr Asn Arg Ala
                    1045                1050                1055
Ser Ser Ser Trp Leu Thr Ala Tyr Val Val Lys Val Phe Ala Met Ala
            1060                1065                1070
Ala Lys Met Val Ala Gly Ile Ser His Glu Ile Ile Cys Gly Gly Val
            1075                1080                1085
Arg Trp Leu Ile Leu Asn Arg Gln Gln Pro Asp Gly Ala Phe Lys Glu
            1090                1095                1100
Asn Ala Pro Val Leu Ser Gly Thr Met Gln Gly Gly Ile Gln Gly Ala
1105                1110                1115                1120
Glu Glu Glu Val Tyr Leu Thr Ala Phe Ile Leu Val Ala Leu Leu Glu
                    1125                1130                1135
Ser Lys Thr Ile Cys Asn Asp Tyr Val Asn Ser Leu Asp Ser Ser Ile
            1140                1145                1150
Lys Lys Ala Thr Asn Tyr Leu Leu Lys Lys Tyr Glu Lys Leu Gln Arg
```

-continued

```
                1155                1160                1165
Pro Tyr Thr Thr Ala Leu Thr Ala Tyr Ala Leu Ala Ala Asp Gln
    1170                1175                1180

Leu Asn Asp Asp Arg Val Leu Met Ala Ser Thr Gly Arg Asp His
1185                1190                1195                1200

Trp Glu Glu Tyr Asn Ala His Thr His Asn Ile Glu Gly Thr Ser Tyr
                1205                1210                1215

Ala Leu Leu Ala Leu Leu Lys Met Lys Lys Phe Asp Gln Thr Gly Pro
            1220                1225                1230

Ile Val Arg Trp Leu Thr Asp Gln Asn Phe Tyr Gly Glu Thr Tyr Gly
        1235                1240                1245

Gln Thr Gln Ala Thr Val Met Ala Phe Gln Ala Leu Ala Glu Tyr Glu
    1250                1255                1260

Ile Gln Met Pro Thr His Lys Asp Leu Asn Leu Asp Ile Thr Ile Glu
1265                1270                1275                1280

Leu Pro Asp Arg Glu Val Pro Ile Arg Tyr Arg Ile Asn Tyr Glu Asn
                1285                1290                1295

Ala Leu Leu Ala Arg Thr Val Glu Thr Lys Leu Asn Gln Asp Ile Thr
            1300                1305                1310

Val Thr Ala Ser Gly Asp Gly Lys Ala Thr Met Thr Ile Leu Thr Phe
        1315                1320                1325

Tyr Asn Ala Gln Leu Gln Glu Lys Ala Asn Val Cys Asn Lys Phe His
    1330                1335                1340

Leu Asn Val Ser Val Glu Asn Ile His Leu Asn Ala Met Gly Ala Lys
1345                1350                1355                1360

Gly Ala Leu Met Leu Lys Ile Cys Thr Arg Tyr Leu Gly Glu Val Asp
                1365                1370                1375

Ser Thr Met Thr Ile Ile Asp Ile Ser Met Leu Thr Gly Phe Leu Pro
            1380                1385                1390

Asp Ala Glu Asp Leu Thr Arg Leu Ser Lys Gly Val Asp Arg Tyr Ile
        1395                1400                1405

Ser Arg Tyr Glu Val Asp Asn Asn Met Ala Gln Lys Val Ala Val Ile
    1410                1415                1420

Ile Tyr Leu Asn Lys Val Ser His Ser Glu Asp Glu Cys Leu His Phe
1425                1430                1435                1440

Lys Ile Leu Lys His Phe Glu Val Gly Phe Ile Gln Pro Gly Ser Val
                1445                1450                1455

Lys Val Tyr Ser Tyr Tyr Asn Leu Asp Glu Lys Cys Thr Lys Phe Tyr
            1460                1465                1470

His Pro Asp Lys Gly Thr Gly Leu Leu Asn Lys Ile Cys Ile Gly Asn
        1475                1480                1485

Val Cys Arg Cys Ala Gly Glu Thr Cys Ser Ser Leu Asn His Gln Glu
    1490                1495                1500

Arg Ile Asp Val Pro Leu Gln Ile Glu Lys Ala Cys Glu Thr Asn Val
1505                1510                1515                1520

Asp Tyr Val Tyr Lys Thr Lys Leu Leu Arg Ile Glu Glu Gln Asp Gly
                1525                1530                1535

Asn Asp Ile Tyr Val Met Asp Val Leu Glu Val Ile Lys Gln Gly Thr
            1540                1545                1550

Asp Glu Asn Pro Arg Ala Lys Thr His Gln Tyr Ile Ser Gln Arg Lys
        1555                1560                1565

Cys Gln Glu Ala Leu Asn Leu Lys Val Asn Asp Asp Tyr Leu Ile Trp
    1570                1575                1580
```

```
Gly Ser Arg Ser Asp Leu Leu Pro Thr Lys Asp Lys Ile Ser Tyr Ile
1585                1590                1595                1600

Ile Thr Lys Asn Thr Trp Ile Glu Arg Trp Pro His Glu Asp Glu Cys
            1605                1610                1615

Gln Glu Glu Glu Phe Gln Lys Leu Cys Asp Asp Phe Ala Gln Phe Ser
        1620                1625                1630

Tyr Thr Leu Thr Glu Phe Gly Cys Pro Thr
        1635                1640
```

(2) INFORMATION FOR SEQ ID NO:3:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Glu Asp Gly Phe Ile Ala Asp Ser Asp Ile
1               5                   10
```

(2) INFORMATION FOR SEQ ID NO:4:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Glu Asp Glu Leu Phe Gly Asp Asp Asn Ile
1               5                   10
```

(2) INFORMATION FOR SEQ ID NO:5:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Asp Glu Asp Ile Ile Ala Glu Glu Asn Ile
1               5                   10
```

(2) INFORMATION FOR SEQ ID NO:6:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Val Asp Arg Tyr Ile Ser Arg Tyr Glu Val Asp Asn Asn Met Ala Gln
1               5                   10                  15

Lys Val Ala Val Ile Ile Tyr Leu Asn Lys Val Ser Ser His Ser
            20                  25                  30
```

(2) INFORMATION FOR SEQ ID NO:7:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Val Asp Arg Tyr Ile Ser Lys Phe Glu Ile Asp Asn Asn Met Ala Gln
 1               5                  10                  15

Lys Gly Thr Val Val Ile Tyr Leu Asp Lys Val Ser His Ser
            20                  25                  30
```

(2) INFORMATION FOR SEQ ID NO:8:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Val Asp Arg Tyr Ile Ser Lys Tyr Glu Leu Asp Lys Ala Phe Ser Asp
 1               5                  10                  15

Arg Asn Thr Leu Ile Ile Tyr Leu Asp Lys Val Ser His Ser
            20                  25                  30
```

(2) INFORMATION FOR SEQ ID NO:9:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Leu Ile Ile Thr Pro Ser Gly Cys Gly Glu Gln Asn Met Ile Arg Met
 1               5                  10                  15

Ala Ala Pro Val Ile Ala Thr Tyr Tyr Leu
            20                  25
```

(2) INFORMATION FOR SEQ ID NO:10:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Leu Ile Ile Thr Pro Ser Gly Cys Gly Glu Gln Asn Met Ile Thr Met
 1               5                  10                  15

Thr Pro Ser Val Ile Ala Thr Tyr Tyr Leu
            20                  25
```

(2) INFORMATION FOR SEQ ID NO:11:

(i) SEQUENCE CHARACTERISTICS:
        (A) LENGTH: 26 amino acids

```
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Leu Ile Val Thr Pro Ser Gly Cys Gly Glu Gln Asn Met Ile Gly Met
    1               5                   10                  15

Thr Pro Thr Val Ile Ala Val His Tyr Leu
                20                  25

(2) INFORMATION FOR SEQ ID NO:12:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Leu Ala Arg Asp Asp Asn Glu Asp Gly Phe Ile Ala Asp Ser
    1               5                   10

(2) INFORMATION FOR SEQ ID NO:13:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Leu Ala Arg Ser Asp Phe Glu Asp Glu Leu Phe Gly Asp Asp
    1               5                   10

(2) INFORMATION FOR SEQ ID NO:14:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Leu Ala Arg Ser Asn Leu Asp Glu Asp Ile Ile Ala Glu Glu
    1               5                   10

(2) INFORMATION FOR SEQ ID NO:15:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Asp Asp Asn Glu Asp Gly Phe Ile Ala Asp Ser Asp Ile Ile Ser Arg
    1               5                   10                  15

Ser Asp Phe Pro Lys
                20
```

(2) INFORMATION FOR SEQ ID NO:16:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Ser Asp Phe Glu Asp Glu Leu Phe Gly Asp Asp Asn Ile Ile Ser Arg
1               5                   10                  15

Ser Asp Phe Pro Glu
            20
```

(2) INFORMATION FOR SEQ ID NO:17:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Ser Asn Leu Asp Glu Asp Ile Ile Ala Glu Glu Asn Ile Val Ser Arg
1               5                   10                  15

Ser Glu Phe Pro Glu
            20
```

(2) INFORMATION FOR SEQ ID NO:18:

(i) SEQUENCE CHARACTERISTICS:
        (A) LENGTH: 63 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Val Leu Met Ala Ala Ser Thr Gly Arg Asp His Trp Glu Glu Tyr Asn
1               5                   10                  15

Ala His Thr His Asn Ile Glu Gly Thr Ser Tyr Ala Leu Leu Ala Leu
                20                  25                  30

Leu Lys Met Lys Lys Phe Asp Gln Thr Gly Pro Ile Val Arg Trp Leu
            35                  40                  45

Thr Asp Gln Asn Phe Tyr Gly Glu Thr Tyr Gly Gln Thr Gln Ala
        50                  55                  60
```

(2) INFORMATION FOR SEQ ID NO:19:

(i) SEQUENCE CHARACTERISTICS:
        (A) LENGTH: 63 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Val Leu Met Ala Ala Ser Thr Gly Arg Asn Arg Trp Glu Glu Tyr Asn
1               5                   10                  15
```

```
Ala Arg Thr His Asn Ile Glu Gly Thr Ser Tyr Ala Leu Leu Ala Leu
            20                  25                  30

Leu Lys Met Lys Lys Phe Val Glu Ala Gly Pro Val Val Arg Trp Leu
        35                  40                  45

Ile Asp Gln Lys Tyr Tyr Gly Gly Thr Tyr Gly Gln Thr Gln Ala
 50                  55                  60
```

(2) INFORMATION FOR SEQ ID NO:20:

(i) SEQUENCE CHARACTERISTICS:
        (A) LENGTH: 63 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
Lys Phe Leu Thr Thr Ala Lys Asp Lys Asn Arg Trp Glu Asp Pro Gly
 1               5                  10                  15

Lys Gln Leu Tyr Asn Val Glu Ala Thr Ser Tyr Ala Leu Leu Ala Leu
            20                  25                  30

Leu Gln Leu Lys Asp Phe Asp Phe Val Pro Pro Val Val Arg Trp Leu
        35                  40                  45

Asn Glu Gln Arg Tyr Tyr Gly Gly Gly Tyr Gly Ser Thr Gln Ala
 50                  55                  60
```

(2) INFORMATION FOR SEQ ID NO:21:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
Ala Leu Tyr Thr Leu Ile Thr Pro Ala Val Leu Arg Thr Asp Thr
 1               5                  10                  15
```

(2) INFORMATION FOR SEQ ID NO:22:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
Ala Leu Tyr Thr Leu Ile Thr Pro Ala Val Leu Arg Thr Asp Thr
 1               5                  10                  15
```

(2) INFORMATION FOR SEQ ID NO:23:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Ser Pro Met Tyr Ser Ile Ile Thr Pro Asn Ile Leu Arg Leu Glu Ser
```

```
            1               5              10              15
```

(2) INFORMATION FOR SEQ ID NO:24:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

```
    Ile Pro Met Tyr Ser Ile Ile Thr Pro Asn Val Leu Arg Leu Glu Ser
    1               5                  10                  15
```

(2) INFORMATION FOR SEQ ID NO:25:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

```
    Glu Ile Gln Met Pro Thr His Lys Asp Leu Asn Leu Asp Ile Thr Ile
    1               5                  10                  15

Glu Leu Pro Asp Arg Glu Val
                    20
```

(2) INFORMATION FOR SEQ ID NO:26:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

```
    Glu Ile Gln Met Pro Thr His Gln Asp Leu Asn Leu Asp Ile Ser Ile
    1               5                  10                  15

Lys Leu Pro Glu Arg Glu Val
                    20
```

(2) INFORMATION FOR SEQ ID NO:27:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

```
    Gln Lys Asp Ala Pro Asp His Gln Glu Leu Asn Leu Asp Val Ser Leu
    1               5                  10                  15

Gln Leu Pro Ser Arg Ser Ser
                    20
```

(2) INFORMATION FOR SEQ ID NO:28:

(i) SEQUENCE CHARACTERISTICS:
        (A) LENGTH: 23 amino acids (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

Gln Thr Asp Val Pro Asp His Lys Asp Leu Asn Met Asp Val Ser Phe
   1               5                   10                  15

His Leu Pro Ser Arg Ser Ser
                20

(2) INFORMATION FOR SEQ ID NO:29:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

Asp Asp Asn Glu Asp Gly Phe Ile Ala Asp Ser Asp Ile Ile Ser Arg
   1               5                   10                  15

Ser Asp Phe Pro Lys Ser
                20

(2) INFORMATION FOR SEQ ID NO:30:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

Ser Asp Phe Glu Asp Glu Leu Phe Gly Asp Asp Asn Ile Ile Ser Arg
   1               5                   10                  15

Ser Asp Phe Pro Glu Ser
                20

(2) INFORMATION FOR SEQ ID NO:31:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:31:

Ser Asn Leu Asp Glu Asp Ile Ile Ala Glu Glu Asn Ile Val Ser Arg
   1               5                   10                  15

Ser Glu Phe Pro Glu Ser
                20

(2) INFORMATION FOR SEQ ID NO:32:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:32:

```
Ser Glu Leu Glu Glu Asp Ile Ile Pro Glu Glu Asp Ile Ile Ser Arg
1               5                   10                  15

Ser His Phe Pro Gln Ser
            20
```

(2) INFORMATION FOR SEQ ID NO:33:

(i) SEQUENCE CHARACTERISTICS:
      (A) LENGTH: 4138 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:33:

```
GAATTCCATC AGGAGGTGAT ATGGTAATGA CTGAGCAAAG TGGCATTCAT ATTGTGACAT      60
CTCCCTATCA GATCTACTTC ACAAAAACCC CAAATATTT CAAGCCAGGA ATGCCATATG      120
AACTGACGGT GTATGTTACC AAACCTGATG GCTCACCAGC TGCCCATGTG CCAGTGGTAT     180
CAGAGGCCAT TCATTCTGAG GGAACCACTT TGAGTGATGG GACTGCTAAG CTCTTCCTGA     240
ACACACCACA AAATGCTCAA AGCCTACCGA TCACTGTTAG AACTAACCAT GGAGACCTCC     300
CAAGAGAACG CCAGGCAATA AAGTCCATGA CAGCCACAGC CTACCAAACC CAGGGAGGAT     360
CTGGAAACTA TCTTCATGTA GCCATTACAT CTACAGAGAT TAAGCCCGGA GATAACTTAC     420
CTGTCAATTT CAATGTGAGG GGCAATGCAA ATTCACTGAA CCAGATCAAA TATTTCACAT     480
ACCTCATACT GAATAAAGGG AAGATTTTCA AGGTTGGCAG GCAACACAGG GGAGATGGGG     540
AGAATCTGGT GACCATGAAT CTACATATCA CTCCAGATCT CATTCCTTCC TTCCGGTTTG     600
TGGCTTACTA CCAAGTGGGA ACAATGAAA TTGTGGCTGA TTCTGTCTGG GTGGATGTGA     660
AGGATACCTG CATGGGAACG TTGGTTGTGA AAGGAGCGAC TTCCAGAGAC AATCGAATAC     720
AAATGCCAGG AGCTGCAATG AAAATCAAAT TGGAAGGGGA TCCAGGTGCT TGGATTGGTC     780
TTGTGGCTGT GGACAAAGCA GAATATGTTC TCAATGATAA ATATAAGATT AGCCAAGCTA     840
AGATATGGGA CACAATAGAA AAGAGTGACT TTGGCTGTAC AGCTGGCAGT GGCCAGAATA     900
ATCTGGGTGT GTTTGAAGAT GCTGGACTGG CTCTGACAAC CAGCACTAAT CTCAACACCA     960
AACAGAGATC AGCTGCAAAG TGTCCTCAGC CTGCAAATCG GAGGCGTCGC AGTTCTGTTT     1020
TGCTGCTTGA CAGCAACGCA AGCAAAGCGG CACAGTTTCA GGATCAAGAC CTGCGTAAAT     1080
GCTGTGAAGA TGGCATGCAT GAGAACCCCA TGGGGCACAC TTGTGAAAAG CGTGAAAAAT     1140
ACATCCAGGA GGGAGATGCT TGTAAGGCTG CCTTCCTCGA ATGCTGTCAC TACATCAAAG     1200
GGATCCAAGA TGACAATAAA CGGGAGAGCG AGTTGTTTCT GGCAAGAAGT GATTTTGAAG     1260
ATGATTTATT TGGAGAAGGT AACATCACCT CAAGGTCTGA TTTTCCTGAG AGTTGGTTGT     1320
GGCTAATGGA GCAGCTGTCT GAACATCCTA ACAGTAAAGG GATTTCAAGC AAGATAGTAC     1380
CTTTTTATCT GAGGGATTCC ATCACAACCT GGGAGTTGCT GGCTGTGGGC CTTTCACCCA     1440
CCAAAGGGAT CTGTGTGGCT GAACCTTATG AAATAACAGT CATGAAAGAC TTCTTCATTG     1500
ATCTTCAACT GCCGTATTCA GTAGTGAAGA ATGAGCAGGT GAAAATTCGA GCTGTTTTGT     1560
ACAACTACGC TGACAAGGAT ATTTATGTAC GAGTGGAACT GTTATACAGC CCAGCCTTCT     1620
GCAGTGCTTC CACAGAAAGT CAAAGATACC GAGAGCAGTT GCCAATTAAA GCCCTGTCCT     1680
CCAGGGCAGT ATCGTTTGTG ATAGTCCCAT TAGAGCAAGG ATTGCATGAT GTTGAGGTTA     1740
```

```
CAGCAAGTGT CCAGGGAGAG TTGATGTCAG ATGGTGTGAA GAAGAAACTG AAAGTTGTAC   1800

CTGAAGGGGA ATGGAAAAGT ATTGTTACTA TTATTGAACT GGACCCACAT ACAAAAGGAA   1860

TTGGTGGAAC ACAGGTAGAA TTGGTCAAAG CCAATAAATT AAATGACAGG GTTCCTGATA   1920

CGGAAATAGA AACCAAGATT ACTATTCAAG GTGATCCTGT GGCTCAGACT ATTGAAAACT   1980

CAATTGATGG AAGTAAACTC AACCATCTCA TTATCACTCC TTTTGGCTGT GGGGAGCAAA   2040

ATATGATCCG CATGACTGCA CCAGTTATTG CCACCTACTA CCTGGACACC ACACAGCAGT   2100

GGGAGACTCT CGGCATAAAT CGCAGGACTG AAGCTGTCAA TCAGATCATG ACTGGTTATG   2160

CCCAGCAGTT GGTGTACAAG AAAGCAGACC ATTCCTATGC AGCATTTACA AACAGTGCAT   2220

CTAGTTCTTG GCTAACAGCA TATGTTGTAA AAATCTTTGC CTTGGCTGCC AAAATTGTAA   2280

AAGACATTAA CCATGAAATC GTTTGTGGAG GTATGAGGTG GCTGATTCTG AACAGGCAAC   2340

GAACAGATGG AGTGTTCAGA GAAAACGCCC CTGTACTTTT TGGAACAATG CAGGGAGGCA   2400

TTCAAGGTGC TGAACCAGAA GGATCTTTAA CAGCTTTCAT TCTGGTTGCG TTGTTGGAAT   2460

CCAGATCAAT CTGCAATGCA TATATCAATA TTCTAGACAG CAGCATCAGT AAGGCCACAG   2520

ATTATTTACT CAAAAAGTAT GAGAAACTGC AAAGGCCTTA CACTACAGCC CTCACAGCCT   2580

ATGCTTTGGC TGCTGCAGAA CGACTCAATG ATGACAGGGT ACTCATGGCA GCATCAACAG   2640

GAAGGAATCG TTGGGAAGAA CCTAACGCCC ACACCCATAA CATTGAAGGC ACTTCCTATG   2700

CCTTGTTGGC CCTGCTGAAA ATGAAGAAAT TTGTTGAGGC CGGTCCTGTA GTCCAATGGC   2760

TGATAGATCA GCAATATTAT GGGGGAACAT ATGGACAAAC CCAAGCAACA GTTATGATGT   2820

TTCAAGCTCT TGCTGAATAT GAGATTCAGA TGCCTACCCA TAAGGACTTA AACTTAGATA   2880

TTACTATTGA ACTGCCAGAT CGAGAAGTAC CTATAAGGTA CAGAATTAAT TATGAAAATG   2940

CTCTCCTGGC TCAGACAGTA GAGACCAAAC TCAACGAAGA CTTCACTGTG TCAGCATCAG   3000

GTGATGGAAA AGCAACAATG ACCATTTTGA CGGTCTATAA TGCACAATTG AGGGAGGATG   3060

CAAATGTTTG CAACAAATTC CATCTTGATG TTTCTGTTGA AAACGTCCAG TTGAACTTAA   3120

AAGAGGCAAA GGGAGCCAAG GGAGCCCTCA AGCTCAAAAT CTGCACTAGG TATCTGGGAG   3180

AAGTTGATTC TACAATGACA ATAATTGATG TTTCTATGCT GACTGGTTTT GTCCCTGATA   3240

CTGAAGACCT TACGAGGCTT TCTAAAGGAG TCGACAGATA TATCTCCATG TTTGAAATTA   3300

ACAATAATAT GGCTCAGAAA GGAACTGTTA TCATTTACTT AGACAAGGTC TCCCACTCTG   3360

AAGATGAATG CCTGCACTTT AAGATTCTCA AGCATTTTGA AGTTGGCTTC ATTCAGCCAG   3420

GATCAGTCAA GGTGTACAGC TACTACAATC TAGATGAAAA ATGTACCAAG ATCTACCATC   3480

CAGATGAAGC AACAGGCCTT CTCAATAAGA TATGTGTTGG TAACGTTTGC CGATGTGCAG   3540

AAGAAACCTG TTCCTTGCTC AACCAGCAGA AGAATGTTAC TCGGCAATTG CGAATTCAGA   3600

AAGCTTCGA TCCAAATGTG GATTATGTCT ATAAAACCAA GCTGCTTCGA ATAGAAGAAA   3660

AAGATGGTAA TGATATCTAT GTCATGGACG TTTTAGAAGT TCTTAAACAA GGCACTGACC   3720

AAAATCAACA AGTAAAGGTC CGCCAGTATG TAAGTCAAAG GAAATGCCAG GAGGCTTTGA   3780

ATCTGATGGT GAATAATGAT TATCTGATCT GGGGTCCAAG CAGTGACCTG TGGCCCATGA   3840

AAGATAAAAT TTCCTATCTC ATTACAAAGA ACACCTGGAT TGAGAGATGG CCACATGAAG   3900

ACAAATGTCA GGAAGAAGAA TTCCAAAAGT TGTGTGATGA CTTTGCTCTG TTTAGCTACG   3960

CAATGAGTTT GCTGCCCTAC TTAAAAGTTC AGAATAATCA ATGATAGGAA GGAAATTCTC   4020

AGAAGACAGA TTTTTGAGCC AATACATATA TGTTACTTTG TCTCTTAATT TTTTAGTTTT   4080

CTGTCATTTG CTGTGCTGTT TTCCCTTAAA TTGTTTATAC ATAGAATAAA TGGAATTC    4138
```

(2) INFORMATION FOR SEQ ID NO:34:

(i) SEQUENCE CHARACTERISTICS:
        (A) LENGTH: 1333 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:34:

```
Ile Pro Ser Gly Gly Asp Met Val Met Thr Glu Gln Ser Gly Ile His
 1               5                  10                  15

Ile Val Thr Ser Pro Tyr Gln Ile Tyr Phe Thr Lys Thr Pro Lys Tyr
                20                  25                  30

Phe Lys Pro Gly Met Pro Tyr Glu Leu Thr Val Tyr Val Thr Lys Pro
            35                  40                  45

Asp Gly Ser Pro Ala Ala His Val Pro Val Val Ser Glu Ala Ile His
 50                  55                  60

Ser Glu Gly Thr Thr Leu Ser Asp Gly Thr Ala Lys Leu Phe Leu Asn
 65                  70                  75                  80

Thr Pro Gln Asn Ala Gln Ser Leu Pro Ile Thr Val Arg Thr Asn His
                85                  90                  95

Gly Asp Leu Pro Arg Glu Arg Gln Ala Ile Lys Ser Met Thr Ala Thr
            100                 105                 110

Ala Tyr Gln Thr Gln Gly Gly Ser Gly Asn Tyr Leu His Val Ala Ile
            115                 120                 125

Thr Ser Thr Glu Ile Lys Pro Gly Asp Asn Leu Pro Val Asn Phe Asn
130                 135                 140

Val Arg Gly Asn Ala Asn Ser Leu Asn Gln Ile Lys Tyr Phe Thr Tyr
145                 150                 155                 160

Leu Ile Leu Asn Lys Gly Lys Ile Phe Lys Val Gly Arg Gln His Arg
                165                 170                 175

Gly Asp Gly Asn Leu Val Thr Met Asn Leu His Ile Thr Pro Asp Leu
            180                 185                 190

Ile Pro Ser Phe Arg Phe Val Ala Tyr Tyr Gln Val Gly Asn Asn Glu
            195                 200                 205

Ile Glu Val Ala Asp Ser Val Trp Val Asp Val Lys Asp Thr Cys Met
210                 215                 220

Gly Thr Leu Val Val Lys Gly Ala Thr Ser Arg Asp Asn Arg Ile Gln
225                 230                 235                 240

Met Pro Gly Ala Ala Met Lys Ile Lys Leu Glu Gly Asp Pro Gly Ala
                245                 250                 255

Trp Ile Gly Leu Val Ala Val Asp Lys Ala Glu Tyr Val Leu Asn Asp
            260                 265                 270

Lys Tyr Lys Ile Ser Gln Ala Lys Ile Trp Asp Thr Ile Glu Lys Ser
            275                 280                 285

Asp Phe Gly Cys Thr Ala Gly Ser Gly Gln Asn Asn Leu Gly Val Phe
            290                 295                 300

Glu Asp Ala Gly Leu Ala Leu Thr Thr Ser Thr Asn Leu Asn Thr Lys
305                 310                 315                 320

Gln Arg Ser Ala Ala Lys Cys Pro Gln Pro Ala Asn Arg Arg Arg Arg
                325                 330                 335

Ser Ser Val Leu Leu Leu Asp Ser Asn Ala Ser Lys Ala Ala Gln Phe
            340                 345                 350
```

```
Gln Asp Gln Asp Leu Arg Lys Cys Cys Glu Asp Gly Met His Glu Asn
        355                 360                 365
Pro Met Gly His Thr Cys Glu Lys Arg Glu Lys Tyr Ile Gln Glu Gly
        370                 375                 380
Asp Ala Cys Lys Ala Ala Phe Leu Glu Cys His Tyr Ile Lys Gly
385                 390                 395                 400
Ile Gln Asp Asp Asn Lys Arg Glu Ser Glu Leu Phe Leu Ala Arg Ser
                405                 410                 415
Asp Phe Glu Asp Asp Leu Phe Gly Gly Asn Ile Thr Ser Arg Ser
                420                 425                 430
Asp Phe Pro Glu Ser Trp Leu Trp Leu Met Glu Gln Leu Ser Glu His
            435                 440                 445
Pro Asn Ser Lys Gly Ile Ser Ser Lys Ile Val Pro Phe Tyr Leu Arg
        450                 455                 460
Asp Ser Ile Thr Thr Trp Glu Leu Leu Ala Val Gly Leu Ser Pro Thr
465                 470                 475                 480
Lys Gly Ile Cys Val Ala Glu Pro Tyr Glu Ile Thr Val Met Lys Asp
                485                 490                 495
Phe Phe Ile Asp Leu Gln Leu Pro Tyr Ser Val Val Lys Asn Glu Gln
                500                 505                 510
Val Lys Ile Arg Ala Val Leu Tyr Asn Tyr Ala Asp Lys Asp Ile Tyr
            515                 520                 525
Val Arg Val Glu Leu Leu Tyr Ser Pro Ala Phe Cys Ser Ala Ser Thr
            530                 535                 540
Glu Ser Gln Arg Tyr Arg Glu Gln Leu Pro Ile Lys Ala Leu Ser Ser
545                 550                 555                 560
Arg Ala Val Ser Phe Val Ile Val Pro Leu Glu Gln Gly Leu His Asp
                565                 570                 575
Val Glu Val Thr Ala Ser Val Gln Gly Glu Leu Met Ser Asp Gly Val
                580                 585                 590
Lys Lys Lys Leu Lys Val Val Pro Glu Gly Glu Trp Lys Ser Ile Val
            595                 600                 605
Thr Ile Ile Glu Leu Asp Pro His Thr Lys Gly Ile Gly Gly Thr Gln
        610                 615                 620
Val Glu Leu Val Lys Ala Asn Lys Leu Asn Asp Arg Val Pro Asp Thr
625                 630                 635                 640
Glu Ile Glu Thr Lys Ile Thr Ile Gln Gly Asp Pro Val Ala Gln Thr
                645                 650                 655
Ile Glu Asn Ser Ile Asp Gly Ser Lys Leu Asn His Leu Ile Ile Thr
                660                 665                 670
Pro Phe Gly Cys Gly Glu Gln Asn Met Ile Arg Met Thr Ala Pro Val
            675                 680                 685
Ile Ala Thr Tyr Tyr Leu Asp Thr Thr Gln Gln Trp Glu Thr Leu Gly
        690                 695                 700
Ile Asn Arg Arg Thr Glu Ala Val Asn Gln Ile Met Thr Gly Tyr Ala
705                 710                 715                 720
Gln Gln Leu Val Tyr Lys Lys Ala Asp His Ser Tyr Ala Ala Phe Thr
                725                 730                 735
Asn Ser Ala Ser Ser Ser Trp Leu Thr Ala Tyr Val Val Lys Ile Phe
            740                 745                 750
Ala Leu Ala Ala Lys Ile Val Lys Asp Ile Asn His Glu Ile Val Cys
        755                 760                 765
Gly Gly Met Arg Trp Leu Ile Leu Asn Arg Gln Arg Thr Asp Gly Val
        770                 775                 780
```

-continued

```
Phe Arg Glu Asn Ala Pro Val Leu Phe Gly Thr Met Gln Gly Gly Ile
785                 790                 795                 800

Gln Gly Ala Glu Pro Glu Gly Ser Leu Thr Ala Phe Ile Leu Val Ala
            805                 810                 815

Leu Leu Glu Ser Arg Ser Ile Cys Asn Ala Tyr Ile Asn Ile Leu Asp
            820                 825                 830

Ser Ser Ile Ser Lys Ala Thr Asp Tyr Leu Leu Lys Lys Tyr Glu Lys
            835                 840                 845

Leu Gln Arg Pro Tyr Thr Thr Ala Leu Thr Ala Tyr Ala Leu Ala Ala
850                 855                 860

Ala Glu Arg Leu Asn Asp Asp Arg Val Leu Met Ala Ala Ser Thr Gly
865                 870                 875                 880

Arg Asn Arg Trp Glu Glu Pro Asn Ala His Thr His Asn Ile Glu Gly
                885                 890                 895

Thr Ser Tyr Ala Leu Leu Ala Leu Leu Lys Met Lys Lys Phe Val Glu
            900                 905                 910

Ala Gly Pro Val Val Gln Trp Leu Ile Asp Gln Gln Tyr Tyr Gly Gly
            915                 920                 925

Thr Tyr Gly Gln Thr Gln Ala Thr Val Met Met Phe Gln Ala Leu Ala
            930                 935                 940

Glu Tyr Glu Ile Gln Met Pro Thr His Lys Asp Leu Asn Leu Asp Ile
945                 950                 955                 960

Thr Ile Glu Leu Pro Asp Arg Glu Val Pro Ile Arg Tyr Arg Ile Asn
                965                 970                 975

Tyr Glu Asn Ala Leu Leu Ala Gln Thr Val Glu Thr Lys Leu Asn Glu
            980                 985                 990

Asp Phe Thr Val Ser Ala Ser Gly Asp Gly Lys Ala Thr Met Thr Ile
            995                 1000                1005

Leu Thr Val Tyr Asn Ala Gln Leu Arg Glu Asp Ala Asn Val Cys Asn
            1010                1015                1020

Lys Phe His Leu Asp Val Ser Val Glu Asn Val Gln Leu Asn Leu Lys
1025                1030                1035                1040

Glu Ala Lys Gly Ala Lys Gly Ala Leu Lys Leu Lys Ile Cys Thr Arg
                1045                1050                1055

Tyr Leu Gly Glu Val Asp Ser Thr Met Thr Ile Ile Asp Val Ser Met
            1060                1065                1070

Leu Thr Gly Phe Val Pro Asp Thr Glu Asp Leu Thr Arg Leu Ser Lys
            1075                1080                1085

Gly Val Asp Arg Tyr Ile Ser Met Phe Glu Ile Asn Asn Asn Met Ala
            1090                1095                1100

Gln Lys Gly Thr Val Ile Ile Tyr Leu Asp Lys Val Ser His Ser Glu
1105                1110                1115                1120

Asp Glu Cys Leu His Phe Lys Ile Leu Lys His Phe Glu Val Gly Phe
                1125                1130                1135

Ile Gln Pro Gly Ser Val Lys Val Tyr Ser Tyr Tyr Asn Leu Asp Glu
            1140                1145                1150

Lys Cys Thr Lys Ile Tyr His Pro Asp Glu Ala Thr Gly Leu Leu Asn
            1155                1160                1165

Lys Ile Cys Val Gly Asn Val Cys Arg Cys Ala Glu Glu Thr Cys Ser
            1170                1175                1180

Leu Leu Asn Gln Gln Lys Asn Val Thr Arg Gln Leu Arg Ile Gln Lys
1185                1190                1195                1200

Ala Phe Asp Pro Asn Val Asp Tyr Val Tyr Lys Thr Lys Leu Leu Arg
```

```
                       1205                  1210                  1215

Ile Glu Glu Lys Asp Gly Asn Asp Ile Tyr Val Met Asp Val Leu Glu
                   1220                 1225                 1230

Val Leu Lys Gln Gly Thr Asp Gln Asn Gln Gln Val Lys Val Arg Gln
                   1235                 1240                 1245

Tyr Val Ser Gln Arg Lys Cys Gln Glu Ala Leu Asn Leu Met Val Asn
                   1250                 1255                 1260

Asn Asp Tyr Leu Ile Trp Gly Pro Ser Ser Asp Leu Trp Pro Met Lys
    1265                 1270                 1275                 1280

Asp Lys Ile Ser Tyr Leu Ile Thr Lys Asn Thr Trp Ile Glu Arg Trp
                   1285                 1290                 1295

Pro His Glu Asp Lys Cys Gln Glu Glu Glu Phe Gln Lys Leu Cys Asp
                   1300                 1305                 1310

Asp Phe Ala Leu Phe Ser Tyr Ala Met Ser Leu Leu Pro Tyr Leu Lys
                   1315                 1320                 1325

Val Gln Asn Asn Gln
                   1330

(2) INFORMATION FOR SEQ ID NO:35:

(i) SEQUENCE CHARACTERISTICS:
        (A) LENGTH: 1648 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:35:

Met Glu Arg Met Ala Leu Tyr Leu Val Ala Ala Leu Leu Ile Gly Phe
    1               5                  10                  15

Pro Gly Ser Ser His Gly Ala Leu Tyr Thr Leu Ile Thr Pro Ala Val
                   20                  25                  30

Leu Arg Thr Asp Thr Glu Glu Gln Ile Leu Val Glu Ala His Gly Asp
                   35                  40                  45

Ser Thr Pro Lys Gln Leu Asp Ile Phe Val His Asp Phe Pro Arg Lys
               50                  55                  60

Gln Lys Thr Leu Phe Gln Thr Arg Val Asp Met Asn Pro Ala Gly Gly
    65                  70                  75                  80

Met Leu Val Thr Pro Thr Ile Glu Ile Pro Ala Lys Glu Val Ser Thr
                   85                  90                  95

Asp Ser Arg Gln Asn Gln Tyr Val Val Gln Val Thr Gly Pro Gln
                   100                 105                 110

Val Arg Leu Glu Lys Val Val Leu Leu Ser Tyr Gln Ser Ser Phe Leu
                   115                 120                 125

Phe Ile Gln Thr Asp Lys Gly Ile Tyr Thr Pro Gly Ser Pro Val Leu
    130                 135                 140

Tyr Arg Val Phe Ser Met Asp His His Thr Ser Lys Met Asn Lys Thr
    145                 150                 155                 160

Val Ile Val Glu Phe Gln Thr Pro Glu Gly Ile Leu Val Ser Ser Asn
                   165                 170                 175

Ser Val Asp Leu Asn Phe Phe Trp Pro Tyr Asn Leu Pro Asp Leu Val
                   180                 185                 190

Ser Leu Gly Thr Trp Arg Ile Val Ala Lys Tyr Glu His Ser Pro Glu
                   195                 200                 205

Asn Tyr Thr Ala Tyr Phe Asp Val Arg Lys Tyr Val Leu Pro Ser Phe
    210                 215                 220
```

```
Glu Val Arg Leu Gln Pro Ser Glu Lys Phe Phe Tyr Ile Asp Gly Asn
225                 230                 235                 240

Glu Asn Phe His Val Ser Ile Thr Ala Arg Tyr Leu Tyr Gly Glu Glu
            245                 250                 255

Val Glu Gly Val Ala Phe Val Leu Phe Gly Val Lys Ile Asp Asp Ala
            260                 265                 270

Lys Lys Ser Ile Pro Asp Ser Leu Thr Arg Ile Pro Ile Ile Asp Gly
        275                 280                 285

Asp Gly Lys Ala Thr Leu Lys Arg Asp Thr Phe Arg Ser Arg Phe Pro
    290                 295                 300

Asn Leu Asn Glu Leu Val Gly His Thr Leu Tyr Ala Ser Val Thr Val
305                 310                 315                 320

Met Thr Glu Ser Gly Ser Asp Met Val Val Thr Glu Gln Ser Gly Ile
            325                 330                 335

His Ile Val Ala Ser Pro Tyr Gln Ile His Phe Thr Lys Thr Pro Lys
            340                 345                 350

Tyr Phe Lys Pro Gly Met Pro Tyr Glu Leu Thr Val Tyr Val Thr Asn
        355                 360                 365

Pro Asp Gly Ser Pro Ala Ala His Val Pro Val Val Ser Glu Ala Phe
    370                 375                 380

His Ser Met Gly Thr Thr Leu Ser Asp Gly Thr Ala Lys Leu Ile Leu
385                 390                 395                 400

Asn Ile Pro Leu Asn Ala Gln Ser Leu Pro Ile Thr Val Arg Thr Asn
            405                 410                 415

His Gly Asp Leu Pro Arg Glu Arg Gln Ala Thr Lys Ser Met Thr Ala
            420                 425                 430

Ile Ala Tyr Gln Thr Gln Gly Gly Ser Gly Asn Tyr Leu His Val Ala
        435                 440                 445

Ile Thr Ser Thr Glu Ile Lys Pro Gly Asp Asn Leu Pro Val Asn Phe
    450                 455                 460

Asn Val Lys Gly Asn Ala Asn Ser Leu Lys Gln Ile Lys Tyr Phe Thr
465                 470                 475                 480

Tyr Leu Ile Leu Asn Lys Gly Lys Ile Phe Lys Val Gly Arg Gln Pro
            485                 490                 495

Arg Arg Asp Gly Gln Asn Leu Val Thr Met Asn Leu His Ile Thr Pro
            500                 505                 510

Asp Leu Ile Pro Ser Pro Arg Phe Val Ala Tyr Tyr Gln Val Gly Asn
        515                 520                 525

Asn Glu Ile Val Ala Asp Ser Val Trp Val Asp Val Lys Asp Thr Cys
    530                 535                 540

Met Gly Thr Leu Val Val Lys Gly Asp Asn Leu Ile Gln Met Pro Gly
545                 550                 555                 560

Ala Ala Met Lys Ile Lys Leu Glu Gly Asp Phe Gly Ala Arg Val Gly
            565                 570                 575

Leu Val Ala Val Asp Lys Ala Val Tyr Val Leu Asn Asp Lys Tyr Lys
            580                 585                 590

Ile Ser Gln Ala Lys Ile Trp Asp Thr Ile Glu Lys Ser Asp Phe Gly
        595                 600                 605

Cys Thr Ala Gly Ser Gly Gln Asn Asn Leu Gly Val Phe Glu Asp Ala
    610                 615                 620

Gly Leu Ala Leu Thr Thr Ser Thr Asn Leu Asn Thr Lys Gln Arg Ser
625                 630                 635                 640

Ala Ala Lys Cys Pro Gln Pro Ala Asn Arg Arg Arg Arg Ser Ser Val
```

```
                    645                 650                 655
    Leu Leu Leu Asp Ser Asn Ala Ser Lys Ala Ala Glu Phe Gln Asp Gln
                    660                 665                 670
    Asp Leu Arg Lys Cys Cys Glu Asp Val Met His Glu Asn Pro Met Gly
                    675                 680                 685
    Tyr Thr Cys Glu Lys Arg Ala Lys Tyr Ile Gln Glu Gly Asp Ala Cys
                    690                 695                 700
    Lys Ala Ala Phe Leu Glu Cys Cys Arg Tyr Ile Lys Gly Val Arg Asp
    705                 710                 715                 720
    Glu Asn Gln Arg Glu Ser Glu Leu Phe Leu Ala Arg Asp Asp Asn Glu
                    725                 730                 735
    Asp Gly Phe Ile Ala Asp Ser Asp Ile Ile Ser Arg Ser Asp Phe Pro
                    740                 745                 750
    Lys Trp Trp Leu Trp Leu Thr Lys Asp Leu Thr Glu Glu Pro Asn Ser
                    755                 760                 765
    Gln Gly Ile Ser Ser Lys Thr Met Ser Phe Tyr Leu Arg Asp Ser Ile
                    770                 775                 780
    Thr Thr Trp Val Val Leu Ala Val Ser Phe Thr Pro Thr Lys Gly Ile
    785                 790                 795                 800
    Cys Val Ala Glu Pro Tyr Glu Ile Arg Val Met Lys Val Phe Phe Ile
                    805                 810                 815
    Asp Leu Gln Met Pro Tyr Ser Val Val Lys Asn Glu Gln Val Glu Ile
                    820                 825                 830
    Arg Ala Ile Leu His Asn Tyr Val Asn Glu Asp Ile Tyr Val Arg Val
                    835                 840                 845
    Glu Leu Leu Tyr Asn Pro Ala Phe Cys Ser Ala Ser Thr Lys Gly Gln
                    850                 855                 860
    Arg Tyr Arg Gln Gln Pro Ile Lys Ala Leu Ser Ser Arg Ala Val
    865                 870                 875                 880
    Pro Phe Val Ile Val Pro Leu Glu Gln Gly Leu His Asp Val Glu Ile
                    885                 890                 895
    Lys Ala Ser Val Gln Glu Ala Leu Trp Ser Asp Gly Val Arg Lys Lys
                    900                 905                 910
    Leu Lys Val Val Pro Glu Gly Val Gln Lys Ser Ile Val Thr Ile Val
                    915                 920                 925
    Lys Leu Asp Pro Arg Ala Lys Gly Val Gly Gly Thr Gln Leu Glu Val
                    930                 935                 940
    Ile Lys Ala Arg Lys Leu Asp Asp Arg Val Pro Asp Thr Glu Ile Glu
    945                 950                 955                 960
    Thr Lys Ile Ile Ile Gln Gly Asp Pro Val Ala Gln Ile Ile Glu Asn
                    965                 970                 975
    Ser Ile Asp Gly Ser Lys Leu Asn His Leu Ile Ile Thr Pro Ser Gly
                    980                 985                 990
    Cys Gly Glu Gln Asn Met Ile Arg Met Ala Ala Pro Val Ile Ala Thr
                    995                 1000                1005
    Tyr Tyr Leu Asp Thr Thr Glu Gln Trp Glu Thr Leu Gly Ile Asn Arg
                    1010                1015                1020
    Arg Thr Glu Ala Val Asn Gln Ile Val Thr Gly Tyr Ala Gln Gln Met
    1025                1030                1035                1040
    Val Tyr Lys Lys Ala Asp His Ser Tyr Ala Ala Phe Thr Asn Arg Ala
                    1045                1050                1055
    Ser Ser Ser Trp Leu Thr Ala Tyr Val Val Lys Val Phe Ala Met Ala
                    1060                1065                1070
```

-continued

```
Ala Lys Met Val Ala Gly Ile Ser His Glu Ile Ile Cys Gly Gly Val
    1075                1080                1085

Arg Trp Leu Ile Leu Asn Arg Gln Gln Pro Asp Gly Ala Phe Lys Glu
    1090                1095                1100

Asn Ala Pro Val Leu Ser Gly Thr Met Gln Gly Ile Gln Gly Ala
1105                1110                1115                1120

Glu Glu Glu Val Tyr Leu Thr Ala Phe Ile Leu Val Ala Leu Leu Glu
                1125                1130                1135

Ser Lys Thr Ile Cys Asn Asp Tyr Val Asn Ser Leu Asp Ser Ser Ile
                1140                1145                1150

Lys Lys Ala Thr Asn Tyr Leu Leu Lys Lys Tyr Glu Lys Leu Gln Arg
                1155                1160                1165

Pro Tyr Thr Thr Ala Leu Thr Ala Tyr Ala Leu Ala Ala Ala Asp Gln
    1170                1175                1180

Leu Asn Asp Asp Arg Val Leu Met Ala Ala Ser Thr Gly Arg Asp His
1185                1190                1195                1200

Trp Glu Glu Tyr Asn Ala His Thr His Asn Ile Glu Gly Thr Ser Tyr
                1205                1210                1215

Ala Leu Leu Ala Leu Leu Lys Met Lys Lys Phe Asp Gln Thr Gly Pro
                1220                1225                1230

Ile Val Arg Trp Leu Thr Asp Gln Asn Phe Tyr Gly Glu Thr Tyr Gly
                1235                1240                1245

Gln Thr Gln Ala Thr Val Met Ala Phe Gln Ala Leu Ala Glu Tyr Glu
    1250                1255                1260

Ile Gln Met Pro Thr His Lys Asp Leu Asn Leu Asp Ile Thr Ile Glu
1265                1270                1275                1280

Leu Pro Asp Arg Glu Val Pro Ile Arg Tyr Arg Ile Asn Tyr Glu Asn
                1285                1290                1295

Ala Leu Leu Ala Arg Thr Val Glu Thr Lys Leu Asn Gln Asp Ile Thr
                1300                1305                1310

Val Thr Ala Ser Gly Asp Gly Lys Ala Thr Met Thr Ile Leu Thr Phe
                1315                1320                1325

Tyr Asn Ala Gln Leu Gln Glu Lys Ala Asn Val Cys Asn Lys Phe His
    1330                1335                1340

Leu Asn Val Ser Val Glu Asn Ile His Leu Asn Ala Met Gly Ala Lys
1345                1350                1355                1360

Gly Ala Leu Met Leu Lys Ile Cys Thr Arg Tyr Leu Gly Glu Val Asp
                1365                1370                1375

Ser Thr Met Thr Ile Ile Asp Ile Ser Met Leu Thr Gly Phe Leu Pro
                1380                1385                1390

Asp Ala Glu Asp Leu Thr Arg Leu Ser Lys Gly Val Asp Arg Tyr Ile
                1395                1400                1405

Ser Arg Tyr Glu Val Asp Asn Asn Met Ala Gln Lys Val Ala Val Ile
    1410                1415                1420

Ile Tyr Leu Asn Lys Val Ser His Ser Glu Asp Glu Cys Leu His Pro
1425                1430                1435                1440

Lys Ile Leu Lys His Phe Glu Val Gly Phe Ile Gln Pro Gly Ser Val
                1445                1450                1455

Lys Val Tyr Ser Tyr Tyr Asn Leu Asp Glu Lys Cys Thr Lys Phe Tyr
                1460                1465                1470

His Pro Asp Lys Gly Thr Gly Leu Leu Asn Lys Ile Cys Ile Gly Asn
                1475                1480                1485

Val Cys Arg Cys Ala Gly Glu Thr Cys Ser Ser Leu Asn His Gln Glu
    1490                1495                1500
```

```
Arg Ile Asp Val Pro Leu Gln Ile Glu Lys Ala Cys Glu Thr Asn Val
1505                1510                1515                1520

Asp Tyr Val Tyr Lys Thr Lys Leu Leu Arg Ile Glu Glu Gln Asp Gly
            1525                1530                1535

Asn Asp Ile Tyr Val Met Asp Val Leu Glu Val Ile Lys Gln Gly Thr
        1540                1545                1550

Asp Glu Asn Pro Arg Ala Lys Thr His Gln Tyr Ile Ser Gln Arg Lys
    1555                1560                1565

Cys Gln Glu Ala Leu Asn Leu Lys Val Asn Asp Asp Tyr Leu Ile Trp
1570                1575                1580

Gly Ser Arg Ser Asp Leu Leu Pro Thr Lys Asp Lys Ile Ser Tyr Ile
1585                1590                1595                1600

Ile Thr Lys Asn Thr Trp Ile Glu Arg Trp Pro His Glu Asp Glu Cys
                1605                1610                1615

Gln Glu Glu Glu Phe Gln Lys Leu Cys Asp Asp Phe Ala Gln Phe Ser
            1620                1625                1630

Tyr Thr Leu Thr Glu Phe Gly Cys Pro Thr His His His His His His
        1635                1640                1645
```

(2) INFORMATION FOR SEQ ID NO:36:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

```
Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala
            35
```

(2) INFORMATION FOR SEQ ID NO:37:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

```
Met Arg Gly Ser His His His His His His Gly Met Ala Ser Met Thr
1               5                   10                  15

Gly Gly Gln Gln Met Gly Arg Asp Leu Tyr Asn Asn Asn Asn Lys
            20                  25                  30
```

(2) INFORMATION FOR SEQ ID NO:38:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA PRIMER"

(xi) SEQUENCE DESCRIPTION: SEQ ID NO:38:

GAGGAATTCA AGGTGC                                                               16

(2) INFORMATION FOR SEQ ID NO:39:

(i) SEQUENCE CHARACTERISTICS:
      (A) LENGTH: 57 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "SYNTHETIC DNA PRIMER"

(xi) SEQUENCE DESCRIPTION: SEQ ID NO:39:

AAGTTTAGCG GCCGCTTAAT GATGATGATG ATGATGAGTA GGGCAGCCAA ACTCAGT      57

RECOMBINANT PROCVF

BACKGROUND OF THE INVENTION

Field of the Invention

The present invention relates to recombinant pro-cobra venom factor (proCVF), DNA encoding recombinant proCVF, plasmids comprising such DNA, and transformed microorganisms containing such DNA. The present invention also relates to various methods of making and using recombinant proCVF.

Discussion of the Background

The third component of complement, C3, plays a pivotal role in both the classical and alternative pathways of complement activation, and many of the physiologic C3 activation products have important functions in the immune response and host defense (Müller-Eberhard, H. J., 1988, Annu. Rev. Biochem. 57:321). In the alternative pathway, the activated form of C3, C3b, is a structural subunit of the C3 convertase. This bimolecular enzyme consists of C3b and Bb, the activated form of factor B. This enzyme is formed by the binding of C3b to factor B that is subsequently cleaved by factor D, resulting in the formation of the C3 convertase, C3b,Bb, and the release of the activation peptide Ba. The C3 convertase activates C3 by cleaving the molecule into C3b and the anaphylatoxin, C3a. The C3b molecule will bind in close proximity to the C3 convertase. Eventually, the bound C3b will allow for the activation of C5 into C5b and the anaphylatoxin, C5a. C5 activation occurs by the same C3b,Bb enzyme that can cleave C5 when it is bound to an additional C3b molecule. The C5-cleaving enzyme is called C5 convertase. It is a trimolecular complex composed of $(C3b)_2$,Bb. Inasmuch as the activation of both C3 and C5 occurs at the identical active site in the Bb subunit, the enzyme is also called C3/C5 convertase; and only one EC number has been assigned (EC 3.4.21.47).

Cobra venom contains a structural and functional analog of C3 called cobra venom factor (CVF). This molecule can bind factor B in human and mammalian serum to form the complex, CVF,B (Hensley, P. M., et al, 1986, J. Biol. Chem. 261:11038), which is also cleaved by factor D into the bimolecular enzyme CVF,Bb and Ba (Vogel. C.-W., et al, 1982, J. Biol. Chem. 257:8292). The bimolecular complex CVF,Bb is a C3/C5 convertase that activates C3 and C5 analogously to the C3/C5 convertase formed with C3b (Vogel, C.-W., 1991, In Handbook of Natural Toxins, Vol. 5, Reptile and Amphibian Venoms. A. T. Tu, ed. Marcel Dekker, New York, p. 147). Although the two C3/C5 convertases C3b,Bb and CVF,Bb share the molecular architecture, the active site-bearing Bb subunit, and the substrate specificity, the two enzymes exhibit significant functional differences. The CVF,Bb enzyme is physicochemically far more stable than C3b,Bb (Vogel. C.-W., et al, 1982, J. Biol. Chem. 257:8292; Medicus, R. G., et al, 1976, J. Exp. Med. 144:1076), it is resistant to inactivation by the regulatory proteins factors H and 1 (Lachmann, P. J., et al, 1975, Clin. Exp. Immunol. 21:109; Nagaki, K., et al, 1978, Int. Arch. Allergy Appl. Immunol. 57:221), it exhibits different kinetic properties (Vogel. C.-W., et al, 1982, J. Biol. Chem. 257:8292; Pangburn, M. K., et al, 1986, Biochem J. 235:723), and it does not require additional C3b for C5 cleavage (Miyama; A., et al, 1975, Biken J. 18:193; Von Zabern, et al, 1980, Immunobiology 157:499).

CVF and mammalian C3 have been shown to exhibit several structural similarities including immunologic cross-reactivity (Alper, C. A. et al, 1983, Science 191:1275; Eggertsen, G. A., et al, 1983, J. Immunol. 131:1920; Vogel, C.-W., et al, 1984, J. Immunol. 133:3235; Grier, A. H., et al, 1987, J. Immunol. 139:1245), amino acid composition (Vogel, C.-W., et al, 1984, J. Immunol. 133:3235; Vogel, C.-W., et al, 1985, Complement 2:81), circular dichroism spectra, and secondary structure (Vogel, C.-W., et al, 1984, J. Immunol. 133:3235), electron microscopic ultrastructure (Vogel, C.-W., et al, 1984, J. Immunol. 133:3235; Smith, C. A., et al, 1982, J. Biol. Chem. 257:9879; Smith, C. A., et al, 1984, J. Exp. Med. 159:324), and amino-terminal amino acid sequence (Vogel, C.-W., et al, 1984, J. Immunol. 133:3235; Lundwall, A., et al, 1984, FEBS Lett. 169:57). Nevertheless, significant structural differences exist between the two molecules. Whereas C3 is a two-chain molecule with an apparent molecular mass, dependent on the species, of 170 to 190 kDa (Eggertsen, G. A., et al, 1983, J. Immunol. 131:1920; DeBruijn, M. H. L., et al, 1985, Proc. Natl. Acad. Sci. USA 82:708; Alsenz, J., et al, 1992, Dev. Comp. Immunol. 16:63; Vogel, C.-W., et al, 1984, Dev. Comp. Immunol. 8:239), CVF is a three-chain molecule with an apparent molecular mass of 149 kDa (Vogel, C.-W., et al, 1984, J. Immunol. Methods 73:203) that resembles C3c, one of the physiologic activation products of C3 (Vogel, C.-W., 1991, In Handbook of Natural Toxins, Vol. 5, Reptile and Amphibian Venoms. A. T. Tu, ed. Marcel Dekker, New York, p. 147; Vogel, C.-W., et al, 1984, J. Immunol. 133:3235). Another significant structural difference between C3 and CVF lies in their glycosylation, CVF has a 7.4% (w/w) carbohydrate content consisting mainly of N-linked complex-type chains with unusual α-galactosyl residues at the non-reducing termini (Vogel, C.-W., et al, 1984, J. Immunol. Methods 73:203; Gowda, D. C., et al, 1992, Mol. Immunol. 29:335). In contrast, human and rat C3 exhibit a lower extent of glycosylation with different structures of their oligosaccharide chains (Hase, S., et al, 1985, J. Biochem. 98:863; Hirani, S., et al, 1986, Biochem. J. 233:613; Miki, K., et al, 1986, Biochem J. 240:691).

The multifunctionality of the C3 protein, which interacts specifically with more than 10 different plasma proteins or cell surface receptors, has spurred significant interest in a detailed structure/function analysis of the molecule. For some ligands of C3 the binding sites have been assigned to more or less defined regions of the C3 polypeptide including factor H (Ganu, V. S., et al, 1985, Complement 2:27), properdin (Daoudaki, M. E., et al, 1988, J. Immunol. 140:1577; Farries, T. C., et al, 1990, Complement Inflamm. 7:30), factor B (Fishelson, Z., 1981, Mol. Immunol. 28:545), and the complement receptors CR1 (Becherer, J. D., et al, 1988, J. Biol. Chem. 263:14586), CR2 (Lambris, J. D., et al, 1985, Proc. Natl. Acad. Sci. USA 82:4235; Becherer, J. D., et al, 1989, Curr. Top. Microbiol. Immunol. 153:45), and CR3 (Becherer, J. D., et al, 1989, Curr. Top. Microbiol. Immunol. 153:45; Wright, S. D., et al, 1987, Proc. Natl. Acad. Sci. USA 84:1965; Taniguchi-Sidle, A., et al, 1992, J. Biol. Chem. 267:635). The elucidation of structural differences between C3 and CVF, two closely related molecules that share some properties (e.g., formation of a C3/C5 convertase) but differ in others (e.g., susceptibility to regulation by factors H and I) can be expected to help identify functionally important regions of the C3 molecule.

The inventors have recently discovered that CVF actually exists in two forms, CVF1 and CVF2. It is desirable to obtain large quantities of CVF1 and CVF2 for a number of reasons. However, the isolation of large quantities of the peptides from cobras is problematic to say the least. Thus, it is desirable to clone the genes which encode CVF1 and CVF2. It is also desirable to provide molecules that exhibit the activity of CVF and can be conveniently produced in large quantities.

SUMMARY OF THE INVENTION

Accordingly, it is one object of the present invention to provide novel molecules which exhibit the activity of CVF and which are conveniently produced in large quantities.

It is another object of the present invention to provide novel sequences of DNA which encode such a molecule exhibiting the activity of CVF.

It is another object of the present invention to provide plasmids which comprise a sequence of DNA which encodes a molecule exhibiting the activity CVF.

It is another object of the present invention to provide transformed microorganisms which contain heterologous DNA encoding such a molecule exhibiting the activity of CVF.

It is another object of the present invention to provide a method for producing large quantities of such a molecule.

It is another object of the present invention to provide various methods of using such a molecule.

These and other objects, which will become apparent during the following detailed description, have been achieved by the inventors' discovery that recombinant proCVF exhibits substantially the same activity as CVF.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2 shows the cDNA and derived amino acid sequence of CVF1 (SEQ ID NO:1,2). The $NH_2$- and C-termini of the α-, γ-, and β-chains, functionally important regions, and known ligand binding sites are indicated. Amino acid residue numbering starts at the $NH_2$-terminus of the pro-CVF1 molecule;

FIG. 3 provides a comparison of CVF1 and C3 sequences at the factor B binding site (SEQ ID NO:3–5). Comparisons were made with a sequence analysis program (Devereux, J. R., et al, 1984, *Nucleic Acids Res.* 12:387). Identical amino acid residues are boxed and shaded, whereas conservative replacements are shaded only. Amino acid residue numbering is based on the CVF1 sequence as shown in FIG. 2. The percent sequence identity and similarity with the CVF1 sequence is shown on the right;

FIG. 4 provides a comparison of CVF1 and C3 sequences at the properdin binding site (SEQ ID NO:6–8). Comparisons were made with a sequence analysis program (Devereux, J. R., et al, 1984, *Nucleic Acids Res.* 12:387). Identical amino acid residues are boxed and shaded, whereas conservative replacements are shaded only. Amino acid residue numbering is based on the CVF1 sequence as shown in FIG. 2. The percent sequence identity and similarity with the CVF1 sequence is shown on the right;

FIG. 5 provides a comparison of CVF1 and C3 sequences at the thioester site (SEQ ID NO:9–11). Comparisons were made with a sequence analysis program (Devereux, J. R., et al, 1984, *Nucleic Acids Res.* 12:387). Identical amino acid residues are boxed and shaded, whereas conservative replacements are shaded only. Amino acid residue numbering is based on the CVF1 sequence as shown in FIG. 2. The percent sequence identity and similarity with the CVF1 sequence is shown on the right;

FIG. 6 provides a comparison of C3 sequences at the convertase cleavage site with the N-terminus of the γ-chain of CVF1 (SEQ ID NO:12–14). Comparisons were made with a sequence analysis program (Devereux, J. R., et al, 1984, *Nucleic Acids Res.* 12:387). Identical amino acid residues are boxed and shaded, whereas conservative replacements are shaded only. Amino acid residue numbering is based on the CVF1 sequence as shown in FIG. 2. The percent sequence identity and similarity with the CVF1 sequence is shown on the right;

FIGS. 7A and 7B provide a comparison of CVF1 and C3 sequences at the factor H and CR2 binding sites (SEQ ID NO:15–20). The upper panel shows the factor H orientation site. The lower panel shows the discontinuous factor H binding site that includes the CR2 binding site (residues 1180–1191) with the highly conserved LYNVEA sequence in all mammalian C3 proteins. Comparisons were made with a sequence analysis program (Devereux, J. R., et al, 1984, *Nucleic Acids Res.* 12:387). Identical amino acid residues are boxed and shaded, whereas conservative replacements are shaded only. Amino acid residue numbering is based on the CVF1 sequence as shown in FIG. 2. The percent sequence identity and similarity with the cobra sequence is shown on the right;

FIGS. 9A–9C provide a comparison of cobra, human, and mouse C3 with: (a) the N-terminal CVF1 α-(SEQ ID NO:21–24); (b) the N-terminal CVF1 β-chain (SEQ ID NO:25–28); and (c) the N-terminal CVF1 γ-chain (SEQ ID NO:29–32). Comparisons were made with a sequence analysis program (Devereux, J. R., et al, 1984, *Nucleic Acids Res.* 12:387). Identical amino acid residues are boxed and shaded, whereas conservative replacements are shaded only. Amino acid residue numbering is based on the CVF1 sequence as shown in FIG. 2. The percent sequence identity and similarity with the cobra sequence is shown on the right;

FIG. 10, shows the partial cDNA sequence of CVF2 (SEQ ID NO:33–34);

Figure 16:
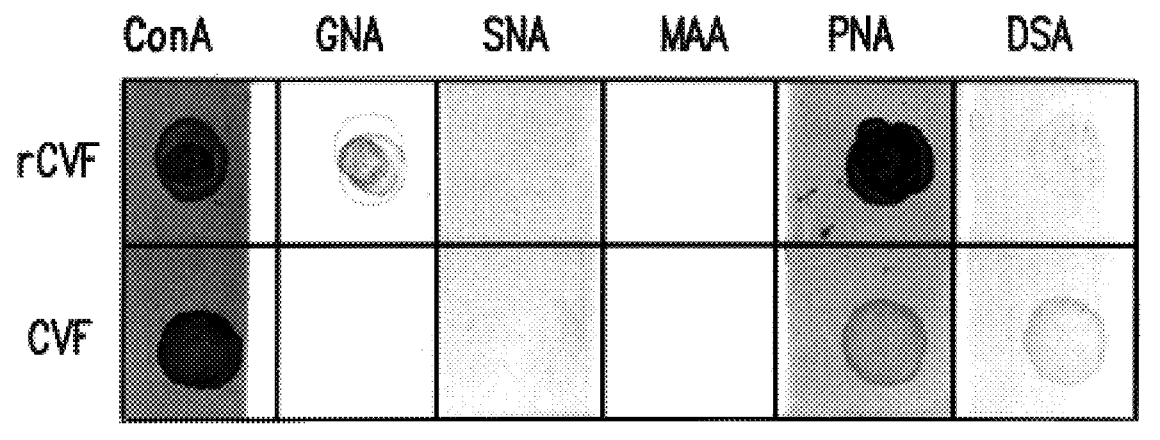

FIG. 16 shows the results of a series of agglutination reactions with CVF and proCVF: ConA, *Canavalia ensiformis*; GNA, *Galanthus nivalis*; SNA, *Sambucus nigra*; PNA, peanut agglutinin; MAA, *Maackia amurensis*; and DSA, *Datura stramonium*;

FIG. 21 shows the amino acid sequence of pre-pro-CVF and pre-proCVF-3'His (SEQ ID NO:35). For pre-pro-CVF-3'His a stretch of 6 histidine residues was added to the C-terminus of pre-pro-CVF.

DETAILED DESCRIPTION OF THE PREFERRED EMBODIMENTS

Figure 1:
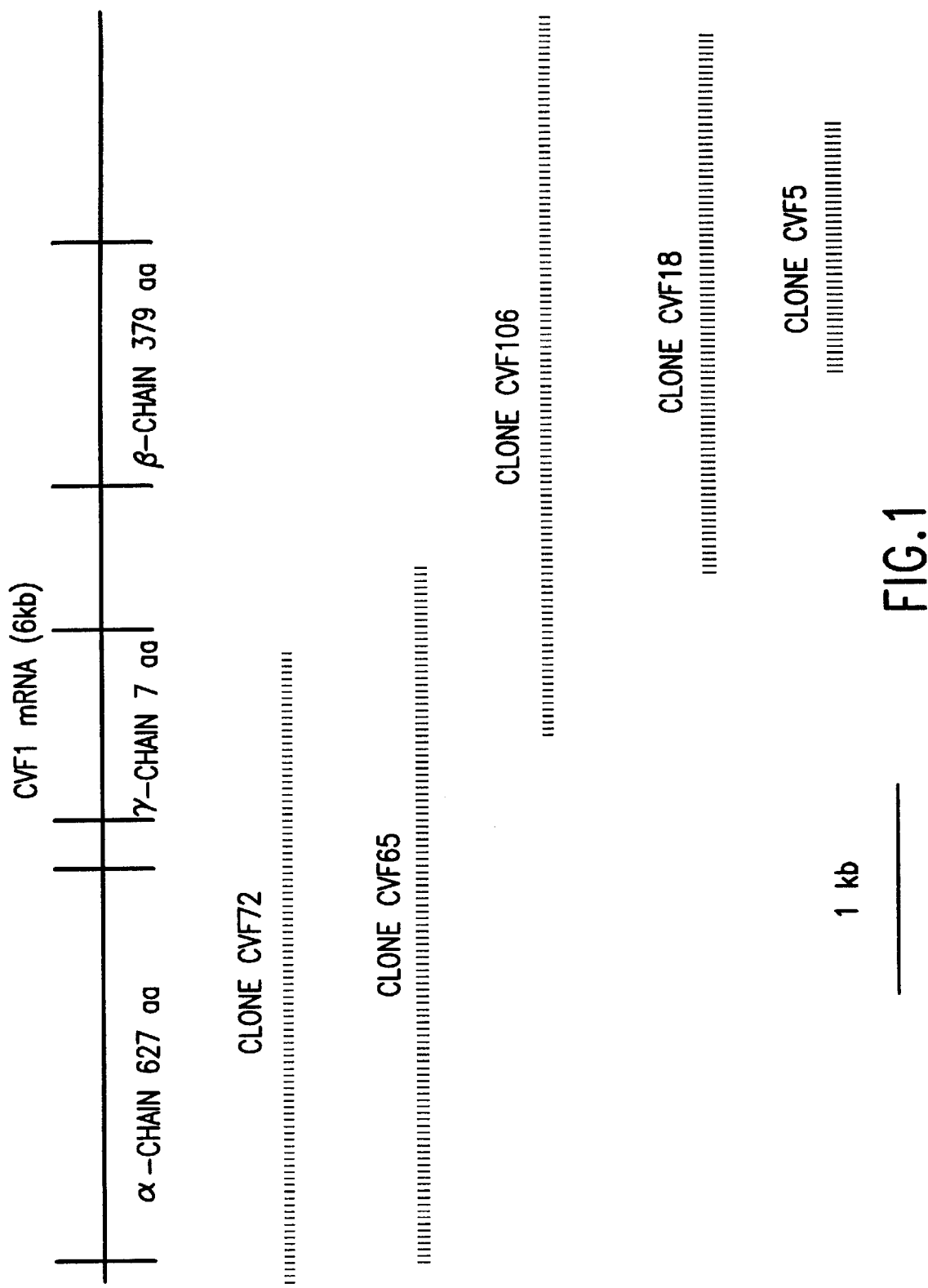
FIG. 1 depicts a map of clones used for the sequencing of CVF1. The upper portion shows a schematic drawing of CVF1 cDNA in which the positions and numbers of amino acid residues of the α-, γ-, and β-chains are indicated. The lower portion shows the relative positions of the five cDNA clones that were used to sequence the molecule.
Figure 8A:
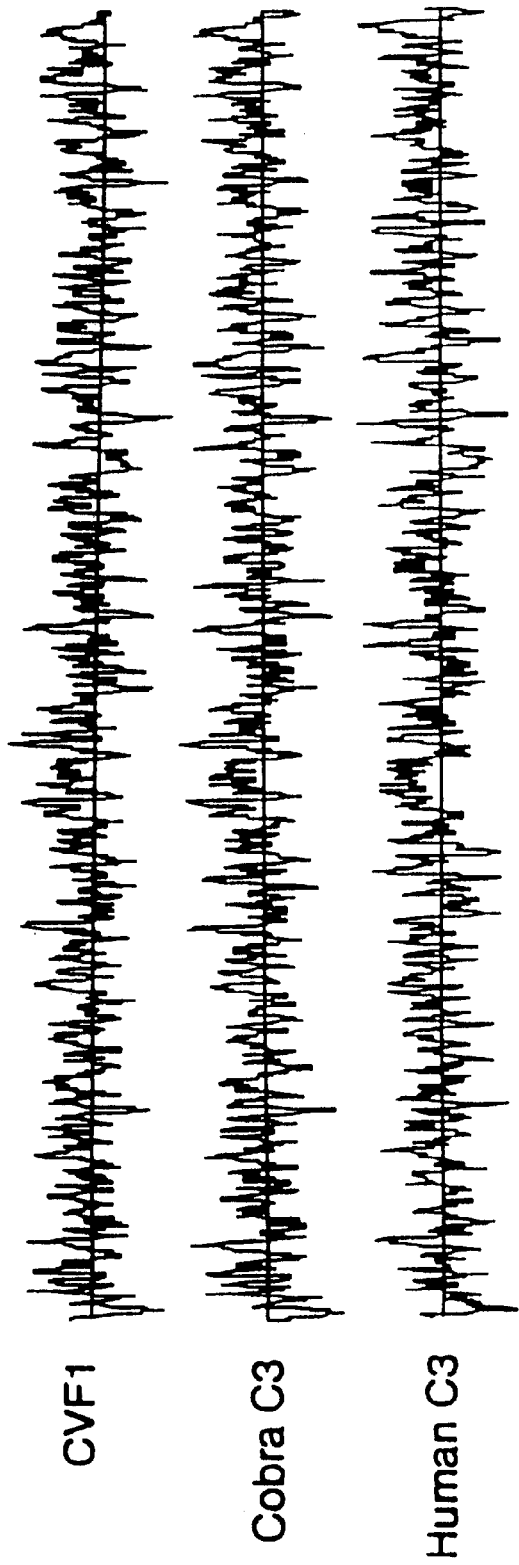
FIG. 8 shows hydophilicity/hydrophobicity plots of CVF1 and cobra and human C3 proteins. The plots were generated using a sequence analysis program (Devereux, J. R., et al, 1984, *Nucleic Acids Res.* 12:387). Hydrophilic regions are shown above, hydrophobic regions below the line. The locations of functionally important sites are indicated.
Figure 8B:
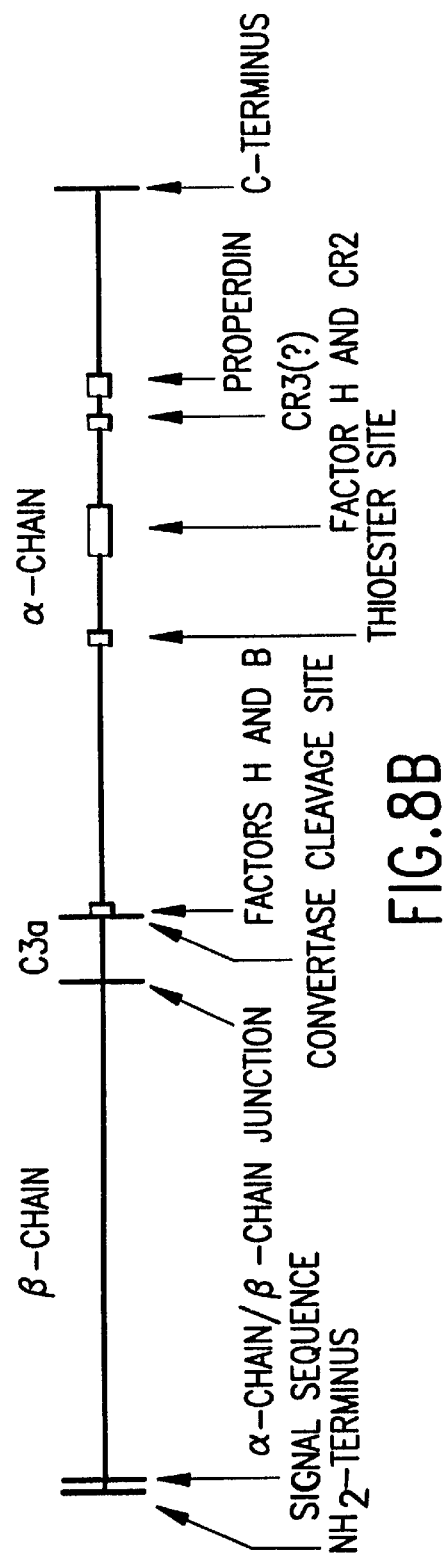
Figure 11:
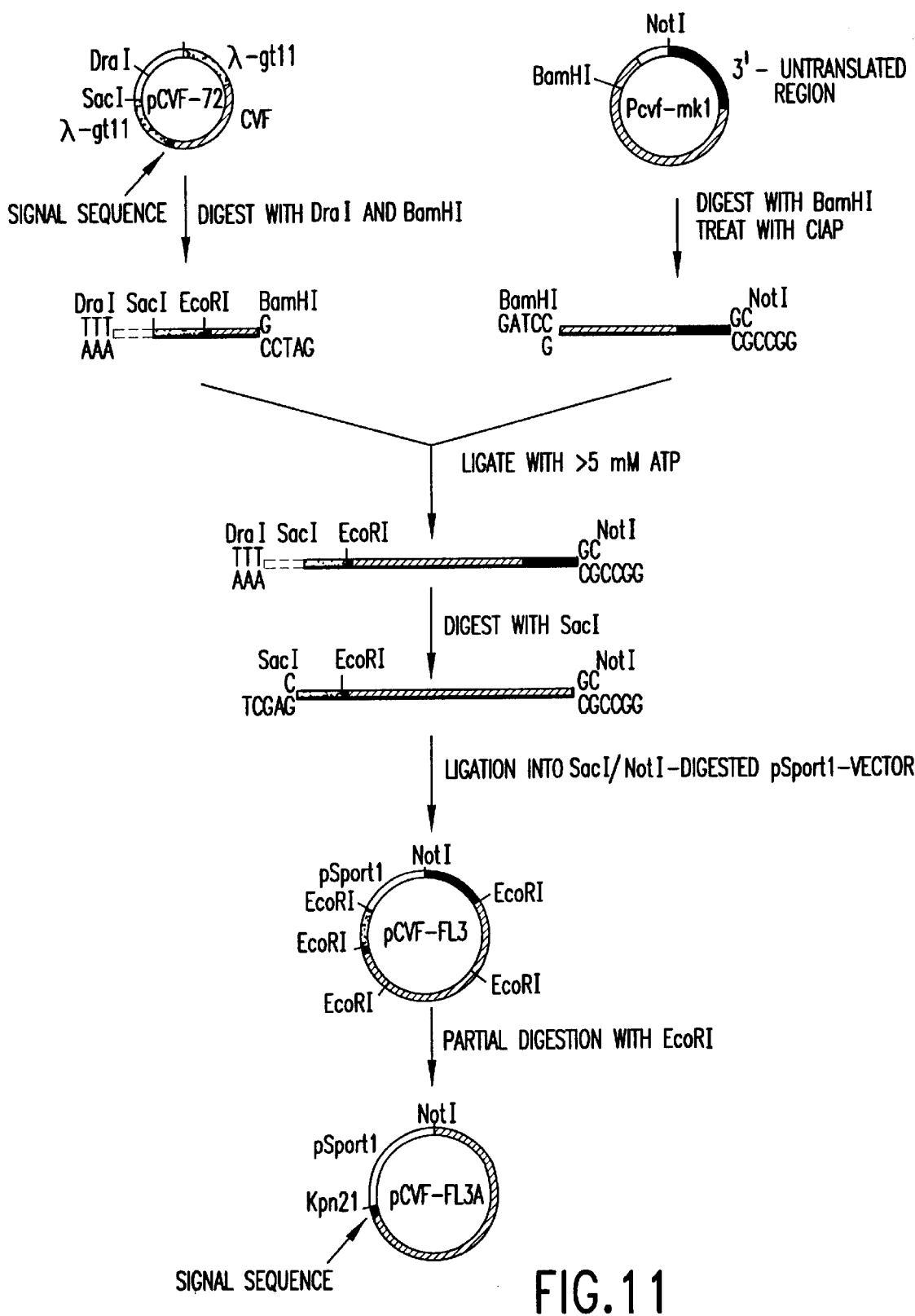
FIG. 11 is a schematic which illustrates the construction of the full-length clone pCVF-FL3Δ.
Figure 12:
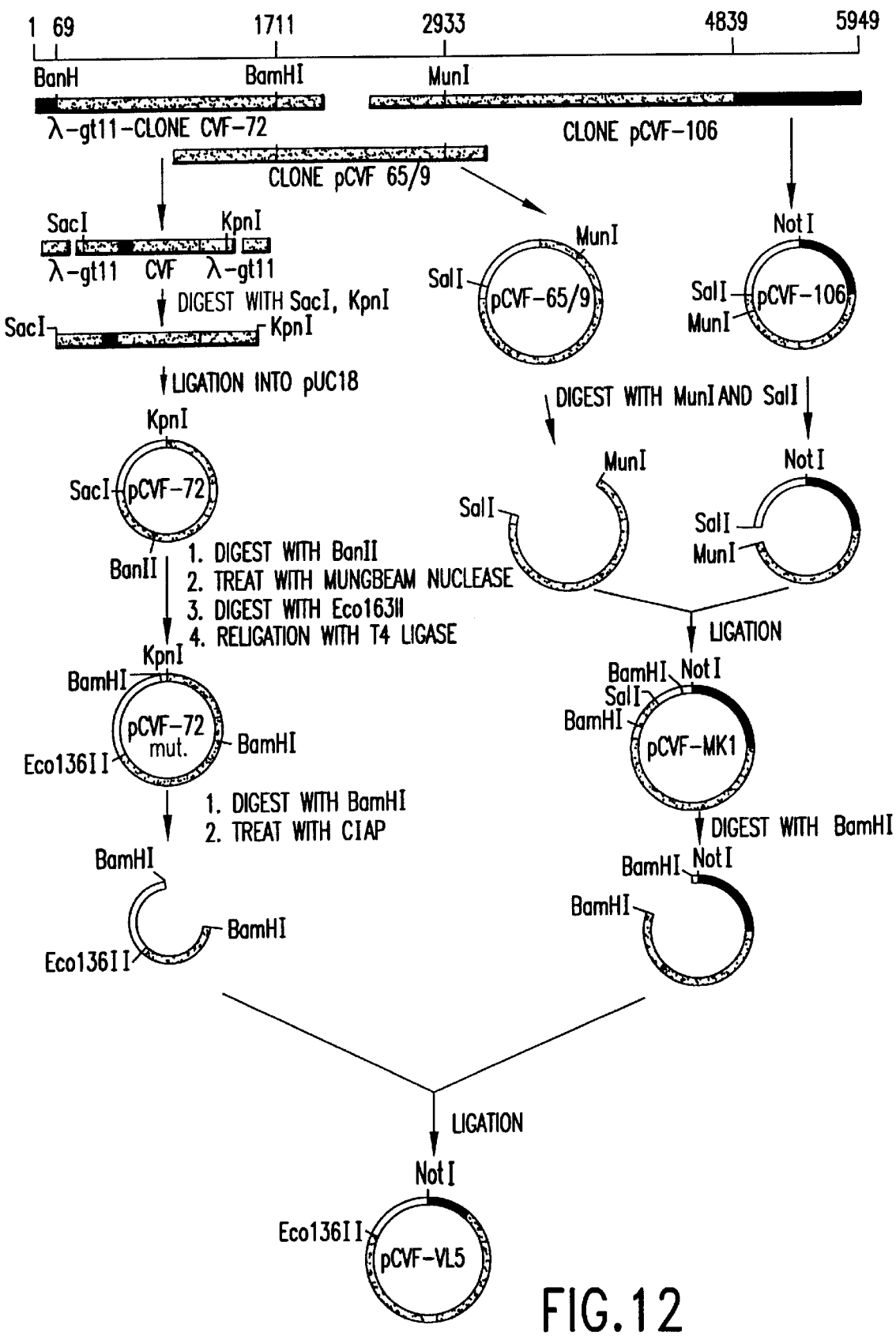
FIG. 12 is a schematic which illustrates the construction of the full-length clone pCVF-VL5.

In a first embodiment, the present invention provides recombinant proCVF. In the context of the present invention, recombinant proCVF includes recombinant proCVF1 and proCVF2, each either glycosylated, partially unglycosylated or totally unglycosylated. The present invention also provides recombinant proCVF to which 1 to 8, preferably about six histidine residues have been added to the 3' terminus It is also to be understood that the term recombinant proCVF includes those proCVF1 and proCVF2 molecules in which up to 10 amino acid residue deletions, insertions, substitutions, or combinations thereof have been made, so long as the molecule retains at least 10%, preferably at least 30%, more preferably at least 75% of the specific activity of natural CVF from Naja naja for in vitro anticomplementation as measured by the method of Ballow et al (M. Ballow et al, *J. Immunol.*, vol. 103, p. 944 (1969)). It is also to be understood that the term recombinant proCVF includes chimeric molecules in which an amino acid sequence of a particular chain (α, β . . . ) or segment of proCVF1 has been substituted for the analogous chain or segment of proCVF2 (or vice versa), with the activity proviso set forth above.

In a preferred embodiment the recombinant proCVF has the amino acid sequence:
(a) from position about −22 to position about 1620 of the amino acid sequence shown in FIG. 2;
(b) from position about −22 to position about 1620 of the amino acid sequence shown in FIG. 2 with 1 to 8 histidine residues added to the carboxy terminus;
(c) from position about −22 to position about 1620 of the amino acid sequence shown in FIG. 2 with 1 to 8 histidine residues inserted before position 1 added to the amino terminus of proCVF;
(d) from position about 1 to position about 1620 of the amino acid sequence shown in FIG. 2;
(e) from position about 1 to position about 1620 of the amino acid sequence shown in FIG. 2 with a methionine residue added to the amino terminus;
(f) from position about 1 to position about 1620 of the amino acid sequence shown in FIG. 2 with the signal peptide of the baculovirus glycoprotein gp67 (sequence I) added to the amino terminus;
(g) from position about 1 to position about 1620 of the amino acid sequence shown in FIG. 2 with the peptide of sequence II added to the amino terminus;
(h) from position about 1 to position about 1620 of the amino acid sequence shown in FIG. 2 with 1 to 8 histidine residues added to the carboxy terminus;
(i) from position about 1 to position about 1620 of the amino acid sequence shown in FIG. 2 with 1 to 8 histidine residues added to the amino terminus;
(j) from position about 1 to position about 1620 of the amino acid sequence shown in FIG. 2 with 1 to 8 histidine residues added to the carboxy terminus and a methionine residue added to the amino terminus;
(k) from position about 1 to position about 1620 of the amino acid sequence shown in FIG. 2 with 1 to 8 histidine residues added to the amino terminus and a methionine residue added to the amino terminus of the histidine residues;
(l) from position about 1 to position about 1620 of the amino acid sequence shown in FIG. 2 with the signal peptide of the baculovirus glycoprotein gp67 (sequence I) added to the amino terminus and with 1 to 8 histidine residues added to the carboxy terminus; and
(m) from position about 1 to position about 1620 of the amino acid sequence shown in FIG. 2 and with 1 to 8 histidine residues added to the amino terminus and the signal peptide of the baculovirus glycoprotein gp67 (sequence I) added to the amino terminus of the histidine residues;
wherein sequence I (gp67 signal peptide (SEQ ID NO:35)) is:
MLLVNQSHQGFNKEHTSKMVSAIVLYVL-LAAAAHSAFA;
and sequence II (peptide encoding for M start codon, 6 histidine residues, and enterokinase cleavage site (SEQ ID NO:36)) is MRGSHHHHHHGMASMTG-GQQMGRDLYNNNNK.

In an especially preferred embodiment, the recombinant proCVF is recombinant proCVF1.

In a second embodiment, the present invention provides the DNA encoding proCVF. The present DNA may be any which encodes any of the present recombinant proCVF molecules, optionally with 1 to 8 histidine residues added to the 3'-terminus. Thus, in preferred embodiments, the present DNA encodes a recombinant proCVF which has the amino acid sequence:
(a) from position about −22 to position about 1620 of the amino acid sequence shown in FIG. 2;
(b) from position about −22 to position about 1620 of the amino acid sequence shown in FIG. 2 with 1 to 8 histidine residues added to the carboxy terminus;
(c) from position about −22 to position about 1620 of the amino acid sequence shown in FIG. 2 with 1 to 8 histidine residues inserted before position 1 added to the amino terminus of proCVF;
(d) from position about 1 to position about 1620 of the amino acid sequence shown in FIG. 2
(e) from position about 1 to position about 1620 of the amino acid sequence shown in FIG. 2 with a methionine residue added to the amino terminus;

(f) from position about 1 to position about 1620 of the amino acid sequence shown in FIG. 2 with the signal peptide of the baculovirus glycoprotein gp67 (sequence I) added to the amino terminus;

(g) from position about 1 to position about 1620 of the amino acid sequence shown in FIG. 2 with the peptide of sequence II added to the amino terminus;

(h) from position about 1 to position about 1620 of the amino acid sequence shown in FIG. 2 with 1 to 8 histidine residues added to the carboxy terminus;

(i) from position about 1 to position about 1620 of the amino acid sequence shown in FIG. 2 with 1 to 8 histidine residues added to the amino terminus;

(j) from position about 1 to position about 1620 of the amino acid sequence shown in FIG. 2 with 1 to 8 histidine residues added to the carboxy terminus and a methionine residue added to the amino terminus;

(k) from position about 1 to position about 1620 of the amino acid sequence shown in FIG. 2 with 1 to 8 histidine residues added to the amino terminus and a methionine residue added to the amino terminus of the histidine residues;

(l) from position about 1 to position about 1620 of the amino acid sequence shown in FIG. 2 with the signal peptide of the baculovirus glycoprotein gp67 (sequence I) added to the amino terminus and with 1 to 8 histidine residues added to the carboxy terminus; and (m) from position about 1 to position about 1620 of the amino acid sequence shown in FIG. 2 and with 1 to 8 histidine residues added to the amino terminus and the signal peptide of the baculovirus glycoprotein gp67 (sequence I) added to the amino terminus of the histidine residues;

wherein sequence I (gp67 signal peptide) is:
MLLVNQSHQGFNKEHTSKMVSAIVLYVL-LAAAAHSAFA;
and sequence II (peptide encoding for M start codon, 6 histidine residues, and enterokinase cleavage site) is
MRGSHHHHHHGNASMTGGQQMGRD-LYNNNK.

Preferably, the present DNA encodes recombinant proCVF1. In a preferred embodiment the present DNA encodes recombinant pre-pro CVF. In a particularly preferred embodiment, the present DNA encodes pre-proCVF1.

The cDNA sequence for CVF1 is 5948 nucleotides long, containing a single open reading frame of 4926 nucleotides, coding for a single pre-pro protein of 1642 amino acid residues. The complete cDNA and amino acid sequence for CVF1 have been reported in D. C. Fritzinger et al, *Proc. Natl. Acad. Sci. USA*, vol. 91, pp. 12775–12779 (1994) and D. C. Fritzinger et al, *Proc. Natl. Acad. Sci. USA*, vol. 92, p. 7605 (1995). The reported sequence has a 5' untranslated region of 3 nucleotides and a 3' untranslated sequence of 1019 nucleotides, including a 20 base poly-A tail. In especially preferred embodiments, the present DNA has the sequence corresponding to from about position 4 to about position 4929 in the cDNA sequence shown in FIG. 2 or the sequence corresponding to from about position 70 to about position 4929 in the cDNA sequence shown in FIG. 2. Of course, it should be understood that the present DNA sequence encoding proCVF encompasses those derived from the sequence shown in FIG. 2 by any number of additions, deletions and/or substitutions, so long as the encoded proCVF possesses substantially the same anti-complementation activity as natural CVF from *Naja naja*, as described above in the context of the polypeptides.

There are several lines of evidence that support the conclusion that the cDNA is indeed the cDNA for CVF1. First of all, the derived protein sequences at the N-termini of α-, β-, and γ-chains match those of the N-termini of the protein, with a single mismatch in each sequence (data not shown). Secondly, the location of glycosylation sites is similar to that found in the protein, with 2 or 3 sites found in the α-chain, a single site in the β-chain, and no sites found in the γ-chain. Finally, the similarity to the sequence of cobra C3 implies that we have sequenced a C3 related protein. Since the mRNA used for this sequence was isolated from the venom gland of cobras, and the sequence is different from that of cobra C3, it is likely that the sequence is that of CVF1.

From the cDNA sequence, it is clear that CVF1, like cobra and other C3 proteins, is transcribed and translated as a single pre-pro-protein, which is then processed to form the mature protein. In the case of CVF1, this processing includes the removal of the signal sequence from the N-terminus of the α-chain, the removal of the 4 arginines and the "C3a" region that lie between the α- and γ-chains, the removal of the "C3d.g", region that lies between the C-terminus of the γ-chain and the N-terminus of the β-chain, and the glycosylation that occurs on the 2 (or 3) sites in the α-chain and the single site that occurs in the β-chain. While it is not known if all 3 sites in the α-chain are glycosylated, it seems likely that the close proximity of the two sites at positions 131 and 136 would not allow the glycosylation of one if the other is already glycosylated.

As stated above, CVF1 shows a great deal of homology to cobra C3, both at the protein and at the nucleic acid level. One of the goals in sequencing both cobra C3 and CVF1 was to determine if the two proteins are derived from the same gene (through differential processing at either the RNA or protein level) or from different genes. Comparing the CVF cDNA sequence to that of cobra C3 shows that the two proteins are derived from different, though closely related genes. The main reason for this conclusion is that the comparison of the two nucleic acid sequences shows that the similarity is spread throughout the molecule, with differences not localized to discreet regions. If CVF1 were a product of differential processing at the protein level, it would be expected that the cDNA sequences would be identical throughout. If the differential processing takes place at the RNA level, then one would expect to see portions of the sequence that are identical, interspersed with regions that have little or no similarity to one another. Since the two cDNAs are highly similar throughout their lengths, it is most likely that they are derived from two different genes that are closely related to one another.

The Thioester site and Factor H binding site of CVF1 and cobra C3 are remarkably similar, even though neither is present in the mature CVF1 protein. The degree of similarity found in this region, where there is no selective pressure to maintain the homology, is further proof that the CVF1 gene arose quite recently. The similarity between the two genes is also evident in the "C3a" region, that also is not present in the mature protein, and in the first 200 nucleotides of the 3' untranslated region, again implying that CVF1 and C3 only recently diverged from one another.

Recently, protease activities have been characterized in cobra venom that are able to cleave human C3 into a form that resembles C3b functionally, but has a similar subunit structure to CVF1 (O'Keefe, M. C., et al, 1988, *J. Biol. Chem.* 263:12690). Since this activity appears to be specific, and not just a random protease, it is possible that this protease serves in the maturation pathway of CVF1. Comparing the venom protease cleavage sites in human C3 to the processing sites in CVF1 shows that the enzyme cleaves human C3 at a position 11 amino acid residues downstream from the actual CVF1 processing site at the N-terminus of the γ-chain, though the venom protease site appears to be in the middle of one of the proposed Factor B binding sites. The second venom protease cleavage site is in a position similar to the C-terminus of the γ-chain, though this position has not been mapped in CVF1. The third venom protease cleavage site is in position 71 amino acids downstream from the N-terminus of the β-chain.

Given the complete structure of CVF1, and knowing the binding sites for certain regulatory proteins on C3, it should be possible to account for some of the unique properties of CVF1 in activating complement. For example, it is known that, while Factors H and I are able to regulate the activation of complement by dissociating C3b,Bb (the C3 convertase), and by cleaving C3b, CVF1 is resistant to this regulation. Mapping the Factor H binding site on CVF1 shows that the binding site is in the "C3d.g" domain that is removed during the maturation of the protein. Therefore, Factor H is unable to bind to the CVF1 containing C3/C5 convertase, preventing Factor I from cleaving the CVF moiety of the convertase. It is also interesting to speculate on the intrinsic stability of the CVF1 containing C3/C5 convertase compared to the enzyme that contains C3. Comparing the Factor B binding sites to the two proteins should provide some insight into the increased stability of the CVF1,Bb complex. One difference between the factor B binding site is the replacement of the serine at position 721 of CVF1 with an acidic amino acid in C3s.

A partial sequence of the DNA encoding of CVF2 is shown in FIG. 10. A full length sequence encoding pre-pro-CVF2 may be constructed by ligating the 3' end of any DNA sequence which encodes for a polypeptide having the amino acid sequence of from position about −22 to position about 299, as shown in FIG. 2 to the 5' end of any DNA sequence encoding a polypeptide having the amino acid sequence as shown in FIG. 10.

The DNA of the present invention for CVF2 may comprise any DNA sequence that encodes: pre-pro-CVF2, corresponding to the amino acid sequence in which the carboxy-terminus of the amino acid sequence of from position about −22 to position about 299 in FIG. 2 is bonded to the amino-terminus of the amino acid sequence of from position about 1 to position about 1333 in FIG. 10; or pro-CVF2, corresponding to the amino acid sequence in which the carboxy-terminus of the amino acid sequence of from position about 1 to position about 299 in FIG. 2 is bonded to the amino-terminus of the amino acid sequence of from position about 1 to position about 1333 in FIG. 10

In another embodiment, the present invention provides plasmids which comprise a DNA sequence encoding proCVF or pre-proCVF. Any plasmid suitable for cloning or expression may be used, and the DNA may be inserted in the plasmid by conventional techniques. Suitable plasmids and the techniques used to insert the DNA of the present invention into such plasmids are well known to those skilled in the art. For expression purposes, the DNA should be inserted downstream from a promoter and in the proper reading frame.

In another embodiment, the present invention provides transformed hosts which contain a heterologous DNA sequence encoding proCVF or pre-proCVF. Again, suitable hosts and the means for transforming them are well know to those skilled in the art. Examples of suitable prokaryotic hosts include: *E coli, B. subtilise*, etc. In the present case, it may be desirable to express the present genes in eukaryotic hosts such as CHO, NIH 3T3 cells, yeast or COS cells. Expression of recombinant proCVF in eukaryotic hosts may be carried out using a broad variety of methods, e.g., transient expression by transfection of cells with recombinant plasmids, development of stable cell lines, expression in cells infected with a recombinant virus, etc.

In yet another embodiment, the present invention provides a method for preparing proCVF by culturing a transformed host comprising a heterologous DNA sequence encoding proCVF or pre-proCVF. The exact conditions required for the culturing will depend of course on the identity of the transformed host. However, selection of culture conditions is well within the abilities of the skilled artisan.

It should be noted that although CVF1 and CVF2 are glycosylated as naturally occurring, it has been discovered that proCVF retains its activity even in the unglycosylated state. Thus, an active product may be obtained even if produced by a host incapable of effecting the proper glycosylation.

Further, proCVF may be processed from the pre-pro-form by treatment with either whole cobra venom or the purified proteases from cobra venom, as described in the Doctoral thesis of M. Clare O'Keefe, Georgetown University, 1991. Thus, active proCVF may be obtained even when produced by a host incapable of the proper post-translational processing. Of course, in some expression systems proCVF will be secreted by the host even though the DNA encodes pre-proCVF.

Natural native cobra venom factor (CVF) has been used extensively as a research agent to deplete the complement activity in the plasma of laboratory animals in vitro and in vivo, (I. R. Leventhal, et al, *Transplantation Proceedings*, vol. 25, pp. 398–399 (1993); C.-W. Vogel, et al, *J. Immunol. Methods*, vol. 73, pp. 203–220 (1984); and K. I. Gaede, et al, *Infection and Immunity*, vol. 63, pp. 3697–3701 (1995), all of which are incorporated herein by reference). Due to its ability to exhaustively activate complement, injection of CVF into vertebrate animals leads to consumption of complement. This provides for a model system to study the involvement of complement in any biological or pathological mechanism by comparing normal animals with complement-depleted, ice. CVF-treated, animals. Since recombinant pro-CVF exhibits the same activity of depleting complement activity in serum or plasma as natural CVF, recombinant pro-CVF can be used like natural CVF in a large variety of studies where animals are to be depleted of their complement activity.

Other examples of complement depletion using CVF are reported in the table below.

| Complement Depletion Studies with CVF. | |
| --- | --- |
| Subject Studied | Reference |
| Uptake of mycobacteria by monocytes | Swartz et al., Infect. Immun., 56:2223–2227 (1988) |
| Renal xenograft rejection | Kemp et al., Transplant Proc., 6:4471–4474 (1987) |
| Feline leukemia | Kraut et al., Am. J. Vet. Res., 7:1063–1066 (1987) |
| Cardiac xenograft survival | Adachi et al., Transplant Proc., 19:1145–1148 (1987) |

-continued

| Complement Depletion Studies with CVF. | |
|---|---|
| Subject Studied | Reference |
| Antitumor mechanism of monoclonal antibody | Welt et al., Clin. Immunol. Immunopathol.. 45:215–229 (1987) |
| Pulmonary vascular permeability | Johnson et al., J. Appl. Physiol., 6:2202–2209 (1986) |
| Glomerular injury and proteinuria | Rehan et al., Am. J. Pathol. 111:57–66 (1986) |
| Fowlpox virus infection | Ohta et al., J. Virol., 2:670–673 (1986) |
| Endotoxin-induced lung injury | Flick et al., Am. Rev. Respir. Dis. 135:62–67 (1986) |
| Immunologically mediated otitis media | Ryan et al., Clin. Immunol. Immunopathol., 40:410–421 (1986) |
| Antigen-induced arthritis | Lens et al., Clin. Exp. Immunol., 3:520–528 (1984) |
| Humoral resistance to syphilis | Azadegan et al., Infect. Immun., 3:740–742 (1984) |
| Acute inflammation induced by *Escherichia coli* | Kopaniak and Movat, Am. J. Pathol., 110:13–29 (1983) |
| Cutaneous late-phase reactions | Lemanske et al., J. Immunol., 130:1881–1884 (1983) |
| Bleomycin-induced pulmonary fibrosis | Phan and Thrall, Am. J. Pathol., 107:25–28 (1982) |
| Delayed hypersensitivity reactions | Jungi and Pepys, Immunology, 42:271–279 (1981) |
| Vitamin $D_2$-induced arteriosclerosis | Pang and Minta, Artery, 2:109–122 (1980) |
| Macrophage activation by Corynebacterium | Ghaffar, J. Reticuloendothel. Soc., 27:327–335 (1980) |
| Allergic encephalomyelitis | Morariu and Dalmasso, Ann. Neurol., 5:427–430 (1978) |
| Effect of complement depletion on IgG and IgM response | Martinelli et al., J. Immunol. 121:2043–2047 (1978) |
| Myocardial necrosis after coronary artery occlusion | Maroko et al., J. Clin. Invest., 3:661–670 (1978) |
| Resistance to ticks | Wikel and Allen, Immunology, 34:257–263 (1978) |
| Lung clearance of bacteria | Gross et al., J. Clin. Invest., 62:373–378 (1978) |
| Immune complex disease in the lung | Roska et al., Clin. Immunol. Immunopathol., 8:213–224 (1977) |
| Migration of T and B lymphocytes into lymph | Spry et al., Immunology, 32:947–954 (1977) |
| Leukocyte circadian variation | Hoopes and McCall, Experientia, 2:224–226 (1977) |
| Initial gingivitis | Kahnberg et al., J. Periodont. Res., 5:269–278 (1976) |

A more recent example where complement depletion in laboratory animals has become important is the suppression of hyperacute rejection in xeno-transplantation, because complement has been shown to be a major player in hyperacute rejection. Another more recent application is the depletion of complement activity in gene therapy when retroviruses are used as a vehicle for gene transfer to the target cells. Retroviruses are lysed by complement and can survive in complement-depleted serum.

In addition to the use of recombinant proCVF to deplete complement in laboratory animals, recombinant pro-CVF may also be used as a therapeutic agent in humans for the treatment of cancer. One application is the covalent coupling of CVF to monoclonal antibodies with specificity for a tumor surface antigen. By coupling proCVF to such an antibody, complement activation is targeted to the tumor cell which is subsequently lysed by the complement system. Thus, proCVF may be used for antibody targeting to tumor cells. Since, proCVF is insensitive to factor H control, this method will lead to the selective destruction of the cancer cells. In addition, single chain proCVF molecule may be used in a fusion chimeric protein with an scFv-fragment of an antibody for the same purpose.

The property of the CVF,Bb enzyme to exhaustively activate complement has also been exploited for the selective killing of tumor cells by coupling of CVF to monoclonal antibodies with specificity for surface antigens of tumor cells. Antibody conjugates with CVF will target CVF to the cell surface, at which the CVF,Bb enzyme forms from complement factors B and D of the host complement system. The antibody-bound and, therefore, cell surface-bound CVF, Bb enzyme will continuously activate C3 and C5 and elicit complement-dependent target cell killing. Antibody conjugates with CVF have been shown to kill human melanoma cells (Vogel and Müller-Eberhard, *Proc. Natl. Acad. Sci. USA*, 78:7707–7711 (1981); Vogel et al., *Modern Trends in Human Leukemia VI*, Neth et al, eds; Springer Verlag, Berlin, pp. 514–517 (1985)), human lymphocytes and leukemia cells (Müller et al., *Br. J. Cancer*, 54:537 (1986); M üller and Müller-Ruchholtz, *Immunology*, 173:195–196 (1986); Müller and Müller-Ruchholtz, *Leukemia Res.*, 11:461–468 (1987)), and human neuroblastoma cells (Juhl et al., *Proc. Am. Assoc. Cancer Res.*, 30:392 (1989); Juhl et al., *Mol. Immuno.*, 27:957–964 (1990)).

An additional clinical use for proCVF is the use of proCVF to deplete complement in patients undergoing xenotransplantation to suppress the hyperacute rejection of the foreign organ. Another clinical use is the temporary depletion of complement in patients undergoing gene therapy using retroviral vectors. In addition, there is a host of other diseases where complement is known to be involved in the pathogenesis of disease, and where depletion of complement by proCVF might be of clinical use such as the diseases with circulating immune complexes (e.g. rheumatoid arthritis, lupus erythematosus, septic shock, adult respiratory distress syndrome, ischemia-reperfusion injury, and thermal injury from burns (see: F. D. Moore, Jr., et al, in *Therapeutic Immunology*, K. F. Austen, et al, Eds., Blackwell Science, Cambridge Mass., 1996, which is incorporated herein by reference).

Thus, the present invention also provides a method for complement depletion in animals by administration of proCVF. The animal may be any vertebrate, such as reptiles, fish, birds (chickens, turkeys, etc.), and mammals such as guinea pigs, mice, rats, pigs, baboons, chimps, dogs, cats, horses, cows, and humans. The proCVF may be administered by injection (intravenous or intraperitoneal) or by slow drip intravenous administration. The proCVF will typically be administered in the form of a sterile saline solution containing 10 to 2000 U/ml of proCVF, preferably 100 to 500 U/ml of proCVF, where a unit of proCVF has the same activity as a unit measured by the method of Ballow (see M. Ballow et al, *J. Immunol.*, vol. 103, p. 944 (1969) which is incorporated herein by reference).

In the case of a guinea pig an appropriate single dose for complete decomplementation for 7 days is about 300–800

U/kg of body weight. In the case of humans, an appropriate dosage of proCVF is 1 to 1000 U/kg of body weight, preferably 30 to 80 U/kg of body weight, for complete decomplementation. for some applications, multiple injections might be useful to prolong the period of decomplementation, e.g., four 80 U/kg injections in an interval of 60 hours divided into 4 injections spaced over a period of 24 hours.

Other features of the invention will become apparent in the course of the following descriptions of exemplary embodiments which are given for illustration of the invention and are not intended to be limiting thereof.

EXAMPLES

I. CVF1 and CVF2

Materials and Methods

Materials:

Solutions for RNA isolation, λgt11 cloning, and hybridization probe labeling were obtained from Amersham (Skokie, Ill.). In addition, an RNA isolation kit was purchased from Stratagene (La Jolla, Calif.). Reagents for cDNA preparation were obtained either from Gibco-BRL (Gaithersburg, Md.), or from Amersham. Oligo dT-cellulose was from Boehringer Mannheim (Indianapolis, Ind.), or from Invitrogen (San Diego, Calif.). Restriction enzymes were from either Pharmacia, from New England Biolabs (Beverley, Mass.), or from Gibco-BRL. Plasmids pUC18 and pUC19 were purchased from Boehringer Mannheim (Indianapolis, Ind.), while M13mp18 and M13mp19 were purchased from New England Biolabs. DNA modification enzymes were obtained from Pharmacia, New England Biolabs, or Gibco-BRL, and DNA sequencing reagents were obtained from United States Biochemicals (Cleveland, Ohio). Reagents required for PCR amplification of venom gland library ensens were obtained from Perkin-Elmer Cetus. Oligonucleotides for screening the libraries were obtained from Clontech (Palo Alto, Calif.), or were synthesized, using an Applied Biosystems #380 DNA synthesizer. A GeneCleanII kit, containing reagents used for isolation of DNA from agarose gels, and for the purification of PCR products, was obtained from Bio101 (La Jolla, Calif.). Nitrocellulose and nylon membranes for plaque lifts were obtained from Schliecher and Scheull (Keene, N.H.). Rabbit anti-goat IgG (Alkaline Phosphatase conjugated) was obtained from Sigma (St. Louis, Mo.). [$\alpha$-$^{32}$P]dATP, [$\alpha$-$^{32}$P]dCTP, and [$\alpha$-$^{35}$S]dATP were obtained from Amersham.

Methods:

RNA Isolation from Cobra Venom Glands: Adult cobras (*Naja naja*, 1.5–2 meters in length) were anesthetized with katamine (70 μg/kg i.m.) and with halothane/oxygen by intubation, essentially as described (Vogel, C.-W., et al, 1985, *Dev. Comp. Immunol.* 9:311). Venom glands were removed and immediately frozen in liquid nitrogen. For RNA preparation, approximately 1 gram of tissue was suspended (while frozen) in 20 ml of a solution of 4M guanidinium thiocyanate and 1.14M β-mercaptoethanol, and the RNA extracted according to the instructions supplied with the Amersham RNA Extraction Kit. This procedure was based on a published procedure (Han, J. H., et al, 1987, *Biochemistry* 26:1617). Poly-A containing RNA was then isolated by chromatography over oligo-dT cellulose, (Jacobson, A., 1987, In *Methods in Enzymology*, Vol. 152. S. L. Berger and A. R. Kimmel, eds. Academic Press, Orlando, Fla., p. 254). Whole RNA was also prepared using the Stratagene RNA isolation kit, in which the organs were homogenized in the presence of guanidinium isothiocyanate and β-mercaptoethanol, followed by phenol extraction and isopropanol precipitation (Chomczynski and Sacchi, 1987). Following extraction, poly A+ RNA was prepared by chromatography over oligo-dT cellulose, as described above.

cDNA Synthesis and Cloning: Cobra venom gland cDNA was synthesized (Krug, M. S., et al, 1987, In *Methods Enzymology*. Vol. 152. S. L. Berger and A. R. Kimmel, eds. Academic Press. Orlando, Fla., p. 316; Gubler, U., 1987, In *Methods in Enzymology*, vol. 152. S. L. Berger and A. R. Kimmel. eds. Academic Press, Orlando. Fla. p. 330) using the cDNA synthesis kit from Amersham. cDNA was synthesized using both oligo-dT and random hexamers as the primers. cDNA was then prepared for cloning into λgt11 (Wu. R., et al, 1987, In *Methods in Enzymology*. vol. 152. S. L. Berger and A. R. Kimmel, eds. Academic Press, Orlando, Fla. p. 343), and the recombinant λ clones were packaged (Hohn, B., et al 1977, *Proc. Natl. Acad. Sci. USA* 74:3259). *E. coli* Y1090 (r, m+) was used as the host for recombinant λgt11.

In addition, cDNA was prepared using Superscript (RNase H⁻) MMLV Reverse Transcriptase (Gerard et al, 1989). In this case, double stranded cDNA was sized on a 1% Agarose gel in TAE buffer. cDNA greater than 4.5 kb was excised from the gel, and the DNA extracted from the agarose using the GeneCleanII kit from Bio101. This cDNA was then cloned into the plasmid pSPORT (Chen and Segburg, 1985), and the recombinant plasmids transformed into *E. coli* DH5α competent cells.

Screening of λgt11 Libraries: Libraries were screened (Young, R. A., et al, 1983, *Science* 222:778; Huynh, T. V., et al, 1985, In *DNA Cloning* vol. 1. A Practical Approach. D. M. Glover. ed. IRL Press, Oxford, p 49). The primary antibody for screening the venom gland library was goat anti-CVF antiserum. Further plaque purification was done as described above, using successively lower plaque densities. Later screening was done by the hybridization protocol (Wahl, G. M., et al, 1987, In *Methods in Enzymology*, vol. 152. S. L. Berger and A. R. Kimmel, eds. Academic Press, Orlando, Fla., p. 415), using the clones derived from the antibody screening as probes. These probes were labeled with [$\alpha$-$^{32}$P]dATP or [$\alpha$-$^{32}$P]dCTP (Feinberg, A. P., et al, 1983, *Anal. Biochem*. 132:6). pSPORT libraries were screened using other cDNA clones as a probe.

Subcloning and DNA Sequence Analysis: Clones containing CVF inserts were grown up on agarose plates and their DNA prepared as described (Maniatis, T., et al, 1982, *Molecular Cloning—A Laboratory Manual*. Cold Spring Harbor Laboratory, Cold Spring Harbor, N.Y.). Inserts were prepared by EcoR1 digestion, followed by agarose gel electrophoresis. In some cases, λgt11 inserts were isolated using the polymerase chain reaction (PCR) on a Savant Model TC49 thermal cycler. In this case, λgt11 amplimers from Clontech were used as primers, and the inserts were amplified using the protocol supplied with the amplimers. This consisted of 30 cycles with a 15 sec. denaturing stop at 94° C., 15 sec. of annealing at 58° C. and a 1 minute extension at 72° C. in a 50 μl reaction mixture containing 10 mM Tris-HCl (pH 8.3), 50 mM KCl, 2 mM MgCl$_2$, 1 mM in each deoxynucleoside triphosphate, 1 μM in each primer, 1.25 U of Amplitaq® polymerase, and approximately 100 ng DNA to be amplified. Following amplification, the inserts were purified with the Bio101 Genecleanil kit, the DNA digested with EcoRI, and electrophoresed through an agarose gel. In all cases, fragments were eluted from the gel using the IBI Electroeluter (Model UEA) or by using the GeneCleanII kit from Bio101. The DNA inserts were then ligated into pUC18 (Yanisch-Perron, C., et al, 1985, *Gene*

33:103) and transformed into *E. coil* JM105 to facilitate the production of large quantities of the insert. Subfragments of the CVF inserts were subcloned into M13mp18 or mp19 (Yanisch-Perron, C., et al, 1985, *Gene* 33:103) for sequence analysis. Sequencing was performed using the dideoxy-chain termination technique (Sanger, F., et al, 1977, *Proc. Natl. Acad. Sci. USA* 74:5463). The Sequenase Version 2.0 sequencing kit from U.S. Biochemicals (Tabor, S., et al, 1989, *Proc. Natl. Acad. Sci. USA* 86:4076) was used as the source of enzymes, chemicals and primers for sequencing. The DNA sequence was assembled and analyzed using the group of sequence analysis programs written by the Genetics Computer Group of the Wisconsin Biotechnology Center (Devereux, J. R., et al, 1984, *Nucleic Acids Res.* 12:387).

Results

Screening of the cobra venom gland library. Poly-A+ RNA from cobra venom glands was used for the preparation of cDNA that was cloned into the EcoRI site of λgt11. Libraries were prepared from cDNA that had been primed with oligo-dT and with random hexamers. Each library contained at least $5 \times 10^6$ clones. Initially, $5 \times 10^5$ clones from the random primed library were screened using CVF specific antisera to detect clones producing CVF containing fusion proteins. In the first round of screening, a single positive clone (CVF5, 1.1 kb, FIG. 1) was isolated. Sequence analysis of this clone revealed that it contained a single open reading frame of 639 nucleotides comprising the C-terminal 213 amino acid residues of the β-chain, and an 3'-untranslated region of 502 nucleotides. This represented approximately 12% of the mature protein.

To obtain clones representing the rest of the CVF message, several strategies were used. First, the oligo-dT primed library was screened by using hybridization, using CVF5 as a probe. This resulted in the isolation of several clones, one of which (CVF18, 2.6 kb) was used for further sequence analysis. CVF18 contains the 3'-end of the CVF message, with an open reading frame of 1002 nucleotides, and 3' untranslated region of 994 nucleotides. Hybridization screening of an oligo-dT primed venom gland library yielded the clone CVF106 (3.5 kb). Clones containing the 5' end of the CVF cDNA were isolated by screening the random primed λgt11 venom gland library by hybridization, using upstream restriction fragments of sequenced DNA as probes. By this means, two additional clones, CVF65 (3.4 kb) and CVF72 (2.0 kb) were isolated for sequencing. FIG. 1 shows the placement of the clones used for sequencing on the CVF1 mRNA.

Structure of the Cobra Venom Factor cDNA. The CVF1 cDNA is 5948 nucleotides in length. It contains a single open reading frame of 4926 nucleotides, coding for a prepro-protein of 1642 amino acid residues (FIG. 2). The cDNA has a 5' untranslated region of 3 nucleotides, and a 3' untranslated region of 1019 nucleotides, including a poly-A tail of 20 bases. The coded pre-pro-protein has a signal sequence of 22 residues with a core rich in hydrophobic amino acids. The signal sequence is followed by the 627 amino acid α-chain. The α-chain has three glycosylation sites at residues 131, 136, and 187. Immediately following the C-terminus of the α-chain, there are 4 arginine residues, and a 68 amino acid peptide resembling the C3a anaphylatoxin. There is a single glycosylation site at position 640, though this site is not present in the mature protein. The γ-chain begins at position 710, and extends for approximately 300 amino acid residues. The position of the C-terminus of the γ-chain is unknown, and is apparently heterogeneous. The γ-chain contains no glycosylation sites. The β-chain of CVF begins at position 1242, and extends for 378 residues to the end of the open reading frame. The β-chain contains a single glycosylation site at position 1324.

The G+C composition of the open reading frame for CVF1 is 43.5% (for the whole cDNA: 42.4%). This is approximately the same as cobra C3, though lower than that for sequenced mammalian C3s.

Homology to cobra and other C3 proteins. The CVF1 sequence was compared to C3 sequences from cobra, human, and mouse. CVF1 shows a high degree of homology to cobra C3 at both the nucleic acid and protein level. At the protein level, CVF1 is nearly 85% identical to cobra C3 (greater than 91% similar if conservative replacements are allowed), while the nucleic acid sequences of the two messages are greater than 93% identical. CVF1 also shows a high, though lesser degree of homology to human and mouse C3 sequences. For example, the protein sequence of CVF is nearly 50% identical to that of human C3 (more than 69% similar if conservative replacements are allowed), while the nucleic acid sequence is nearly 57% identical. Comparing the CVF sequence to that of mouse C3, we find that the protein sequences are more than 51% identical (70% similar), and the nucleic acid sequences are nearly 58% identical. Dotplot comparisons of the CVF1 protein sequence with that of cobra and human C3 show that the homologies are spread throughout the molecule.

The homology between CVF1 and mammalian C3s is markedly higher than the average at certain ligand binding sites. For example, at the Factor B binding site, near the N-terminus of the γ-chain, CVF is 90% similar (though it is only 30–40% identical) to the homologous regions of other sequenced C3s (FIG. 3). The homology is also quite high at the properdin binding site (FIG. 4), where greater than 53% of the amino acid residues are identical, and about 80% of the amino acids are similar.

Interestingly, some sites are well conserved, even though they are not present in the mature protein. The best example of this is the sequence around the internal thioester site, where approximately 70% of the sequence is identical, and 80% is similar (FIG. 5). At the Factor H binding site, which is also not present in the mature protein, the homology is not noticeably greater than in the rest of the protein (FIG. 6). However, there is a stretch of 9 amino acid residues in the second portion of the discontinuous Factor H binding site (1192–1200 in CVF1) that is strictly maintained in all of the sequences examined, including rat and rabbit (data not shown), implying conservation of at least part of the Factor H binding site.

Additional clones encoding a distinct CVF were also isolated. The protein encoded by this gene is referred to as CVF2, and a partial sequence for CVF2 is shown in FIG. 10. The clones containing the DNA of CVF2 were obtained in the same series of experiments which gave the DNA for CVF1.

Expression of CVF clones in eukaryotic cells. Transient expression studies of CVF are done by transfecting CHO of NIH 3T3 cells with CVF sequences cloned into the mammalian expression vector pMT2, containing the SV40 origin of replication and early gene enhancer, the adenovirus major late promoter fused to the adenovirus tripartite leader, a hybrid intron splice site, and the SV40 polyadenylation signal. The CVF cDNA is ligated into the unique EcoRI site that is between the intron and the polyA addition site, and recombinant plasmids are transformed into *E. coli* DH5α. Recombinant clones are checked for the orientation of the insert by restriction analysis. Plasmids containing the CVF insert in the proper orientation are isolated and purified by two rounds of isopycnic $CsCl_2$ gradient centrifugation, and transformed into COS cells by calcium phosphate mediated transfection. The transformed cells are then grown for 24 hrs, and both the cells and the media are assayed for the CVF production by Western analysis as described above.

For production of larger quantities of CVF, the baculovirus expression system is used. In this system, a plasmid containing the gene to be expressed is co-transfected into *Spodopera frugiperda* (Sf9) cells, along with the wild type *Autographica californica* nuclear polyhedrosis virus (AcNPV). Following transfection, up to 90% of the wild type viruses acquire the gene to be expressed by homologous recombination.

II. Recombinant ProCVF

1. Methods and Materials

1.1 Buffers and Solutions

| | | |
|---|---|---|
| CAPS blotting buffer | 10 mM | CAPS (2-[Cyclohexylamino]-1-propanesulfonic acid) |
| | 10% (v/v) | Methanol, adjust to pH 11.0 with NaOH |
| Coomassie R250 staining sol'n | 0.25% (w/v) | Coomassie brilliantblue R250 |
| | 45% (v/v) | Methanol |
| | 45% (v/v) | $H_2O$ |
| | 10% (v/v) | Acetic acid, filtered through paper filter before usage. |
| Coomassie R250 destaining sol'n | 45% (v/v) | Methanol |
| | 45% (v/v) | $H_2O$ |
| | 10% (v/v) | Acetic acid |
| Colloidal Coomassie stain premix | 0.1% (w/v) | Coomassie Brilliant Blue G (Sigma) |
| | 2% (v/v) | Phosphorous acid |
| | 15% (w/v) | Ammonium sulfate, stored at 4° C. in the dark, shake well before usage. |
| Colloidal Coomassie staining sol'n | 80% (v/v) | Colloidal Coomassie stain premix |
| | 20% (v/v) | Methanol should be prepared fresh and shaken well before usage |
| Colloidal Coomassie detain. sol'n | 50% (v/v) | Methanol |
| | 40% (v/v) | $H_2O$ |
| | 10% (v/v) | Acetic acid |
| DNA loading buffer (5×) | 20% (w/v) | Ficoll 400 |
| | 100 mM | EDTA |
| | 0.025% (w/v) | Bromphenolblue |
| | 0.025% (w/v) | Xylenxyanol FF |
| Virus Extraction Buffer | 0.1 M | Tris-HCl, pH 7.5 |
| | 0.1 M | $Na_2EDTA$ |
| | 0.2 M | Potassium chloride |
| $GVBS^{++}$ | 2.5 mM | Sodium barbital (Sodium-5,5-diethylbarbituric acid) |
| | 143 mM | Sodium chloride |
| | 0.75 mM | Magnesium chloride |
| | 0.15 mM | Calcium chloride |
| | 0.1% (w/v) | Gelatine, pH 7.5 |
| LB Medium | 1% (w/v) | Tryptone |
| | 0.5% (w/v) | Yeast extract |
| | 1% (w/v) | Sodium chloride, adjust pH to 7.0. For agar plates, add 1.5% (w/v) agar |
| Silverstain fixing sol'n | 30% (v/v) | Ethanol |
| | 15% (v/v) | Acetic acid |
| Silverstain incubation sol'n | 25% (v/v) | Ethanol |
| | 0.5 M | Sodium acetate |
| | 2.5 mM | Sodium thiosulfate |
| | 0.1% (v/v) | Glutaraldehyde (25% aq. sol.) |
| Silverstain staining sol'n | 0.1% (w/v) | Silver nitrate |
| | 0.006% (v/v) | Formaldehyde solution (37%) |
| Silverstain developing sol'n | 2.5% (w/v) | Sodium carbonate |
| | 0.006% (v/v) | Formaldehyde solution (37%) |
| Silverstain stop sol'n | 50 mM | $Na_2EDTA$ |
| TAE buffer (50×) | 24.2% (w/v) | Tris base |
| | 5.71% (v/v) | Acetic acid |
| | 10% (v/v) | 0.5 M EDTA, pH 8.0, adjust pH to ~8.5. |
| TBE buffer (10×) | 10.8% (w/v) | Tris base |
| | 5.5% (w/v) | Boric acid |
| | 4% (v/v) | 0.5 M EDTA, pH 8.0 |
| TE buffer | 1% (v/v) | 1 M Tris, pH 7.4, 7.6 or 8.0 |
| | 0.2% (v/v) | 0.5 M EDTA, pH 8.0 |
| TBS (Tris buffered saline) | 20 mM | Tris base |
| | 500 mM | Sodium chloride, adjust to pH 7.5 |
| TBS (5×) | 100 mM | Tris base |
| | 1.5 M | Sodium chloride, adjust to pH 7.5, dilute to 1× before usage |
| Transfection Buffer | 25 mM | Hepes, pH 7.1, |
| | 140 mM | Sodium chloride |
| | 125 mM | Calcium chloride |
| TSS | 85% (v/v) | LB-medium |
| | 10% (w/v) | PEG-8000 |
| | 5% (v/v) | DMSO |
| | 50 mM | Magnesium chloride, pH 6.5 |
| VBS (Veronal buffer saline) | 2.5 mM | Sodium barbital (Sodium-5,5-diethylbarbituric acid) |
| | 143 mM | Sodium chloride, pH 7.5 |
| $VBS^{++}$ (Veronal buffer saline) | 2.5 mM | Sodium barbital (Sodium-5,5-diethylbarbituric acid) |
| | 143 mM | Sodium chloride |
| | 0.75 mM | Magnesium chloride |
| | 0.15 mM | Calcium chloride, pH 7.5 |

1.2 Enzymes

New England Biolabs:
  KpnI, SacI, BanII, NotI, BamHI, DraI, SaII, Bsu36I, mungbean nuclease MBI Fermentas:
  Ecl 136 II, Mun I, SmaI, EcoRI, Kpn2I, Bsp119I, CIAP (calf intestinal alkaline phosphatase)

Amersham:
  PshAI

1.3 Construction of full-length CVF cDNA clones

For the expression of recombinant proCVF two clones were constructed using partial CVF cDNA clones from a λgt11-library. The resulting pCVF-FL3Δ represents the entire CVF cDNA including the signal sequence. pCVF-VL5 also represents the entire sequence, but the signal sequence of CVF was truncated.

Experimental:

Two of the parental clones (CVF72 and pCVF106) for the construction of full-length CVF cDNA were described previously (D. C. Fritzinger et al, Molecular Cloning and Derived Primary Structure of Cobra Venom Factor, *PNAS*, vol. 91, pp. 12775–12779 (1994)) and above. CVF72 is a λgt11-clone containing a 2 kb 5'-end fragment of the CVF cDNA. pCVF106 is a clone in pSPORT1 vector (Gibco BRL) containing a 3 kb 3'-end fragment of CVF. pCVF65/9 is a pUC18 clone containing a EcoRI-fragment from the λgt11-clone CVF65, which was also described previously (D. C. Fritzinger et al, Molecular Cloning and Derived Primary Structure of Cobra Venom Factor, *PNAS*, vol. 91, pp. 12775–12779 (1994)). pCVF65/9 spans the CVF cDNA sequence from bp 849 to bp 3350 of the CVF cDNA sequence.

First the insert of λgt11-clone CVF72 was subcloned into pUC18 vector: λ-DNA was prepared using standard methods from CVF72 and digested with SacI and KpnI. A resulting 4 kb fragment with 1 kb vector sequences on each site of the CVF insert was separated by agarose gelelectrophoresis, eluted from the gel, ligated into SacI, KpnI-digested pUC18 and transformed into E. coli DH5α resulting in the plasmid construct pCVF72. pCVF72 was digested with Ecl136II and BanII, treated with mungbean nuclease, relegated and transformed into E. coli DH5α. This procedure removed the λ-vector sequence and the CVF signal sequence from the 5'-end of the CVF insert and generated a new Ecl136II-site at the 5' end of the CVF cDNA sequence. This plasmid construct was named pCVF72mut.

The plasmid clones pCVF65/9 and pCVF106 were both digested with SalI and MunI. The proper fragments were separated by agarose gelelectrophoresis, eluted from the gel, ligated together and transformed into E. coli DH5α resulting in the plasmid construct pCVF-MK1.

For the construction of pCVF-FL3Δ, pCVF-MK1 was digested with BamHI and NotI and treated with CIAP. The 4.3 kb CVF fragment spanning bp 1711 to the end of the CVF sequence was separated by agarose gelelectrophoresis and eluted from the gel. pCVF72 was digested with DraI. DraI digests the pUC18 vector about 1 kb upstream of the CVF insert creating a blunt end. Subsequently, the construct was digested with BamHI, the proper fragment separated by agarose gelelectrophoresis and eluted from the gel. This fragment was ligated to the pCVF-MK1 fragment. An ATP-concentration of 5 mM prevents dimerization. The resulting fragment was digested with SalI, subcloned in NotI/SalI precut psportI vector and transformed into E. coli DH5α resulting in the vector pCVF-FL3. To Media Grace's insect medium (T. D. C. Grace, Establishment of four strains of cells from insect tissues grown in vitro, *Nature*, vol. 195, pp. 788–789 (1962)) is the most common for growth of lepidopteran cells. TMN-FH medium (W. F. Hink, Established insect cell line from cabbage loopers *Trichoplusia ni, Nature*, vol. 226, pp. 466–467 (1970)) is Grace's basal medium supplemented with lactalbumin hydrolysate and yeastolate. Cell culture grade fetal bovine serum (FBS) is added to 10% (v/v) to make complete TNM-FH. Complete TMN-FH containing 50 μg/ml gentamicin sulfate was purchased from BioWhittaker. Protein-free medium was purchased from BioWhittaker (Insect xpress). 10 μg/ml gentamycin (Gibco BRL) was used routinely in the medium of stock cultures. The addition of 2.5 μg/ml amphotericinB ("Fungizone", Gibco BRL) is optional and is not done routinely.

Sf9 cells are shear sensitive and can be damaged permanently by handling during routine subculturing. When the surfactant, Pluronic F-68 (Gibco BRL) is added to a final concentration of 0.1% (w/v), shear sensitivity is significantly reduced. Especially for shaker-cultures and for culturing cells in serum-free medium, Pluronic F-68 is used.

Culturing Insect Cells

Carbon dioxide is not required. Cells are maintained at a constant 27±1.0° C. For expression of recombinant protein, the incubation temperature should be a constant 27±0.1° C. For monolayer cultures a B6120 Incubator (Heraeus), and for suspension an incubation skaker (Innova 4300, New Brunswick Scientific) with digital temperature control were used.

Fresh cell culture medium should be equilibrated to room temperature before use. As the cells divide, some might be either loosely attached or suspended in the medium ("floaters"). This is a normal occurrence and is often seen in older cultures and cultures which are "overgrown." If "floaters" constitute more than 5% of the culture, the old medium containing the "floaters" is removed and replaced with fresh medium before subculturing.

Cells which take up trypan blue are considered nonviable. Sf9 cell density is determined using a hemacytometer (Neubauer, Germany). Cell viability can be checked by mixing 10 μl of trypan blue (0.4% stock solution made up in buffered isotonic salt solution, pH 7.2) and 10 μl of cells and examining under a microscope at low magnification. Cell viability should be at least 98% for healthy log-phase cultures.

Population doubling times for these cells will vary depending on growth conditions; as a general guide, healthy suspension cultures double in 18–22 hours. If cell doubling time exceeds 24 hours then there may be a problem with the cell viability, media, temperature, oxygenations etc. Cells may be spun down at 1200 rpm for 10 minutes and resuspended in fresh media at a density of $1 \times 10^6$ cells/ml.

Thawing Sf9 Cells

A vial containing Sf9 insect cells is removed from liquid nitrogen and rapidly thawed with gentle agitation in a 37° C. water bath. When the contents are almost thawed, the outside of the vial is quickly decontaminated by treating with 70% ethanol. The vial is dried, and the 1 ml cell suspension is directly transfered into 4 ml of cold (+4° C.) complete TNM-FH media in a pre-wet 25 $cm^2$ flask. The flask is transferred to a 27° C. incubator and the cells are allowed to attach for 30–45 minutes. Thawed cells do not always appear round; some may be amorphous or have a "wrinkled" appearance. In additions there is usually a significant portion of debris associated with the cells.

Moreover, some of the cells will not attach. Nonattached cells are termed "floaters" and should represent no more than 5% of the flask culture population when the cells are property maintained. The debris and floaters are reduced when cells are subcultured.

After the cells are attached, the media and any floaters are gently removed and transfered to a fresh 25 $cm^2$ flask as a back up. 5 ml of fresh 27° C. media are added to the first flask, and both flasks flasks are incubated at 27° C. 24 hours later, the media in both flasks are changed. Viability of the cells will be greater than 70% when revived in this manner. The cells should be checked daily until a confluent monolayer has formed. Once a confluent monolayer has formed, cells can be subcultured.

Culturing Sf9 Cells in Monolayer Culture

All medium is removed from a confluent 175 $cm^2$ flask and 10 ml of fresh media are added (2 ml for a 25 $cm^2$ flask). To dislodge the cells, the flask is placed on end, the medium is drawn into a sterile pipette and rapidly discharged from the pipette while sweeping the tip of the pipette across the monolayer from side to side. The procedure should start at the bottom and end at the top of the flask. Alternatively, a soft cell scraper (Nunc #179707) can be used to dislodge the cells.

The 10 ml (2 ml) of culture produced should not be split in a ratio higher than 7. For a new culture, flask 2.0 ml (0.5 ml) of the culture are transfered into a new 150 $cm^2$ flask containing 25 ml of fresh medium. The flask is gently rocked to wet the growth surface and distribute cells evenly. It is incubated at 27° C., and cells are allowed to grow to confluency.

It is important that cells are not passaged before confluency as they may be more difficult to dislodge, causing decreased viability.

Culturing Sf9 Cells in suspension Culture

The cultures obtained from 3 to 4 confluent 175 $cm^2$ flasks are combined into a 1000 ml spinner flask. The total medium volume in the spinner flask should be at least 100 ml at starting time, and the cell density should be at about $1 \times 10^6$ cells/ml. The 100 ml spinner is incubated at 27° C. with constant stirring at 80 rpm. Volumes >100 ml are stirred at 100–120 rpm in the presence of 0.1% Pluronic F-68 to increase aeration by diffusion and to provide protection from shearing.

The viability of the cells is checked every 24 hours. Optimally, the cell density should be about $1 \times 10^6$ cells/ml with a viability of >98%. When the cells reach a density of ~$2 \times 10^6$ cells/ml, an equal volume of fresh medium is added, thus dropping the cell density to $1 \times 10^6$ cells/ml again. This process is continued until reaching a 500 ml of culture at a density of ~$2 \times 10^6$ cells/ml. This culture is now ready for infection and large scale production of recombinant protein. For routine maintenance, spinner cultures should be subcultured when the cell density reaches about ~$2.5 \times 10^6$ cell/ml. Cells should be subcultured before their density reaches $4 \times 10^6$ cell/ml. However, the density of the cells should not drop below $1 \times 10^6$ cell/ml.

Adapting Sf9 Cells to Serum-free Conditions

Sf9 cells may be slowly adapted to serum-free medium by slowly decreasing the ratio of TMN-FH to protein-free medium stepwise. First, an almost confluent plate of Sf9 cells is split and two thirds TMN-FH/one third of protein-free medium. is added to the plate. Two passages later, the medium is changed to half and half TMN-FH and protein-free medium. Another two passages later, the ratio is changed to one quarter TMN-FH and three quarters of protein-free medium. After this, the medium is changed to 10% TMN-FH and 90% protein-free medium. Finally, pure protein-free medium can be used. Two to three passages on every step of this procedure should be allowed. Cells seem to be more healthy and grow quicker using this gentle adapting procedure instead of a rapid one.

Freezing Sf9 Cells from Complete Medium

Cells must be frozen in logarithmic growth phase ($1.0–2.5\times10^6$ cells/ml) at 98% viability. Cells are removed from flasks and separated by centrifugation at 1200 rpm for 10 minutes (Sorvall RC-5B centrifuge with an SS-34 rotor, or equivalent).

The cells are gently resuspended in a volume that will result in a cell density of $1\times10^7$ cells/ml of 90% fetal bovine serum, 10% dimethylsulfoxide (DMSO) and aliquoted into cryogenic tubes. The tubes are stored at $-20°$ C. for 1 hour and then transferred to an ultra-low freezer ($-80°$ C.) overnight. The tubes are then transferred to liquid nitrogen for storage.

Freezing Sf9 Cells from Serum-free Medium

Cells are ready to freeze as soon as they are dividing regulary. Cells are detached from the flask by gentle sloughing with medium from a sterile pasteur pipet. Mid to late logarithmic cells (80–90% confluency, 2–3 days old) with a viability of $\geq90\%$, as determinated by trypan blue dye exclusion, are recovered by centrifugation (1200 rpm, 5 minutes). The old (conditioned) medium should be saved. The cell pellet is resuspended to a cell density of $3\times10^6$ cells/ml in ice-cold, sterile, filtered freezing medium consisting of 45% conditioned medium, 45% fresh growth medium, and 10% dimethylsulfoxide (DMSO). Cells are then placed at $20°$ C. for 1 hour, transferred to an ultra-low freezer ($-80°$ C.) overnight and finally stored in liquid nitrogen.

1.4.3. Production of Recombinant Virus

Figure 13:
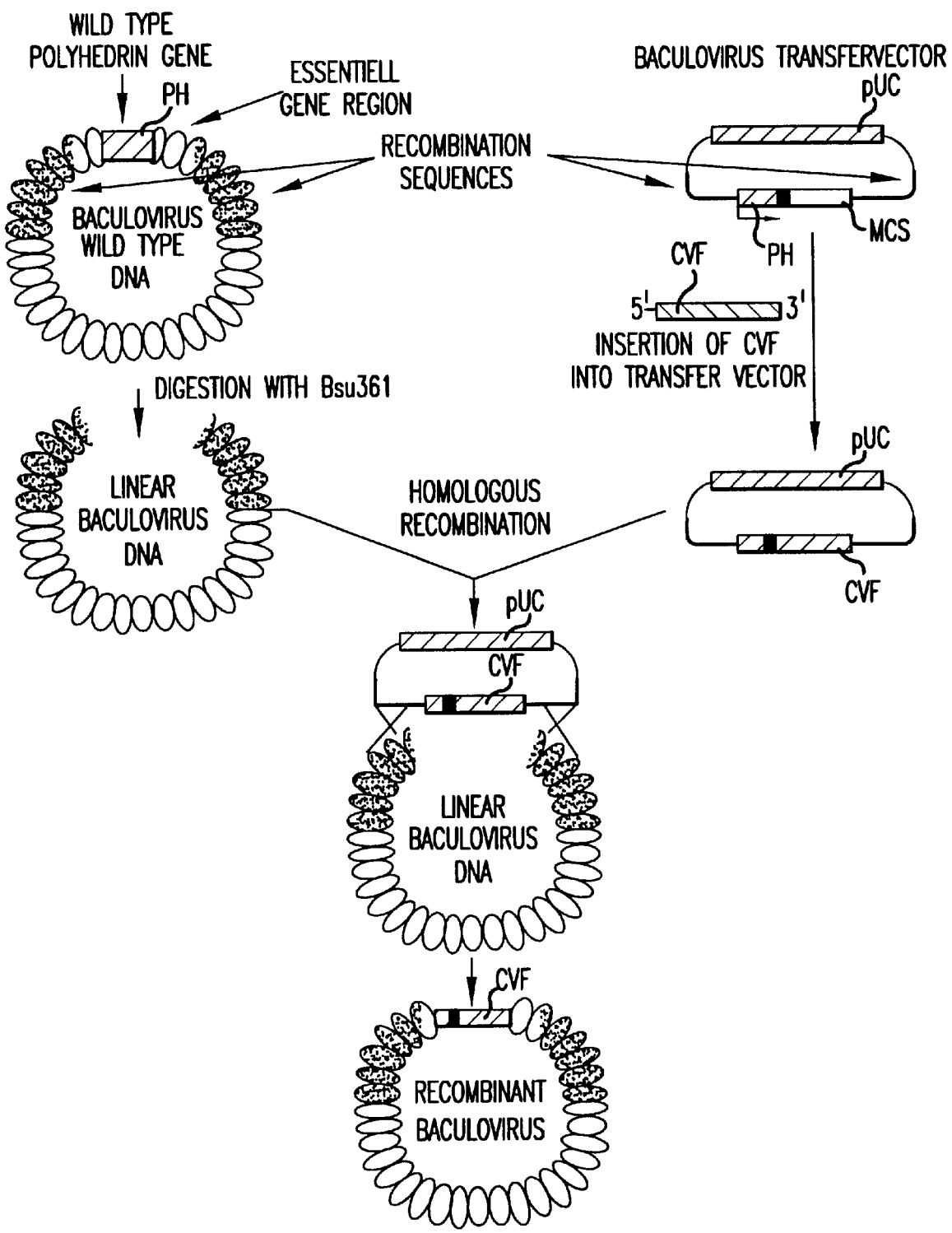
FIG. 13 is a schematic diagram outlining the strategy for polyhedrin-directed expression of recombinant proteins. The nonessential polyhedrin gene and viral flanking sequences are cloned into a plasmid vector. The polyhedrin gene promoter is modified for the insertion of foreign genes to produce polyhedrin-fused or nonfused proteins. The transfer vector containing the foreign gene is cotransfected with linearized wild-type Baculovirus DNA into insect cells. In a fraction of the transfected cells, the polyhedrin gene will be replaced with the recombinant DNA via homologous recombination. Recombinant virus is purified by visual screening of a plaque assay, where recombinant plaques are morphologically distinct from wild-type plaques.

Like many other eukaryotic systems, the BEVS has historically been less convenient and much more time-consuming than bacterial expression systems, especially the construction of the recombinant viruses. This limitation was largely overcome by the development of viruses having Bsu36I restriction sites positions within the essential gene, ORF1629, downstream of the AcNPV polyhedrin gene, and in the upstream ORF603, such that digestion releases a fragment containing a sequence necessary for virus growth. The necessary ORF1629 sequence is repaired and supplied by the transfer plasmid used for cotransfection. See: P. A. Kitts, et al, *BioTechnique*, vol. 14, pp. 810–817 (1993). The vast majority of survivors of cotransfection contain the repaired virus with the target gene, thus minimizing the need to screen large numbers of viruses. FIG. 13 summarizes this method. In addition, the polyhedrin gene in some of these virus strains was replaced with the β-galactosidase gene (lacZ). This facilitates selection between recombinant and wild type virus by using the chromogenic substrate X-gal. β-galactosidase expressing viruses will result in blue plaques during virus purification. Recombinant viruses will remain colorless. This "wild-type" virus is named wild-type (lacZ). Wild-type Viral DNA Isolation and Linearization Purification of Extracellular Virus DNA Relatively pure viral DNA can be obtained from extracellular virus particles (ECV), which are separated from infected cell culture medium by centrifugation. *Spodoptera frugiperda* (Sf9) cells infected with AcMNPV (at $2\times10^6$ cells/ml) will yield about 1 μg of purified ECV DNA per ml of culture medium after 5–7 days p.i. The major problems encountered during purification are degradation of the DNA by mechanical shearing and contamination by nucleases. Also, if the DNA concentration is too high during purification, much of it can be lost during phenol extraction. These difficulties can be avoided with the following procedure adapted from Smith, G. B., and Summers, M. D. (G. E. Smith et al, *Virology*, vol. 123, pp. 393–406 (1982)).

Preparation of AcMNPV DNA

Approximately 500 ml of infected Sf9 cells (at $2\times10^6$ cells/ml) are required for the DNA preparation. For the infection, the cells are pelleted in a sterile tube by spinning for 5–10 minutes at 1000 rpm. The amount of titered virus needed to infect the cells at a Multiplicity of Infection (MOI) of 5–10 is calculated:

$$\text{ml of virus} = \frac{\text{MOI (plaque forming units / cell)} \times \text{number of cells}}{\text{titer (pfu/ml)}}$$

The cells are gently resuspended in approximately 10 ml of complete TNM-FH containing the appropriate amount of virus (from the equation above) and incubated for 1 hour at room temperature with gentle rocking. Subsequently, the cells are transferred to a spinner flask with 500 ml fresh, complete TNM-FH to achieve again approximately $2\times10^6$ cells/ml. At 48 or more hours postinfection (hpi) the virus is harvested by pelleting the cells at 10,000 rpm for 10 minutes at $+4°$ C. The virus-containing supernatant is transferred to ultracentrifuge tubes, and the virus is pelleted by spinning at $100,000\times g$ for 30 minutes at $+4°$ C. The viral pellets are resuspend in ~1 ml of 0.1X TE. Half of the virus is overlayed onto each of two linear 25–56% (wt/vol) sucrose gradients prepared in 0.1X TE (typically 11 ml gradients in Beckman SW-41 tubes). The tubes are centrifuged at $100,000\times g$ for 90 minutes at $+4°$ C. Subsequently, the broad viral band is removed using a Pasteur pipette. The sucrose is diluted by adding at least 2 volumes of 0.1X TE, and the virus is repelleted by spinning for 60 minutes at $100,000\times g$.

The virus is resuspended in 4.5 ml Extraction Buffer (0.1 M Tris, pH 7.5, 0.1M $Na_2EDTA$, 0.2M KCl), and the sample is digested with 200 μg proteinase K for 1–2 hours at $50°$ C. Subsequently, 0.5 ml of 10% Sarkosyl are added and incubated at $50°$ C. for at least two hours (or overnight, if convenient). This solution is extracted twice with phenolchloroform/isoamyl alcohol (25:24.1). To minimize shearing of the viral DNA, extraction is performed by gently inverting the tubes just fast enough to mix the phases for several minutes. The phases are separated by low speed centrifugation and the aqueous phase is carefully removed by using a wide mouth 5 or 10 ml pipette. 10 ml of cold 100% ethanol are added to precipitate the viral DNA, and it is incubated at $-80°$ C. for 30 minutes (or overnight at $-20°$ C. if the DNA is not visible). The DNA is pelleted by spinning at 2500 rpm for 20 minutes, washed once with cold 90% ethanol, and resuspended in 0.1X TE. To facilitate the resuspension, incubation at $65°$ C. for about 10 minutes or overnight at $+4°$ C.: might be necessary.

Linearization of Wild-type Baculovirus DNA

Wild-type (lacZ) viral DNA is prepared as described above. 10 μg of viral DNA are incubated with 20 u of Bsu36I (New England Biolabs) for 2 hours at $37°$ C. Subsequently, another 20 u of Bsu36I are added followed by incubation overnight at $37°$ C. After inactivating the enzyme at $70°$ C. for 15 minutes, the digest was stored at $4°$ C. Aliquots of the digested and undigested viral DNA were run on a 0.5% agarose gel to check that the digest is complete. Uncut (circular) viral DNA does not enter the gel. For the digested viral DNA, a 3.3 kb band should be visible. At high concentrations, an additional 1.1 kb band can be detected.

Calcium Phosphate Mediated Transfection of Sf9 Cells

After cloning the CVF-cDNA into the transfer vector, at least 10 μg of highly purified plasmid DNA are prepared using standard techniques. *Spodoptera frugiperda* cells are sensitive to some contaminants found in crude plasmid preparations, which cannot be removed by phenol extraction or ethanol precipitation. A consistently reliable method for plasmid purification is CsCl-ethidium bromide gradient centrifugation. Impure preparations of plasmid DNA are toxic to the cells, and many cells may lyse shortly after transfection. This results in an apparently lower recombination frequency and increased difficulty in detecting recombinant viruses. In addition, the viral DNA quality (i.e., minimize nicking and shearing) is important too.

Plasmids containing foreign genes are cotransfected with wild-type (lacZ) AcMNPV DNA by the calcium phosphate precipitation technique, (F. L. Grahm et al, *Virology*, vol. 52, pp. 456–467 (1973)) as modified for insect cells (J. P. Burand, et al, *Virology*, vol, 101, ppg. 286–290 (1980); E. B. Carstens, et al, *Virology*, vol. 101, pp. 311–314 (1980); and K. N. Potter, *J. Invertebr. Pathol.*, vol. 36, pp. 431–432 (1980)). The foreign gene is transferred to the AcMNPV genome in a subpopulation of the transfected cells by homologous recombination.

$2 \times 10^6$ Sf9 log Phase Sf9 cells ($1.5-2.5 \times 10^6$ cells/ml; ≧98% viable) are seeded in complete TNM-FH in a 60 mm plate. The cells are allowed to attach for at least 30 minutes. 0.1 μg linearized AcMNPV (lacZ) DNA and 3–5 μg of plasmid DNA (the transfer vector containing the foreign gene) were mixed in a 1.5 ml polypropylene tube in a volume of 10 μl. 0.75 ml of Transfection Buffer are added, and pipetted once to mix. AcMNPV DNA is ~130 kb in length and is therefore very easy to shear. The Transfection Buffer may be stored at +4° C., but should be warmed to room temperature before transfection. The plate is tipped at a 45° angle, and all of the medium is aspirated with care from the cells using a Pasteur pipette. 0.75 ml of TNM-FH complete medium are added. The DNA solution is added dropwise to the cells. Then the plates are incubated at 27° C. on a side/side rocking platform slowly for 4 hours (setting 2.5 for a Bellco #774020020 side/side rocking platform). Following the incubation period, the medium is removed, and the cells are carefully rinsed with fresh complete TNM-FH. 3 ml of complete TNM-FN are added, and the cells are incubated at 27° C. In addition, one plate is infected with wild type virus (positive control), and one plate is just incubated with medium.

The cells are checked 4 days posttransfection to visually confirm a successful transfection. This is done using an inverted phase microscope a 250–400× magnification. Nearly all of the cells infected with wild type virus should contain viral occlusions, which appear as refractive crystals in the nucleus of the insect cell. This sign of infection should be absent for the cotransfected cells since the polyedrin gene is replaced. Other positive signs of virus infection include a 25–50% increase in the diameter of the cells, a marked increase in the size of the cell nuclei relative to the total cell volume (the nuclei may appear to "fill" the cells), and cell lysis and debris. In the late phase of infection, cells start to float. 10–50% of the cells in the cotransfected plate should have these signs.

Plaque Purification of Recombinant Virus

A 5% solution (w/v) of Baculovirus agarose (Invitrogen) in distilled water is prepared and autoclaved to dissolve the agarose and to sterilize the solution. The solution is incubated at 50° C. until needed. Aliquots of 45 ml of TNM-FH complete medium are stored at 50° C. until needed. 10-fold dilutions of virus inoculum (media harvested from transfections) are prepared in the range of the expected titer (1 ml of diluted virus for each plate). It is essential that the viral inoculum is vortexed vigorously prior to the preparation of the dilutions. Routinely, dilutions of $10^{-3}$ to $10^{-5}$ are plated when transfection is performed.

Sf9 cells at a density of $5 \times 10^6$ cells/100 mm plate are seeded in complete medium. Duplicate plates should be used for each virus inoculum to be tested. Plates are rocked at room temperature for at least 30 minutes on a side/side rocking platform in order to distribute the cells evenly. Use a setting of 5 for a Bellco #774020020 side/side rocking platform. The cells should be examined to confirm that they have attached. The plates are removed from the rocker and kept at room temperature for at least 30 minutes before using.

All but 2 ml of medium are removed from the cells once they have firmly attached. 1 ml of each dilution is added dropwise to the appropriately labelled plate. Following addition of the viral dilutions, the plates are incubated at room temperature on a slowly rocking platform for 1 hour (setting of 2.5 for a Bellco #774020020 side/side rocking platform). During this incubation period, a water bath is heated to a temperature of 46° C. and placed in the laminar flow hood. Just prior to the end of the 1-hour incubation, the 5 ml of the autoclaved agarose are added to a 45 ml aliquot of prewarmed medium, mixed, and placed in the 46° C. water bath. When plating involves selection between recombinant and wildtype virus, the chromogenic substrate 5-bromo-4-chloro- 3-indolyl-β-D-galactoside (X-gal) or halogenated indolyl-β-D-galactosidase (Blu-gal, Bluo-gal) is incorporated into this pre-aliquotted medium at a concentration of 150 μg/ml. At the completion of the incubation period, the medium is completely removed from the plates. Then, working from the edge, 10 ml of the agarose/medium mixture are gently poured onto one of the plates from which the medium was removed. Care must be taken not to move move the plates until the agarose has set. The plates are incubated in a humid environment at 27° C. for 5–6 days, or until plaques well-formed. For 60 mm plates, $2 \times 10^6$ cell, an inoculation volume of 1 ml, and an agarose overlay of 4 ml are used.

Trypan Blue overlay

On day 3–5 of the plaque assay, a second agarose overlay containing Trypan Blue is prepared. 1 ml of a sterile 1% Trypan blue solution (equilibrate to 40°–42° C.) is added to 12.5 ml of 1% agarose (also equilibrate to 40°–42° C.) and mixed well. The plates are overlayed with 1 ml of the Trypan Blue/agarose mixture per 60 mm plate (2 ml per 100 mm plate) and incubated overnight at 27° C. to allow the dye to diffuse into the dead cells. The number of blue plaques is counted to determine the viral titer. See H. Piwinica-Worms, in *Current Protocols in Molecular Biology, Supplement* 10, F. M. Ausubel et al Eds., John Wiley, New York, 1990.

The Trypan Blue method is useful for titering virus, but is not useful for selecting a recombinant plaque from a plate with wild-type and recombinant plaques—there is no distinction between plaque types. In addition, Trypan Blue is a known mutagen and not recommended for isolating recombinant virus.

Neutral Red Overlay

On day 6–7 of the plaque assay, a second agarose overlay containing Neutral Red is prepared. 50 μl of a sterile Neutral Red solution (20 mg/ml) is added to 10 ml of 1.5% agarose (equilibrate to 46°–50° C.), mixed well, and kept at 46°–50° C. until ready to use. The plates are overlayed with 2 ml of the Neutral Red/agarose mixture per 100 mm plate and incubated overnight at 27° C. to allow the dye to diffuse into the dead cells. The plaques will appear as morphologically distinct opaque areas on the pink/red monolayer. The number of plaques is counted to determine the viral titer.

The titer (pfu/ml) is calculated as follows:

$$pfu/ml = (1/dilution) \times \text{number of plaques}.$$

The following formula can then be used to determine the Multiplicity Of Infection (MOI):

$$\text{ml of inoculum needed} = \frac{\text{MOI (pfu/cell)} \times \text{number of cells}}{\text{titer of virus (pfu/ml)}}$$

Neutral Red is a known mutagen and not recommended for isolating recombinant virus.

Visual Screening for Recombinant Plaques

When plaques are distinct (at least 6 days postinfection), the plates are examined using a dissecting microscope with a magnification of 30–40×. Plates which have been infected with a dilution of virus resulting in well-separated plaques in the parallel Neutral Red overlay are investigated first.

The plate is placed upside down on a nonreflective dark surface (e.g., black velvet or paper) and illuminated from the side using an intense light source (slide projector). The angle of the light is adjusted until the plaques can be observed (usually, a 45° angle or greater is best). Against a black, nonreflective background recombinant plaques will be of a dull milky-white color. Non-recombinant wild-type (lacZ) plaques are blue in color when the chromogenic substrate X-gal is added to the agarose. Plaques from both the recombinant and the wild-type (lacZ) strain do not develope polyhedrin occlusion bodies. Recombinant and wild-type (lacZ) plaques can not be distinguished without X-gal. Occlusion body positive wild-type plaques will not become blue but look shiny, almost crystal-like against a black, nonreflective background.

If plaques are dubious, the plate is scanned at a magnification of 30–40× and any plaques suspected to be recombinant, occlusion body negative are circled. Circled plaques are reexamined under an inverted phase microscope at 200–400×. Viral plaques are observed as a clear area in the cell monolayer which is ringed by infected cells which are morphologically distinct from the uninfected cells. They are generally larger in diameter, display at marked increase in the size of the nuclei relative to the total cell volume and show signs of cell lysis. The entire plaque area should be examined for the presence or absence of occlusion bodies. To avoid several rounds of screening, it is important that only recombinants are selected. Blue color of wild-type (lacZ) sometimes developes late. The sligthest hint for blue color under the microscope should be considered.

When several putative recombinant plaques have been located, the circled plaques are checked again using a dissecting scope. A tiny dot is placed within each circle, directly over the plaque to be picked. See: R. Dulbecco, et al, *Proc. Natl. Acad. Sci. U.S.A.*, vol. 38, pp. 747–751 (1952); W. F. Hink, et al, *J. Invertebr. Pathol.*, vol. 22, pp. 168–174 (1973); and H. H. Lee, et al, *J. Virol.*, vol. 27, pp. 754–767 (1978).

Purification of the Recombinant Virus

Several 25 cm$^2$ plates are seeded with 1×10$^6$ Sf9 cells each. The total volume of the plate should not exceed 3 ml.

Using a sterile pasteur pipette and bulb, the agarose over the recombinant plaque is carefully removed, and the agarose plug containing the plaque is transferred to one of the plates. These steps are repeated for all putative plaques.

Another plate acts as a cells-only control. The plates are incubated at 27° C. for 4 days. If cells grow confluent and start to float, the floaters and the medium are transferred to a new 75 cm$^2$ plate. On day 3, the plates are visually screened for the presence of occlusion bodies. Any plate containing occlusion bodies is not plaque pure and requires additional rounds of purification.

The plates that are occlusion-negative should be kept and incubated at 27° C. until all of the cells lyse. The medium from these wells is harvested and stored at +4° C. This is the P1 virus stock for the generation of large-scale, high-titer virus stock. Each P1 stock is checked for the presence of wild-type (lacZ) by a plaque assay including X-gal selection. Only P1 stocks that are neither occlusion positive nor develope blue plaques in a plaque assay can be considered recombinant. An aliquot of the P1 may be used to carry out PCR analysis of the putative recombinant virus or Western analysis for the recombinant protein.

Virus Propagation

Preparing Large-Scale, High-Titer Virus Stocks once a recombinant virus has been identified, 100 μl of the P1 viral stock each are added to two 25 cm$^2$ flasks seeded with 2×10$^6$ Sf9 cells. The flasks are incubated at 27° C. for 4–5 days, or until the cells are 90% lysed. This is the P2 inoculum. Two 1 ml aliquots of the P2 virus stock are removed. One may be placed at −80° C. for long-term storage, while the other is stored at +4° C. The remaining P2 virus stock obtained from the cultures in the two 25 cm$^2$ flasks is used to infect 500 ml of Sf9 cells seeded at a density of 1.5–2.5×10$^6$ cells/ml. Cells are transferred in fresh medium to a spinner flask, and virus is added. 5 ml of the cell/virus suspension is transferred to a 25 cm$^2$ flask to monitor the infection process. The culture is incubated at 27° C. with constant stirring (120 RPM) for 5–7 days. The progress of the infection is regularly checked by observing the 25 cm$^2$ flask, or alternatively, by examining aliquots of the infected cell suspension with a microscope. When cells are 90% lysed, the culture medium (for future inoculum or protein purification) is collected by centrifugation, and the supernatant is transferred to a sterile bottle. This is now the P3 virus stock which can be titered (plaque assay for dilutions 10$^{-5}$ through 10$^{-8}$ as described above) and used to determine a time course of protein expression. The P3 virus stock is stored at +4° C.

It is recommended that all stocks be protected from light in order to ensure maintenance of titer (*Bio/Techniques*, vol. 116, no. 3, pp. 508–513).

Time course for Production of Recombinant Protein

To optimize the level of protein production it is essential that an initial time course of expression be carried out. A 100 ml spinner flask is seeded with 50 ml of Sf9 cells at a density of 2×10$^6$ cells/ml and infected with P3 high-titer viral stock at a MOI of 5. 1 ml aliquots of cells are removed every 12–24 hours over a period of 5 days and analyzed for the presence of the protein of interest. When the time point at which maximal expression is obtained, large-scale protein expression can be carried out Seeding Densities The chart below gives approximate seeding densities for typical vessel sizes. Infection at these densities will usually give high virus titers (≧1×10$^8$ PFU/ml).

| Type of Vessel | Cell Density | Minimum Virus Volume | Incubate in Final Volume |
| --- | --- | --- | --- |
| 96-well plate | 2.0 × 10$^4$/well | 10 µl | 100 µl |
| 24-well plate | 6.0 × 10$^5$/well | 200 µl | 500 µl |
| 60 mm$^2$ plate | 2.5 × 10$^6$/flask | 1 ml | 3 ml |
| 25 cm$^2$ flask | 3.0 × 10$^6$/flask | 1 ml | 5 ml |
| 75 cm$^2$ flask | 9.0 × 10$^6$/flask | 2 ml | 10 ml |
| 150 cm$^2$ flask | 1.8 × 10$^7$/flask | 4 ml | 20 ml |
| 150 cm$^2$ flask spinners (all) | 1.5–2.0 × 10$^6$/ml | (based on MOI*) | (based on size) |

(*MOI = 0.5–1.0 for high-titer stocks and 5.0–10.0 for time course/protein expression).

1.4.4 Production of Recombinant ProCVF

Large Scale Expression of Recombinant ProCVF

For large scale expression of recombinant proCVFf,a 500 ml culture in 1 liter flasks of protein-free cultured Sf9 insect cells with a density of ~2×10$^6$ cells/ml are infected with a baculovirus strain recombinant for CVF at a Multiplicity of Infection (MOI) of 5–10. The cultures obtained from 3 to 4 confluent 175 cm$^2$ flasks are combined into a 1000 ml spinner flask. The total medium volume in the spinner flask should be at least 100 ml at starting time, and the cell density should be at about 1×10$^6$ cells/ml. The 100 ml spinners are incubated at 27° C. with constant stirring at 80 rpm. Volumes >100 ml are stirred at 100–120 rpm in the presence of 0.1% Pluronic F-68 to increase aeration by diffusion and to provide protection from shearing. The viability of the cells is checked every 24 hours. Optimally, cell density should be about 1×10$^6$ cells/ml with a viability of >98%. When the cells reach a density of ~2×10$^6$ cells/ml an equal volume of fresh medium is added, thus dropping the cell density to 1×10$^6$ cells/ml again. This process is continued until reaching a 500 ml of culture at a density of ~2×10$^6$ cells/ml. This culture is now ready for infection and large scale production of recombinant protein.

The amount of titered virus needed to infect the cells at a Multiplicity of Infection (MOI) of 5–10 is calculated: Approximately 500 ml of infected Sf9 cells (at 2×10$^6$ cells/ml) are required for the DNA preparation.

$$\text{ml of virus} = \frac{\text{MOI (plaque forming units / cell)} \times \text{number of cells}}{\text{titer (pfu / ml)}}$$

The progress of the infection is regularly checked every 24 hours by examining aliquots of the infected cell suspension with a microscope. When the cells are 60% lysed (3.5–4 days after infection), the culture medium (for future inoculum or protein purification) is collected by centrifugation, and the supernatant is transferred to a sterile bottle.

Purification of Recombinant ProCVF Using Affinity Chromatography

This method was developed for isolation of recombinant proCVF from insect cell cultures infected with baculovirus strains expressing proCVF with the signal peptide from gp67a glycoprotein. Yields were found to be low for this strain.

At the fourth day of infection, the culture supernatant was collected by centrifugation, and phenylmethylsulfonyl fluoride (PMSF) was added to a final concentration of 2 mM. The supernatant was cooled to 4° C., diluted 1:1 with water, adjusted to pH 7.2, and filtered through a 0.45 µm cellulose acetate membrane (Sartorius). This solution was directly applied to a Highload-S cation exchange column (110×15 mm)(Bio-Rad) equlibrated in 4.3 mM phosphate (pH 7.2). Recombinant proCVF was eluted with a linear (0–300 mM) NaCl gradient. Fractions containing recombinant proCVF were identified by SDS-PAGE and Western blotting, pooled, concentrated, and dialyzed against 4.3 mM phosphate buffer (pH 7.2) using Amicon ultrafiltration system.

5 mg of polyclonal rabbit anti-CVF antibody 1090 were immobilized on NHS-activated Sepharose® High Performance (1 ml HiTrap™ affinity column, Pharmacia) according to the manufacturer's manual. For affinity absorption of recombinant proCVF, the recombinant proCVF pool from above is slowly (1 ml/min) applied to the column using a syringe or, for greater volumes, a peristaltic pump (P1, Pharmacia). The column is intensively washed with buffer A (0.1M Tris-HCl, 100 mM NaCl pH 7.5). Recombinant proCVF is eluted with buffer B (0.1M glycine, pH 2.5), and 0.5 ml fractions are immediately neutralized with 50 µl Buffer C (1M Tris-HCl, pH 9.0). Fractions containing recombinant proCVF were identified by SDS-PAGE and Western blotting and pooled. Purified recombinant proCVF was aliquoted and stored at –20° C.

Purification of Recombinant ProCVF Using Ion-exchange Chromatography

At the fourth day of infection, the culture supernatant was collected by centrifugation, and phenylmethylsulfonyl fluoride (PMSF) was added to a final concentration of 2 mM. The supernatant was cooled to 4° C., diluted 1:1 with water, adjusted to pH 7.2, and filtered through a 0.45 µm cellulose acetate membrane (Sartorius). This solution was directly applied to a Highload-S cation exchange column (110×15 mm) (Bio-Rad) equilibrated in 4.3 mM phosphate (pH 7.2). Recombinant proCVF was eluted with a linear (0–300 mM) NaCl gradient. Fractions containing recombinant proCVF were identified by SDS-PAGE and Western blotting, pooled, and directly applied to a Highload-Q anion exchange column (5×100 mm) (Bio-Rad) equilibrated in 4.3 mM phosphate (pH 7.2). Recombinant proCVF was eluted with a linear (0–500 mM) NaCl gradient. Fractions containing recombinant proCVF were identified by SDS-PAGE and Western blotting and pooled. Purified recombinant proCVF was aliquoted and stored at –20° C.

Protein Charaterization Methods

Western Blot Analysis

Cobra venom factor is immunogenic and, therefore, it is fairly easy to generate polyclonal antisera. Antisera has been raised in goats (C.-W. Vogel et al, *J. Immunol Methods*, vol. 73, pp. 203–220 (1984)), rabbits (C. OW. Vogel et al, *J. Immunol Methods*, vol. 133, ppg. 3235–3241 (1984)), and mice (A. H. Grier et al, *J. Immunol.*, vol. 139, pp. 1245–1252 (1987)).

For detection of recombinant cobra venom factor, a polyclonal rabbit anti-CVF antisertun (AK-1900) was used. The antiserum was cleaned and concentrated by fractionated ammonium sulfate precipitation. Cold saturated ammonium sulfate solution was added to the antiserum to 28% saturation, and it was incubated on ice for thirty minutes. Precipitated protein was separated by centrifugation (3000 g, 4° C., 20 min.) and discharged. Ammonium sulfate was added to the supernatant up to a saturation of 50%. Precipitated antibodies were isolated by centrifugation and dissolved in PBS (10 mM sodium phophate, 140 mM NaCl, pH 7.4). The concentrated antibody is used in a dilution of 1:125.

Protein (1 µg) is electrophoresed on SDS-polyacrylamide gels under non-reducing or reducing conditions (U. K. Laemmli, *Nature*, vol. 227, pp. 680–685 (1970)) and electrotransferred onto polyvinylidene difluoride (PVDF) membranes (Millipore, Bedford, Mass.) using CAPS blotting buffer. The membrane is blocked for at least 2 hours in 10%

(w/v) milkpower/TBS. Subsequently, the membrane is washed twice with TBS for 5 minutes each. 20 μl of rabbit antiCVF antibody (AK1900) are added in 25 ml 5% (m/v) milkpower/TBS to the membrane and incubated for 1 hour. The membrane is washed two times with TBS and incubated with 25 ml 5% milkpower/TBS containing 2 μl anti-rabbit alkaline phosphatase conjugate (Sigma). After this, the membrane is washed twice with TBS and once with 0.1 Tris-buffer pH 9.5 (100 mM sodium chloride). The color reaction is performed in the same buffer containing 50 mM magnesium chloride, 250 μl BCIP (0.5% (w/v) in DMF) and 2500 μl NBT (0.1% (w/v) in Tris buffer) until bands become visible.

Assays For Cobra Venom Factor

Two assays have been developed to determine CVF activity. The first assay is based on the anticomplementary activity of CVF. The sample containing CVF (or recombinant proCVF) is incubated with a defined volume of normal serum (human or guinea pig). Subsequently, the remaining complement homolytic activity in the serum is determined in a hemolytic assay that uses sensitized sheep erythrocytes as targets (M. Ballow et al, *J. Immunol.*, vol. 103, pp. 944–952 (1969); C. G. Cochrane et al, *J. Immunol.*, vol. 105, pp. 55–69 (1970).

Sheep erythrocytes from whole sheep blood (Behringwerke) are separated by centrifugation (720 g, 4° C., 10 min.). The supernatant is discharged, and the erythrocytes are washed with GVPS$^{++}$. Centrifugation and washing is repeated three to four time or until the supernatant remains clear. Resuspended erythrocytes are adjusted to a concentration of 5×10$^8$ cells/ml (20 μl lysed 1 ml H$_2$O results in an OD$_{412}$=1.3) and incubated with rabbit anti-sheep antibodies (diluted 1:100, Sigma) at 37° C. for 30 minutes. Subsequently, the antibody-sensitized erythrocytes (ESA) are separated again by centrifugation, washed three times with GVPS$^{++}$ and adjusted to a concentration of 5×10$^8$ cells/ml. 10 μl sample containing CVF (or recombinant proCVF) is incubated with 10 μl serum (guinea pig or human) for an appropriate time (30 minutes to 3 hours) at 37° C. Controls included normal serum only, heat-inactivated serum, heat-treated CVF or heat-treated recombinant proCVF, VPS$^{++}$ buffer only, and 100% lysis using H$_2$O. After the incubation time, 100 μl GVPS$^{++}$ and 30 μl ESA are added and incubated in 2 ml reaction tubes (Eppendorf, round bottom) in a Thermomixer 5437 (Eppendorf) at 37° C. with moderate shaking (#8). The incubation period can vary from 10 minutes to 30 minutes. Lysis in the control reaction with serum only should be about 80% of total lysis. Subsequently, the reaction is stopped by addition of 1 ml GVPS$^{++}$, and unlysed erythrocytes are sedimented by centrifugation (2000 g, 4° C., 2 minutes) and released hemoglobin is spectrophotometrically determinated in the supernatant (412 nm).

A second assay for CVF is based on fluid-phase C5 cleavage and bystander lysis of unsensitized erythrocytes (C.-W. Vogel, et al, *J. Immunol. Methods*, vol. 73, pp. 203–220 (1984)). The sample containing CVF (or recombinant proCVF) is incubated with normal guinea pig serum and guinea pig erythrocytes. Guinea pigs are narcotized with Ketamin and Rumpun. About 2 ml whole blood is taken by heart puncture and added to 1 ml ACD-buffer. The erythrocytes are washed three times with GVPS$^{++}$. Centrifugation and washing is repeated three to four times or until the supernatant remains clear. Resuspended erythrocytes are adjusted to a concentration of 5×10$^8$ cells/ml (20 μl in 1 ml H$_2$O results in an OD$_{412}$=1.3). 20 μl of the CVF containing sample are incubated with 20 μl of normal guinea pig serum and 20 μl of a guinea pig erythrocytes suspension for an appropriate time (30 minutes to 3 hours, depends on CVF concentration). Controls include normal serum only, heat-inactivated serum, heat-treated CVF/recombinant proCVF, addition of EDTA or Mg-EDTA, addition of specific CVF-inhibitor from cobra serum, VPS$^{++}$ buffer only, and 100% lysis using H$_2$O. Subsequently, the reaction is stopped by the addition of 1 ml GVPS$^{++}$ and unlysed erythrocytes are sedimented by centrifugation (2000 g, 4° C., 2 min.) and released hemoglobin is spectrophotometrically determined in the supernatant (412 nm).

N-Terminal Sequencing

N-terminal sequencing was performed on an ABI-476A Protein Sequencer. The N-terminus was sequeced following SDS-PAGE and electroblotting to ProBlott membrane and was found to be the same as that of the CVF α-chain (or the N-terminus of proCVF). This demonstrates that the signal peptide is probably removed, but that there is nearly no (<10%) cleavage in the (Arg)$_4$ linkage between the CVF α- and γ-chain.

Glycosylation Analysis

Glycosylation is analysed using DIG Glycan Differentiation Kit (Boehringer Mannheim), based on lectin affinity staining. This kit is based on detection of carbohydrate structures with lectins of different carbohydrate specifity, listed in Table 1. The lectins are digoxigenin labeled and are detected by an anti-digoxigenin antibody conjugated with alkaline phosphatase. Alkaline phosphatase triggers a color reaction with chromogenic substrates.

Protein (1 μg) is electrophoresed on SDS-polyacrylamide gels under non-reducing or reducing conditions (U. K. Laemmli, *Nature*, vol. 227, pp. 680–685 (1970)) and electrotransferred onto polyvinylidene difluoride (PVDF) membranes (Millipore). Blocking and detection of carbohydrate structures is performed according to the manufacturer's guidelines: All steps are performed at room temperature with moderate shaking. Only the color reaction is performed without shaking. The membrane is blocked for at least 30 minutes. Subsequently, the membrane is washed twice with TBS for 10 minute each, and once with TBS containing 1 mM magnesium chloride, 1 mM calcium chloride, and 1 mM manganese chloride (TBS*). The appropriate amount of lectin is added in 10 ml TBS* to the membrane and incubated for 1 hour. The membrane is washed three times with TBS and incubated with 10 ml TBS containing 10 μl anti-digoxigenin alkaline phosphatase conjugate. After this, the membrane is washed twice with TBS and once with 0.1 Tris-buffer pH 9.5 (50 mM magnesium chloride, 100 mM sodium chloride). The color reaction is performed in the same buffer containing 37.5 μl BCIP (50 mg/ml) and 50 μl NBT (75 mg/ml) for about 10 minutes.

For dot-blot analysis, 3 μl protein solution (1 μg) was directly applied to hydrophilic cellulose nitrate, membranes (BA-S 83 supported, Schleicher & Schüll). This method in combination with a multiple incubation chamber (PR 150 Mighty Small Deca-Probe, Hoefer) is preferred for parallel analysis of several proteins with several different lectins. After sample application and blocking, the membrane is transferred into the incubation device. That divides the membrane into ten isolated lanes allowing parallel side-by-side incubation with up to ten lectins without the need to slice it into strips. The glycosylation analysis is performed as described above. Only 2 ml of lectine solution are necessary for each chamber.

After incubation with the lectins and a primary washing step the incubation device is not necessary anymore. It is more convenient to handle the following incubation steps with the non-separated membrane. All steps are performed according to the manufacturer's guidelines.

TABLE 1

| Lectin | Specificity |
| --- | --- |
| ConA<br>*Concanavalia ensiformis* agglutinin | α-Man<br>binds to mannose containing carbohydrates |
| GNA<br>*Galanthus nivalis* agglutinin | Man α(1-3) Man (α1-3 α1-6 α1-2)<br>binds to terminal mannose linked to mannose, indicating high-mannose type structure |
| SNA<br>*Sambusus nigra* agglutinin | Neu NAc α(2-6) Gal/GalNAc<br>binds to sialic acid linked to galactose in both N- and O-glycans |
| MAA<br>*Maachia amurensis* agglutinin | Neu NAc α(2-3) Gal<br>binds to sialic acid linked to galactose in both N- and O-glycans |
| DSA<br>*Datura stramonium* agglutinin | binds to Galβ(1-4) GlcNAc in complex N-glycans and GlcNac-Ser/Thr core in O-glycans |
| PNA<br>*Peanut agglutinin* agglutinin | Galβ(1-3) GlcNAc<br>binds to core disaccharide of O-glycans |

2. Results

Expression and Purification of Recombinant ProCVF

Cell pellets and supernatants of insect cell cultures infected with CVF containing recombinant baculoviruses were analyzed by Western blot analysis using a polyclonal anti-CVF antiserum. For recombinant proCVF expression, an anti-CVF reactive 200 kDa protein could be detected which was absent in wild type-baculovirus infected cells or uninfected cultures.

Figure 14:
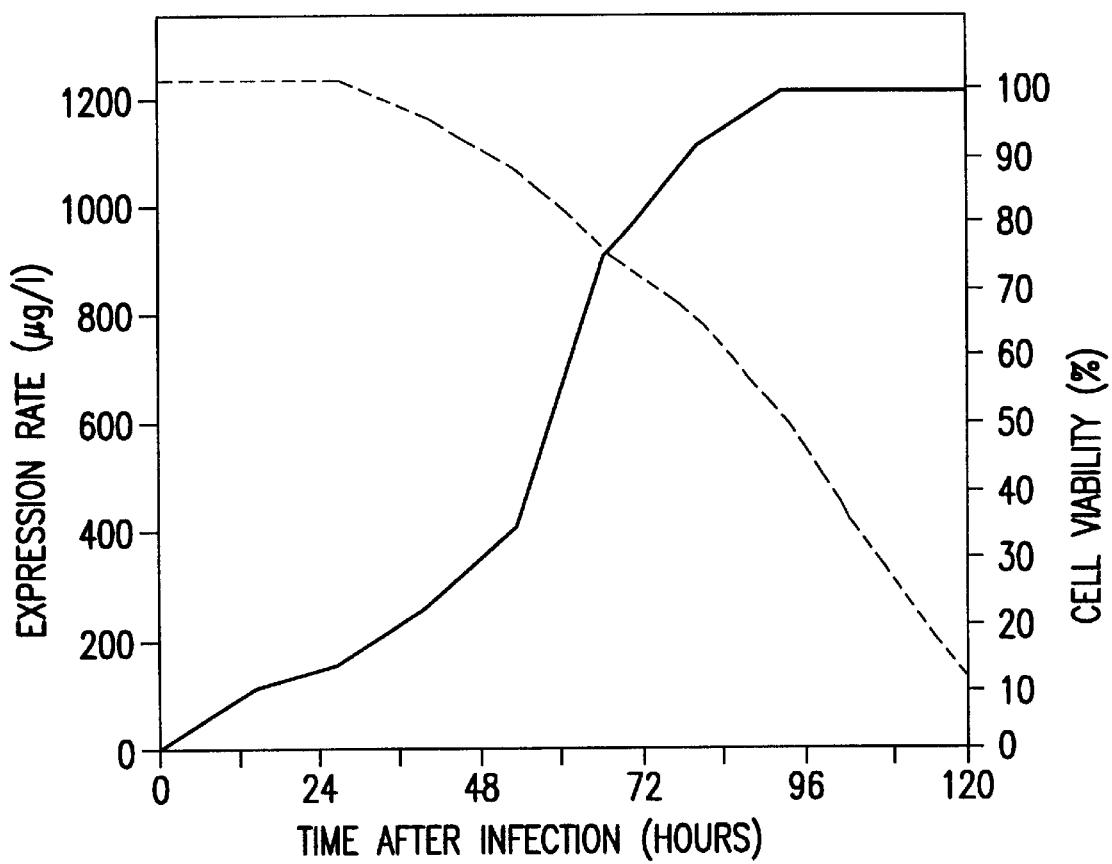
FIG. 14 graphically illustrates the time course of expression rate (left axis) and cell viability (right axis)

The highest amount of recombinant proCVF is obtained by expressing full-length CVF cDNA with its natural secretory signal sequence (Ac-CVF-secr and Ac-CVF-secr-3'His) in serum-free cultured Sf9 insect cells. Maximum expression rates were about 2 mg/l recombinant proCVF. Optimal expression was performed for 4 days at 27° C. in monolayer culture or spinner flasks with a multiplicity of infection (MOI) of 5–10. After 4 days, recombinant proCVF expression leveled. Prolonged expression times did not increase the yield of recombinant protein, but insect cells started to lyse intensively making purification more difficult (FIG. 14). Recombinant proCVF was purified by two-step ion-exchange chromatography. With this procedure, the yield of recombinant proCVF was approximately 1 mg from 1 liter of culture supernatant and the purity was >90%.

Chain Structure of Recombinant ProCVF

Figure 15:
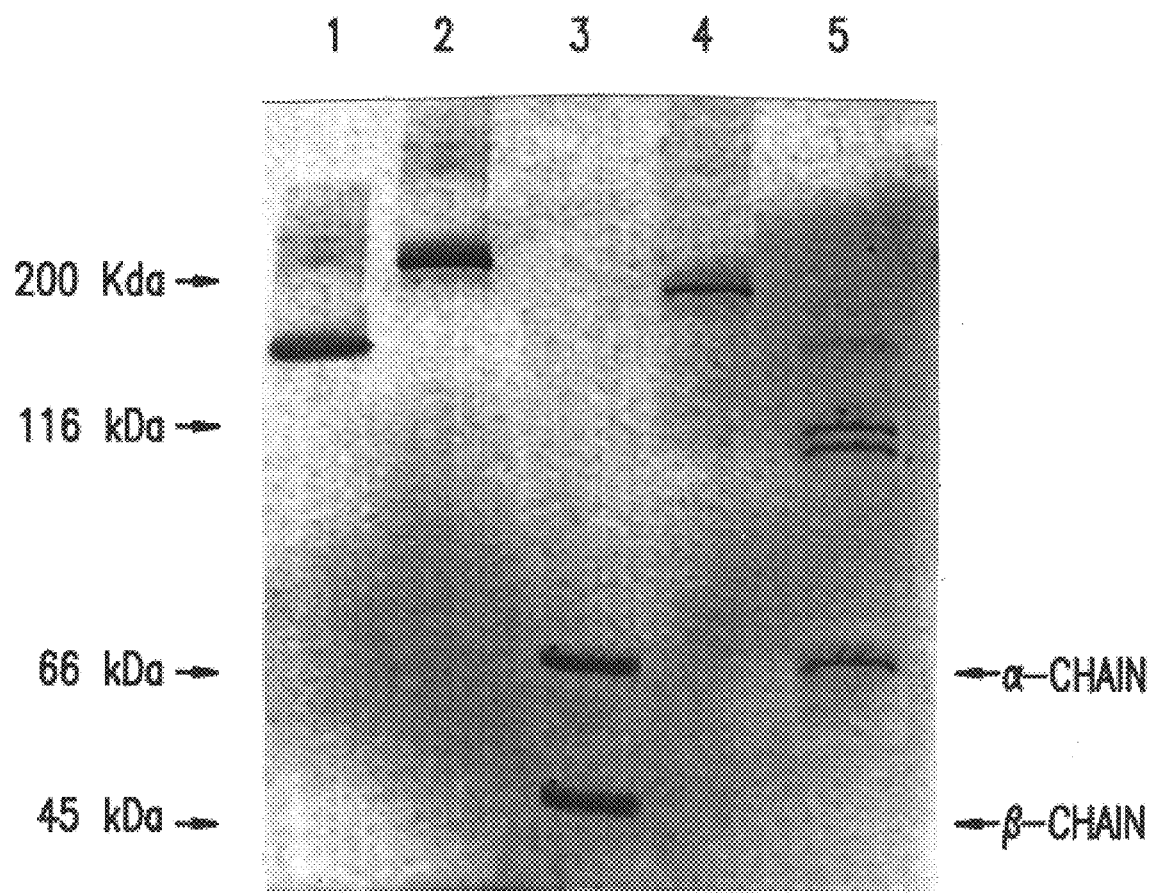
FIG. 15 shows the results of the electrophoresis of recombinant proCVF under reducing conditions: coomassie blue stained 7.5% PAGE gel; lane 1: natural CVF (non-reduced form); lane 2: recombinant proCVF (non-reduced form), lane 3: natural CVF (reduced form, γ-chains (32 kD) are out of range); lane 4: recombinant proCVF (reduced form); lane 5: recombinant proCVF (reduced form, after prolonged incubation)
Figure 17:
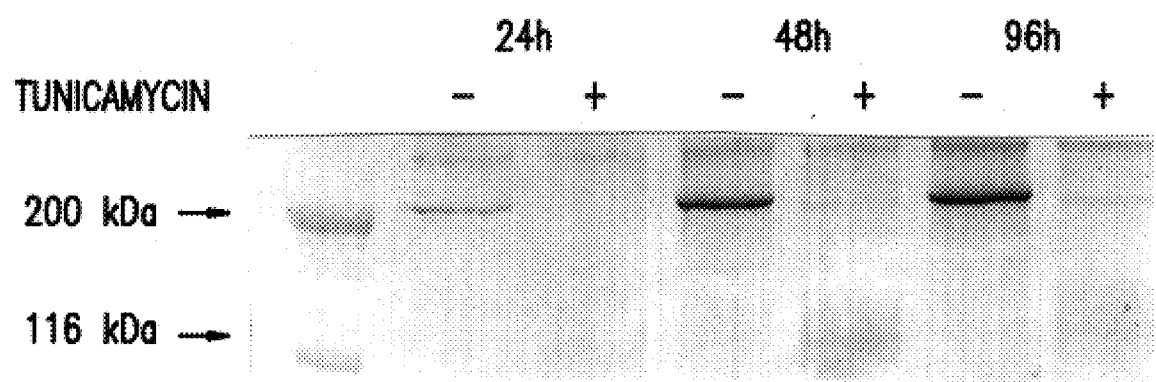
FIG. 17 illustrates the effect of tunicamycin on the expression of recombinant proCVF.
Figure 18:
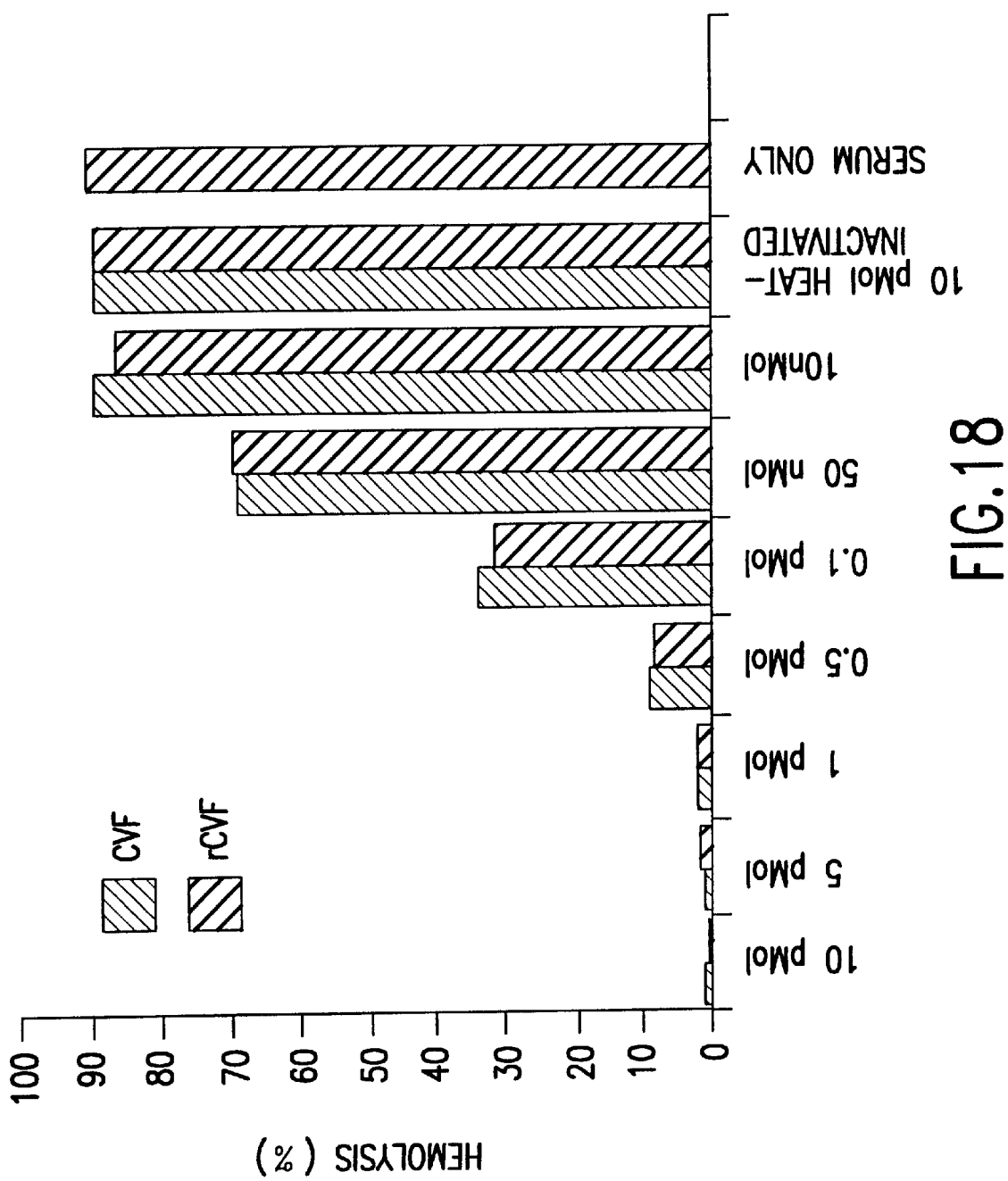
FIG. 18 illustrates the hemolytic activity of recombinant proCVF expressed using the transfer vector pAC-CVF-secr.
Figure 19:
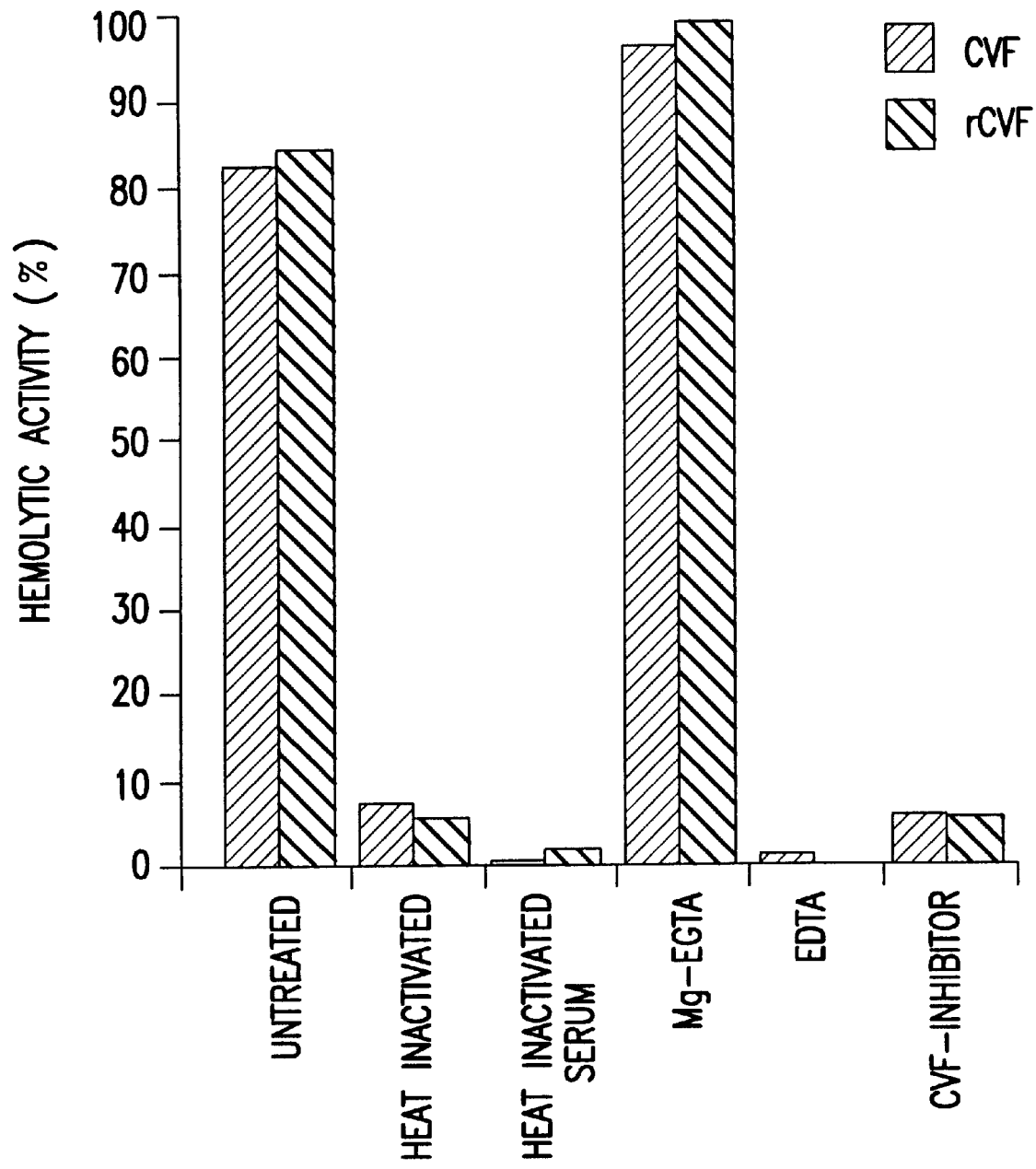
FIG. 19 illustrates the hemolytic activity of recombinant proCVF expressed using the transfer vector PAcGP67-CVF.
Figure 20:
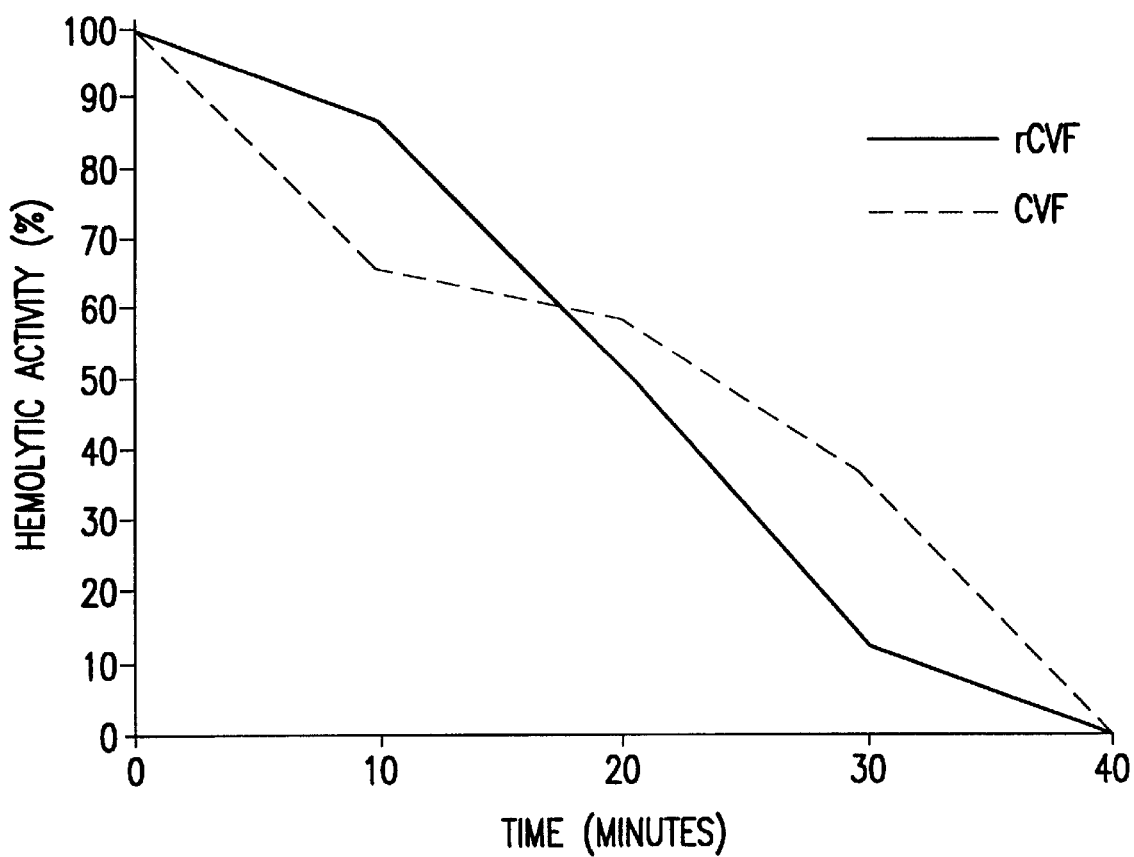
FIG. 20 graphically illustrates the temperature stabilities of recombinant CVF and proCVF.

Purified recombinant proCVF analyzed electrophoretically under reducing and nonreducing conditions, differed from the behavior of natural CVF. Natural CVF resolves in three bands of 68.5 kDa, 48.5 kDa, and 32 kDa. The recombinant proCVF expressed and purified under normal conditions, is produced as the single-chain proCVF (FIG. 15) with a molecular weight of about 190–200 kDa.

The N-terminus was sequenced following SDS-PAGE and electroblotting to ProBlott membrane and was found to be the same as that of the CVF α-chain. This result strongly suggests that the signal peptide is removed but that there is near no (<10%) cleavage in the $(Arg)_4$ linkage between the CVFα- and γ-chain.

Incubation of the cell-free supernatant after the expression at 4° C. for 4 days resulted in an in vitro-processing up to 100%. The resulting protein analyzed electrophoretically behaved similar to human C3 resolving into bands of 115 kDa and 65 kDa. The 115 kDa chain normally resolves to a double band indicating unspecific proteolysis. N-terminal sequencing of the separated 115 kDa bands was not possible to perform, probably due to heterogeneous N-termini.

Glycosylation of Recombinant ProCVF

Natural CVF from *Naja naja* kaouthia contains nearly exclusively asparagine-linked oligosaccharides. The major N-linked oligosaccharide is a symmetrical fucosylated biantennary complex-type structure terminating with an unusual α-galactosyl residue (D. C. Gowda et al, *Mol. Immunol*., vol. 29, pp. 335–342 (1992)).

For recombinant proCVF there is a strong reaction with *Canavalia ensiformis* agglutinin (ConA) and *Galanthus nivalis* agglutinin (GNA) indicating N-linked oligosaccharides of "high-mannose"-type (FIG. 16). A positive reaction with peanut agglutinin (PNA) indicates a O-linked glycosylation of the simple galactose-β(1–3)-N-acetylgalactosamine type. No complex O-glycosylation was detected by reaction with *Datura stramonium* agglutinin (DSA). No sialic acid was found in either natural and recombinant proCVF. These results are consistent with the glycosylation patterns normally found in insect cells. However, natural and recombinant proCVF differ in their glycosylation structure. The N-linked oligosaccharides seem to be more simple for the recombinant one. In contrast to natural CVF, recombinant proCVF seems to have a reasonable amount of O-glycosylation.

Glycosylation of natural CVF is not required for is complement-activating function. However, there are hints that the oligosaccharide structure contributes to the thermal stability of the molecule, because the deglycosylation causes CVF to be more sensitive to temperature (D. C. Gowda et al, *J. Immunol*., vol. 152, pp. 2977–2986 (1994).

Treatment of insect cells with tunicamycin, a strong inhibitor of N-linked glycosylation, results in a complete stop of section (FIG. 17) decreased expression, intracellular accumulation, and degradation of recombinant proCVF. These results are consistent with several others found for insect and mammalian cells. Glycosylation seems to be necessary for proper secretion of some proteins Treatment of mammalian cell lines, expressing complement factors C2, C4 and B, with tunicamycin also results in a complete inhibition of secretion (W. J. Matthews, Jr. et al, *Biochem J*., vol. 204, pp. 839–846 (1982)).

Functional Activity of Recombinant ProCVF

To determine whether recombinant proCVF can activate complement, two assay systems were used. One assay is based on fluid-phase C5 cleavage and bystander lysis of guinea pig erythrocytes by complement activation in guinea pig serum from CVF. The other assay depends on complement consumption by incubation of guinea pig or human normal serum with CVF/recombinant proCVF. Remaining complement activity in the serum is measured by lysis of antibody-sensitized sheep erythrocytes.

The activity for proCVF expressed using the transfer vector pAC-CVF-secr and PAcGP67-CVF was found to be identical. Both assays demonstrate, that the recombinant proCVF has the same complement-activating activity of the natural protein (FIGS. 18 and 19). Even the thermal stability seems to be the same (FIG. 20).

However, the activity for proCVF expressed using the transfer vector pAc-CVF-secr-3'His differs from the activity of natural CVF. While the complement-consumption activity was present in at least the same level as that for the natural protein, activity in the bystander lysis assay was not detectable. These results demonstrate, that the modification of proCVF by addition of six histidine residues at the C-terminus of the proCVF deletes the ability of proCVF to cleave C5 in the fluid-phase.

3. Conclusion

CVF is expressed in the baculovirus system as a single chain proprotein. Production of a broad spectrum of proteins in eukaryotes occurs via an intricate cascade of biosynthetic and secretory processes. Often these proteins initially are synthesized as parts of higher molecular weight, but inactive, precursor proteins. Specific endoproteolytic processing of these proteins is required to generate a mature and biologically active form Such endoproteolysis generally occurs at cleavage sites consisting of particular sequence motifs of basic amino acids, often paired basic residues. Examples for enzymes with a cleavage specificity for basic amino acids are kexin from *Saccharomyces cerevisiae* or the mammalian enzyme furin (W. J. Van de Ven et al, *Crit. Rev. Oncog.*, vol. 4, pp. 115–136 (1993)). Furin is expressed in a wide variety of tissues, perhaps even in all tissues. In all likelihood, it is the enzyme responsible for the proteolytic bioactivation of a wide variety of precursor proteins (e.g., proC3).

Surprisingly, for proCVF the lack of proteolytic processing does not have an effect on activity. This is a very rare, unpredictable event, since there are only a few cases for functionally active proproteins (B. P. Dunker et al, *Biochem. BioPhys. Res. Commun.*, vol. 203, pp. 1851–1857 (1994); N. Moguilevsky et al, *Eur. J. Biochem.*, vol. 197, pp. 605–614 (1991); J. I. Paul et al, *J. Biol. Chem.*, vol. 265, pp. 13074–13083 (1990).

It should be understood that proCVF may be prepared by expressing a single DNA sequence which encodes, e.g., pre-pro-CVF1, pro-CVF1, pre-pro-CVF2, or pro-CVF2, with any post translational processing being carried out as described above.

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by letters patent of the united states is:

1. A method of decomplementation, comprising administering to an animal in need thereof an effective amount of a polypeptide, said polypeptide comprising an amino acid sequence, said amino acid sequence being selected from the group consisting of:

(a) from position about −22 to position about 1620 of the amino acid sequence shown in FIG. 2 (amino acids 1–1642 at SEQ ID NO:2);

(b) from position about −22 to position about 1620 of the amino acid sequence shown in FIG. 2 (amino acids 1–1642 at SEQ ID NO:2) with 1 to 8 histidine residues added to the carboxy terminus;

(c) from position about −22 to position about 1620 of the amino acid sequence shown in FIG. 2 (amino acids 1–1642 at SEQ ID NO:2) with 1 to 8 histidine residues inserted between position −1 and position 1;

(d) from position about 1 to position about 1620 of the amino acid sequence shown in FIG. 2 (amino acids 23–1642 at SEQ ID NO:2);

(e) from position about 1 to position about 1620 of the amino acid sequence shown in FIG. 2 (amino acids 23–1642 at SEQ ID NO:2) with a methionine residue added to the amino terminus;

(f) from position about 1 to position about 1620 of the amino acid sequence shown in FIG. 2 (amino acids 23–1642 at SEQ ID NO:2) with the signal peptide of the baculovirus glycoprotein gp67 (sequence I) added to the amino terminus;

(g) from position about 1 to position about 1620 of the amino acid sequence shown in FIG. 2 (amino acids 23–1642 at SEQ ID NO:2) with the peptide of sequence II added to the amino terminus;

(h) from position about 1 to position about 1620 of the amino acid sequence shown in FIG. 2 (amino acids 23–1642 at SEQ ID NO:2) with 1 to 8 histidine residues added to the carboxy terminus;

(i) from position about 1 to position about 1620 of the amino acid sequence shown in FIG. 2 (amino acids 23–1642 at SEQ ID NO:2) with 1 to 8 histidine residues added to the amino terminus;

(j) from position about 1 to position about 1620 of the amino acid sequence shown in FIG. 2 (amino acids 23–1642 at SEQ ID NO:2) with 1 to 8 histidine residues added to the carboxy terminus and a methionine residue added to the amino terminus;

(k) from position about 1 to position about 1620 of the amino acid sequence shown in FIG. 2 (amino acids 23–1642 at SEQ ID NO:2) with 1 to 8 histidine residues added to the amino terminus and a methionine residue added to the amino terminus of the histidine residues;

(l) from position about 1 to position about 1620 of the amino acid sequence shown in FIG. 2 (amino acids 23–1642 at SEQ ID NO:2) with the signal peptide of the baculovirus glycoprotein gp67 (sequence I) added to the amino terminus and with 1 to 8 histidine residues added to the carboxy terminus; and (m) from position about 1 to position about 1620 of the amino acid sequence shown in FIG. 2 (amino acids 23–1642 at SEQ ID NO:2) and with 1 to 8 histidine residues added to the amino terminus and the signal peptide of the baculovirus glycoprotein gp67 (sequence I) added to the amino terminus of the histidine residues;

wherein sequence I (gp67 signal peptide) is:
MLLVNQSHQGFNKEHTSKMVSAIVLYVL-LAAAAHSAFA (SEQ ID NO:36);

and sequence II (peptide encoding for M start codon, 6 histidine residues, and enterokinase cleavage site) is
MRGSHHHHHHGMASMTGGQQMGRD-LYNNNK (SEQ ID NO:37).

2. The method of claim 1, wherein said polypeptide is:

(d) from position about 1 to position about 1620 of the amino acid sequence shown in FIG. 2 (amino acids 23–1642 at SEQ ID NO:2).

3. The method of claim 1, wherein said animal is a reptile, fish, bird, or mammal.

4. The method of claim 1, wherein said animal is a mammal selected from the group consisting of guinea pigs, mice, rats, pigs, baboons, chimps, dogs, cats, horses, cows, and humans.

5. The method of claim 1, wherein said animal is suffering from septic shock, ischemia-reperfusion injury, thermal injury, arthritis, lupus, respiratory distress syndrome, or a tissue rejection.

6. The method of claim 1, wherein said polypeptide is administered in an amount of 1 to 1000 U/kg of body weight.

7. The method of claim 1, wherein said polypeptide is administered in an amount of 30 to 80 U/kg of body weight.

* * * * *